(12) United States Patent
Felts et al.

(10) Patent No.: US 9,272,095 B2
(45) Date of Patent: Mar. 1, 2016

(54) VESSELS, CONTACT SURFACES, AND COATING AND INSPECTION APPARATUS AND METHODS

(75) Inventors: John T. Felts, Alameda, CA (US);
Thomas E. Fisk, Green Valley, AZ (US);
Robert Abrams, Albany, NY (US);
John Ferguson, Auburn, AL (US);
Jonathan Freedman, Auburn, AL (US);
Robert Pangborn, Harbor Springs, MI (US); Peter Sagona, Pottstown, PA (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 630 days.

(21) Appl. No.: 13/436,252

(22) Filed: Mar. 30, 2012

(65) Prior Publication Data

US 2012/0252709 A1 Oct. 4, 2012

Related U.S. Application Data

(60) Provisional application No. 61/471,056, filed on Apr. 1, 2011.

(51) Int. Cl.
*A61M 5/31* (2006.01)
*C23C 16/02* (2006.01)
(Continued)

(52) U.S. Cl.
CPC .......... *A61M 5/3129* (2013.01); *C23C 16/0272* (2013.01); *C23C 16/045* (2013.01);
(Continued)

(58) Field of Classification Search
USPC ................................................ 508/100, 110
See application file for complete search history.

(56) References Cited

U.S. PATENT DOCUMENTS 3,274,267 A 9/1966 Chow
3,297,465 A 1/1967 Connell
(Continued)

FOREIGN PATENT DOCUMENTS

AT 414209 B 10/2006
AT 504533 A1 6/2008
(Continued)

OTHER PUBLICATIONS

PCT, Notification of Transmittal of the International Search Report and the Written Opinion of the International Searching Authority, or the Declaration, in International application No. PCT/US2013/064121, dated Mar. 24, 2014. (8 pages).
(Continued)

*Primary Examiner* — Ellen McAvoy
(74) *Attorney, Agent, or Firm* — McAndrews, Held & Malloy, Ltd.

(57) ABSTRACT

Methods for processing a contact surface, for example to provide a gas barrier or lubricity or to modify the wetting properties on a medical device, are disclosed. First and second PECVD or other contact surface processing stations or devices and a contact surface holder comprising a contact surface port are provided. An opening of the contact surface can be seated on the contact surface port. The interior contact surface of the seated contact surface can be processed via the contact surface port by the first and second processing stations or devices. contact surface barrier, lubricity and hydrophobic coatings and coated contact surfaces, for example syringes and medical sample collection tubes are disclosed. A contact surface processing system and contact surface inspection apparatus and methods are also disclosed.

9 Claims, 5 Drawing Sheets

(51) Int. Cl.
*C23C 16/04* (2006.01)
*C23C 16/30* (2006.01)
*C23C 16/36* (2006.01)

(52) U.S. Cl.
CPC .............. *C23C 16/30* (2013.01); *C23C 16/36* (2013.01); *A61M 2005/3104* (2013.01); *A61M 2005/3131* (2013.01)

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tompkins |
| 3,957,653 A | 5/1976 | Blecher |
| 4,111,326 A | 9/1978 | Percarpio |
| 4,118,972 A | 10/1978 | Goeppner |
| 4,134,832 A | 1/1979 | Heimreid |
| 4,136,794 A | 1/1979 | Percarpio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantei |
| 4,484,479 A | 11/1984 | Eckhardt |
| 4,486,378 A | 12/1984 | Hirata |
| 4,522,510 A | 6/1985 | Rosencwaig |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,810,752 A | 3/1989 | Bayan |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,978,714 A | 12/1990 | Bayan |
| 4,991,104 A | 2/1991 | Miller |
| 4,999,014 A | 3/1991 | Gold |
| 5,000,994 A | 3/1991 | Romberg |
| 5,009,646 A | 4/1991 | Sudo |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,288,560 A | 2/1994 | Sudo |
| 5,292,370 A | 3/1994 | Tsai |
| 5,294,011 A | 3/1994 | Konrad |
| 5,294,464 A | 3/1994 | Geisler |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,395,644 A | 3/1995 | Affinito |
| 5,396,080 A | 3/1995 | Hannotiau |
| 5,397,956 A | 3/1995 | Araki |
| 5,413,813 A | 5/1995 | Cruse |

(56) References Cited

U.S. PATENT DOCUMENTS

| | | |
|---|---|---|
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babcock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,550 A | 8/1998 | Phillips |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Buch-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman |
| 6,085,927 A | 7/2000 | Kusz |
| 6,090,081 A | 7/2000 | Sudo |
| 6,093,175 A | 7/2000 | Gyure |
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,125,687 A | 10/2000 | McClelland |

(56) References Cited

U.S. PATENT DOCUMENTS

| | | | |
|---|---|---|---|
| 6,126,640 A | 10/2000 | Tucker | |
| 6,129,712 A | 10/2000 | Sudo | |
| 6,129,956 A | 10/2000 | Morra | |
| 6,136,275 A | 10/2000 | Niermann | |
| 6,139,802 A | 10/2000 | Niermann | |
| 6,143,140 A | 11/2000 | Wang | |
| 6,149,982 A | 11/2000 | Plester | |
| 6,153,269 A | 11/2000 | Gleason | |
| 6,156,152 A | 12/2000 | Ogino | |
| 6,156,399 A | 12/2000 | Spallek | |
| 6,156,435 A | 12/2000 | Gleason | |
| 6,160,350 A | 12/2000 | Sakemi | |
| 6,161,712 A | 12/2000 | Savitz | |
| 6,163,006 A | 12/2000 | Doughty | |
| 6,165,138 A | 12/2000 | Miller | |
| 6,165,542 A | 12/2000 | Jaworowski | |
| 6,165,566 A | 12/2000 | Tropsha | |
| 6,171,670 B1 | 1/2001 | Sudo | |
| 6,175,612 B1 | 1/2001 | Sato | |
| 6,177,142 B1 | 1/2001 | Felts | |
| 6,180,185 B1 | 1/2001 | Felts | |
| 6,180,191 B1 | 1/2001 | Felts | |
| 6,188,079 B1 | 2/2001 | Juvinall | |
| 6,189,484 B1 | 2/2001 | Yin | |
| 6,190,992 B1 | 2/2001 | Sandhu | |
| 6,193,853 B1 | 2/2001 | Yumshtyk | |
| 6,196,155 B1 | 3/2001 | Setoyama | |
| 6,197,166 B1 | 3/2001 | Moslehi | |
| 6,200,658 B1 | 3/2001 | Walther | |
| 6,200,675 B1 | 3/2001 | Neerinck | |
| 6,204,922 B1 | 3/2001 | Chalmers | |
| 6,210,791 B1 | 4/2001 | Skoog | |
| 6,214,422 B1 | 4/2001 | Yializis | |
| 6,217,716 B1 | 4/2001 | Fai Lai | |
| 6,223,683 B1 | 5/2001 | Plester | |
| 6,236,459 B1 | 5/2001 | Negahdaripour | |
| 6,245,190 B1 | 6/2001 | Masuda | |
| 6,248,219 B1 | 6/2001 | Wellerdieck | |
| 6,248,397 B1 | 6/2001 | Ye | |
| 6,251,792 B1 | 6/2001 | Collins | |
| 6,254,983 B1 | 7/2001 | Namiki | |
| 6,261,643 B1 | 7/2001 | Hasz | |
| 6,263,249 B1 * | 7/2001 | Stewart et al. | 607/116 |
| 6,271,047 B1 | 8/2001 | Ushio | |
| 6,276,296 B1 | 8/2001 | Plester | |
| 6,277,331 B1 | 8/2001 | Konrad | |
| 6,279,505 B1 | 8/2001 | Plester | |
| 6,284,986 B1 | 9/2001 | Dietze | |
| 6,306,132 B1 | 10/2001 | Moorman | |
| 6,308,556 B1 | 10/2001 | Sagi | |
| 6,322,661 B1 | 11/2001 | Bailey, III | |
| 6,331,174 B1 | 12/2001 | Reinhard et al. | |
| 6,344,034 B1 | 2/2002 | Sudo | |
| 6,346,596 B1 | 2/2002 | Mallen | |
| 6,348,967 B1 | 2/2002 | Nelson | |
| 6,350,415 B1 | 2/2002 | Niermann | |
| 6,351,075 B1 | 2/2002 | Barankova | |
| 6,352,629 B1 | 3/2002 | Wang | |
| 6,354,452 B1 | 3/2002 | DeSalvo | |
| 6,355,033 B1 | 3/2002 | Moorman | |
| 6,365,013 B1 | 4/2002 | Beele | |
| 6,375,022 B1 | 4/2002 | Zurcher | |
| 6,376,028 B1 | 4/2002 | Laurent | |
| 6,379,757 B1 | 4/2002 | Iacovangelo | |
| 6,382,441 B1 | 5/2002 | Carano | |
| 6,394,979 B1 | 5/2002 | Sharp | |
| 6,396,024 B1 | 5/2002 | Doughty | |
| 6,399,944 B1 | 6/2002 | Vasilyev | |
| 6,402,885 B2 | 6/2002 | Loewenhardt | |
| 6,406,792 B1 * | 6/2002 | Briquet et al. | 428/447 |
| 6,410,926 B1 | 6/2002 | Munro | |
| 6,413,645 B1 | 7/2002 | Graff | |
| 6,432,494 B1 | 8/2002 | Yang | |
| 6,470,650 B1 | 10/2002 | Lohwasser | |
| 6,471,822 B1 | 10/2002 | Yin | |
| 6,475,622 B2 | 11/2002 | Namiki | |
| 6,482,509 B2 | 11/2002 | Buch-Rasmussen et al. | |
| 6,486,081 B1 | 11/2002 | Ishikawa | |
| 6,500,500 B1 | 12/2002 | Okamura | |
| 6,503,579 B1 | 1/2003 | Murakami | |
| 6,518,195 B1 | 2/2003 | Collins | |
| 6,524,282 B1 | 2/2003 | Sudo | |
| 6,524,448 B2 | 2/2003 | Brinkmann | |
| 6,539,890 B1 | 4/2003 | Felts | |
| 6,544,610 B1 | 4/2003 | Minami | |
| 6,551,267 B1 | 4/2003 | Cohen | |
| 6,558,679 B2 | 5/2003 | Flament-Garcia et al. | |
| 6,562,010 B1 | 5/2003 | Gyure | |
| 6,562,189 B1 | 5/2003 | Carducci | |
| 6,565,791 B1 | 5/2003 | Laurent | |
| 6,582,426 B2 | 6/2003 | Moorman | |
| 6,582,823 B1 | 6/2003 | Sakhrani et al. | |
| 6,584,828 B2 | 7/2003 | Sagi | |
| 6,595,961 B2 | 7/2003 | Hetzler | |
| 6,597,193 B2 | 7/2003 | Lagowski | |
| 6,599,569 B1 | 7/2003 | Humele | |
| 6,599,594 B1 | 7/2003 | Walther | |
| 6,602,206 B1 | 8/2003 | Niermann | |
| 6,616,632 B2 | 9/2003 | Sharp | |
| 6,620,139 B1 | 9/2003 | Plicchi | |
| 6,620,334 B2 | 9/2003 | Kanno | |
| 6,623,861 B2 | 9/2003 | Martin | |
| 6,638,403 B1 | 10/2003 | Inaba | |
| 6,638,876 B2 | 10/2003 | Levy | |
| 6,645,354 B1 | 11/2003 | Gorokhovsky | |
| 6,645,635 B2 | 11/2003 | Muraki | |
| 6,651,835 B2 | 11/2003 | Iskra | |
| 6,652,520 B2 | 11/2003 | Moorman | |
| 6,656,540 B2 | 12/2003 | Sakamoto | |
| 6,658,919 B2 | 12/2003 | Chatard | |
| 6,662,957 B2 | 12/2003 | Zurcher | |
| 6,663,601 B2 | 12/2003 | Hetzler | |
| 6,663,603 B1 | 12/2003 | Gyure | |
| 6,670,200 B2 | 12/2003 | Ushio | |
| 6,673,199 B1 | 1/2004 | Yamartino | |
| 6,680,091 B2 | 1/2004 | Buch-Rasmussen et al. | |
| 6,680,621 B2 | 1/2004 | Savtchouk | |
| 6,683,308 B2 | 1/2004 | Itagaki | |
| 6,684,683 B2 | 2/2004 | Potyrailo | |
| 6,702,898 B2 | 3/2004 | Hosoi | |
| 6,706,412 B2 | 3/2004 | Yializis | |
| 6,746,430 B2 | 6/2004 | Lubrecht | |
| 6,749,078 B2 | 6/2004 | Iskra | |
| 6,752,899 B1 | 6/2004 | Singh | |
| 6,753,972 B1 | 6/2004 | Hirose | |
| 6,757,056 B1 | 6/2004 | Meeks | |
| 6,764,714 B2 | 7/2004 | Wei | |
| 6,765,466 B2 | 7/2004 | Miyata | |
| 6,766,682 B2 | 7/2004 | Engle | |
| 6,774,018 B2 | 8/2004 | Mikhael | |
| 6,796,780 B1 | 9/2004 | Chatard | |
| 6,800,852 B2 | 10/2004 | Larson | |
| 6,808,753 B2 | 10/2004 | Rule | |
| 6,810,106 B2 | 10/2004 | Sato | |
| 6,815,014 B2 | 11/2004 | Gabelnick | |
| 6,818,310 B2 | 11/2004 | Namiki | |
| 6,822,015 B2 | 11/2004 | Muraki | |
| 6,837,954 B2 | 1/2005 | Carano | |
| 6,844,075 B1 | 1/2005 | Saak | |
| 6,853,141 B2 | 2/2005 | Hoffman | |
| 6,858,259 B2 | 2/2005 | Affinito | |
| 6,863,731 B2 | 3/2005 | Elsayed-Ali | |
| 6,864,773 B2 | 3/2005 | Perrin | |
| 6,866,656 B2 | 3/2005 | Tingey | |
| 6,872,428 B2 | 3/2005 | Yang | |
| 6,876,154 B2 | 4/2005 | Appleyard | |
| 6,885,727 B2 | 4/2005 | Tamura | |
| 6,887,578 B2 | 5/2005 | Gleason | |
| 6,891,158 B2 | 5/2005 | Larson | |
| 6,892,567 B1 | 5/2005 | Morrow | |
| 6,899,054 B1 | 5/2005 | Bardos | |
| 6,905,769 B2 | 6/2005 | Komada | |
| 6,910,597 B2 | 6/2005 | Iskra | |
| 6,911,779 B2 | 6/2005 | Madocks | |

(56) References Cited

U.S. PATENT DOCUMENTS

| | | |
|---|---|---|
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,183,197 B2 | 2/2007 | Won |
| 7,186,242 B2 | 3/2007 | Gyure |
| 7,188,734 B2 | 3/2007 | Konrad |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,214,214 B2 | 5/2007 | Sudo |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,547,297 B2 | 6/2009 | Brinkhues |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,579,056 B2 | 8/2009 | Brown |
| 7,582,868 B2 | 9/2009 | Jiang |
| 7,595,097 B2 | 9/2009 | Iacovangelo |
| 7,608,151 B2 | 10/2009 | Tudhope |
| 7,618,686 B2 | 11/2009 | Colpo |
| 7,624,622 B1 | 12/2009 | Mayer |
| 7,625,494 B2 | 12/2009 | Honda |
| 7,645,696 B1 | 1/2010 | Dulkin |
| 7,648,481 B2 | 1/2010 | Geiger |
| 7,682,816 B2 | 3/2010 | Kim |
| 7,691,308 B2 | 4/2010 | Brinkhues |
| 7,694,403 B2 | 4/2010 | Moulton |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,202 B2 | 7/2010 | Miller |
| 7,749,914 B2 | 7/2010 | Honda |
| 7,754,302 B2 | 7/2010 | Yamasaki |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahern |
| 7,807,242 B2 | 10/2010 | Soerensen |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,905,866 B2 | 3/2011 | Haider |
| 7,922,880 B1 | 4/2011 | Pradhan |
| 7,922,958 B2 | 4/2011 | D'Arrigo |
| 7,927,315 B2 | 4/2011 | Sudo |
| 7,931,955 B2 | 4/2011 | Behle |
| 7,932,678 B2 | 4/2011 | Madocks |
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 * | 7/2011 | Felts et al. ............... 600/573 |
| 8,002,754 B2 | 8/2011 | Kawamura |
| 8,025,915 B2 | 9/2011 | Haines |
| 8,038,858 B1 | 10/2011 | Bures |
| 8,039,524 B2 | 10/2011 | Chappa |
| 8,056,719 B2 | 11/2011 | Porret |
| 8,062,266 B2 | 11/2011 | McKinnon |
| 8,066,663 B2 | 11/2011 | Sudo |
| 8,066,854 B2 | 11/2011 | Storey |
| 8,070,917 B2 | 12/2011 | Tsukamoto |
| 8,075,995 B2 | 12/2011 | Zhao |
| 8,092,605 B2 | 1/2012 | Shannon |
| 8,101,246 B2 | 1/2012 | Fayet |
| 8,101,674 B2 | 1/2012 | Kawauchi |
| 8,105,294 B2 | 1/2012 | Araki |
| 8,197,452 B2 | 6/2012 | Harding |
| 8,258,486 B2 | 9/2012 | Avnery |
| 8,268,410 B2 | 9/2012 | Moelle |
| 8,273,222 B2 | 9/2012 | Wei |
| 8,277,025 B2 | 10/2012 | Nakazawa et al. |
| 8,313,455 B2 | 11/2012 | Digregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |

(56) References Cited

U.S. PATENT DOCUMENTS

| | | |
|---|---|---|
| 8,418,650 B2 | 4/2013 | Goto |
| 8,435,605 B2 | 5/2013 | Aitken et al. |
| 8,475,886 B2 | 7/2013 | Chen et al. |
| 8,512,796 B2 * | 8/2013 | Felts et al. .................. 427/2.3 |
| 8,524,331 B2 | 9/2013 | Honda |
| 8,592,015 B2 | 11/2013 | Bicker |
| 8,597,720 B2 * | 12/2013 | Hoffmann et al. ............ 427/2.3 |
| 8,603,638 B2 | 12/2013 | Liu |
| 8,618,509 B2 | 12/2013 | Vo-Dinh |
| 8,623,324 B2 | 1/2014 | Diwu |
| 8,633,034 B2 | 1/2014 | Trotter |
| 8,747,962 B2 | 6/2014 | Bicker |
| 8,802,603 B2 * | 8/2014 | D'Souza et al. ............. 508/173 |
| 8,816,022 B2 | 8/2014 | Zhao |
| 9,068,565 B2 | 6/2015 | Alarcon |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130674 A1 | 9/2002 | Lagowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0176947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0102087 A1 | 6/2003 | Ito |
| 2003/0119193 A1 | 6/2003 | Hess |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Hetzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0177676 A1 | 9/2004 | Moore |
| 2004/0195960 A1 | 10/2004 | Czeremuszkin |
| 2004/0206309 A1 | 10/2004 | Bera |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahern |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Hetzler |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kitzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0127443 A1 * | 6/2006 | Helmus .................. 424/423 |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belov |
| 2007/0048456 A1 | 3/2007 | Keshner |
| 2007/0049048 A1 | 3/2007 | Rauf |
| 2007/0051629 A1 | 3/2007 | Dolnik |
| 2007/0065680 A1 | 3/2007 | Schultheis |
| 2007/0076833 A1 | 4/2007 | Becker |
| 2007/0102344 A1 | 5/2007 | Konrad |
| 2007/0123920 A1 | 5/2007 | Inokuti |
| 2007/0148326 A1 | 6/2007 | Hatings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke et al. |
| 2007/0218265 A1 | 9/2007 | Harris |
| 2007/0224236 A1 | 9/2007 | Boden |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Rius |
| 2008/0017113 A1 | 1/2008 | Goto |

(56) References Cited

U.S. PATENT DOCUMENTS

| | | |
|---|---|---|
| 2008/0023414 A1 | 1/2008 | Konrad |
| 2008/0027400 A1 | 1/2008 | Harding |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0081184 A1 | 4/2008 | Kubo |
| 2008/0090039 A1 | 4/2008 | Klein |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0145271 A1 | 6/2008 | Kidambi |
| 2008/0187681 A1 | 8/2008 | Hofrichter |
| 2008/0195059 A1 | 8/2008 | Sudo |
| 2008/0202414 A1 | 8/2008 | Yan |
| 2008/0206477 A1 | 8/2008 | Rius |
| 2008/0210550 A1 | 9/2008 | Walther |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0268252 A1 | 10/2008 | Garces |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | Mcelrea |
| 2008/0312607 A1 | 12/2008 | Delmotte |
| 2008/0314318 A1 | 12/2008 | Han |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Loboda |
| 2009/0061237 A1 | 3/2009 | Gates |
| 2009/0065485 A1 | 3/2009 | O'Neill |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Kang |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0220948 A1 | 9/2009 | Oviso et al. |
| 2009/0263668 A1 | 10/2009 | David |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0042055 A1 | 2/2010 | Sudo |
| 2010/0075077 A1 | 3/2010 | Bicker |
| 2010/0089097 A1 | 4/2010 | Brack |
| 2010/0105208 A1 | 4/2010 | Winniczek |
| 2010/0132762 A1 | 6/2010 | Graham, Jr. |
| 2010/0136073 A1* | 6/2010 | Preuss et al. .................. 424/404 |
| 2010/0145284 A1 | 6/2010 | Togashi |
| 2010/0174239 A1 | 7/2010 | Yodfat |
| 2010/0174245 A1 | 7/2010 | Halverson |
| 2010/0178490 A1 | 7/2010 | Cerny |
| 2010/0185157 A1 | 7/2010 | Kawamura |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0198554 A1 | 8/2010 | Skliar |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0264139 A1 | 10/2010 | Kawachi |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1 | 11/2010 | Felts |
| 2010/0298779 A1 | 11/2010 | Hetzler |
| 2011/0037159 A1 | 2/2011 | Mcelrea |
| 2011/0046570 A1 | 2/2011 | Stout |
| 2011/0056912 A1 | 3/2011 | Matsuyama |
| 2011/0062047 A1 | 3/2011 | Haines |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr. |
| 2011/0117288 A1 | 5/2011 | Honda |
| 2011/0137263 A1 | 6/2011 | Ashmead |
| 2011/0152820 A1 | 6/2011 | Chattaraj |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan |
| 2011/0220490 A1 | 9/2011 | Wei |
| 2011/0252899 A1 | 10/2011 | Felts |
| 2011/0253674 A1 | 10/2011 | Chung |
| 2011/0313363 A1* | 12/2011 | D'Souza et al. .............. 604/187 |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |
| 2012/0108058 A1 | 5/2012 | Ha |
| 2012/0109076 A1 | 5/2012 | Kawamura |
| 2012/0123345 A1 | 5/2012 | Felts |
| 2012/0143148 A1 | 6/2012 | Zhao |
| 2012/0149871 A1 | 6/2012 | Saxena |
| 2012/0171386 A1 | 7/2012 | Bicker |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1 | 10/2012 | Felts |
| 2013/0041241 A1* | 2/2013 | Felts et al. ................... 600/364 |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0296235 A1 | 11/2013 | Alarcon |
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |

(56) References Cited

U.S. PATENT DOCUMENTS

| | | | |
|---|---|---|---|
| 2014/0110297 A1 | 4/2014 | Trotter | |
| 2014/0135708 A1 | 5/2014 | Lewis | |
| 2014/0147654 A1 | 5/2014 | Walther | |
| 2014/0151320 A1 | 6/2014 | Chang | |
| 2014/0151370 A1 | 6/2014 | Chang | |
| 2014/0154399 A1* | 6/2014 | Weikart et al. | 427/2.3 |
| 2014/0187666 A1 | 7/2014 | Aizenberg | |
| 2014/0190846 A1 | 7/2014 | Belt | |
| 2014/0221934 A1 | 8/2014 | Janvier | |
| 2014/0251856 A1 | 9/2014 | Larsson | |
| 2014/0305830 A1 | 10/2014 | Bicker | |
| 2015/0165125 A1 | 6/2015 | Foucher | |
| 2015/0224263 A1 | 8/2015 | Dugand | |

FOREIGN PATENT DOCUMENTS

| | | |
|---|---|---|
| AU | 2002354470 B2 | 5/2007 |
| CA | 2085805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CN | 2546041 Y | 4/2003 |
| CN | 1711310 A | 12/2005 |
| CN | 2766863 Y | 3/2006 |
| CN | 1898172 A | 1/2007 |
| CN | 201002786 Y | 1/2008 |
| CN | 101147813 A | 3/2008 |
| CN | 201056331 Y | 5/2008 |
| CN | 102581274 A | 7/2012 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 197076454 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0251812 A2 | 1/1988 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |
| EP | 1507723 | 3/2006 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2602354 A1 | 6/2013 |
| EP | 2639330 A1 | 9/2013 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | 05-096688 | 4/1993 |
| JP | H05263223 A | 10/1993 |
| JP | 6010132 A | 1/1994 |
| JP | 6289401 | 10/1994 |
| JP | 7041579 A | 2/1995 |

(56) References Cited

FOREIGN PATENT DOCUMENTS

| | | |
|---|---|---|
| JP | 7068614 A | 3/1995 |
| JP | 7126419 A | 5/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005200044 A | 7/2005 |
| JP | 2005-241524 A | 9/2005 |
| JP | 2005271997 A | 10/2005 |
| JP | 2005290561 A | 10/2005 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2012210315 A | 11/2012 |
| KR | 10-2006-0029694 | 4/2006 |
| KR | 10-0685594 B1 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO9624392 A1 | 8/1996 |
| WO | WO97/11482 | 3/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO02076709 A1 | 10/2002 |
| WO | WO03014415 A1 | 2/2003 |
| WO | WO03033426 | 4/2003 |
| WO | WO03038143 | 5/2003 |
| WO | WO03040649 A1 | 5/2003 |
| WO | WO03044240 A1 | 5/2003 |
| WO | WO2005035147 A1 | 4/2005 |
| WO | WO2005/052555 A1 | 6/2005 |
| WO | WO2005051525 A1 | 6/2005 |
| WO | WO2005103605 A1 | 11/2005 |
| WO | WO2006012881 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006048276 | 5/2006 |
| WO | WO2006048277 A1 | 5/2006 |
| WO | WO2006069774 A1 | 7/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A2 | 11/2007 |
| WO | WO2008014438 A2 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 A2 | 11/2010 |
| WO | WO2011029628 | 3/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2013045671 A1 | 4/2013 |
| WO | WO2013/071138 | 5/2013 |
| WO | WO2013/071138 A1 | 5/2013 |
| WO | WO2013/170044 | 11/2013 |

(56) References Cited

FOREIGN PATENT DOCUMENTS

| WO | WO2013/170052 | 11/2013 |
|---|---|---|
| WO | WO2014/008138 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |

OTHER PUBLICATIONS

PCT, Notification of Transmittal of the International Search Report and the Written Opinion of the International Searching Authority, or the Declaration, in International application No. PCT/US2013/070325, dated Mar. 24, 2014. (16 pages).
Australian Government, IP Australia, Patent Examination Report No. 1, in Application No. 2010249031, dated Mar. 13, 2014. (4 pages).
Australian Government, IP Australia, Patent Examination Report No. 1, in Application No. 2013202893, dated Mar. 13, 2014. (4 pages).
European Patent Office, Communication pursuant to Article 93(3) EPC, in Application No. 11 731 554.9 dated Apr. 15, 2014. (7 pages).
PCT, Notification Concerning Transmittal of International Preliminary Report on Patentability, in International application No. PCT/US2012/064489, dated May 22, 2014. (10 pages).
PCT, Notification of Transmittal of the International Search Report and the Written Opinion of the International Searching Authority, or the Declaration, in International application No. PCT/US2013/071750, dated Apr. 4, 2014. (13 pages).
PCT, Notification of Transmittal of the International Search Report and the Written Opinion of the International Searching Authority, or the Declaration, in International application No. PCT/US2014/019684, dated May 23, 2014. (16 pages).
PCT, Notification of Transmittal of the International Search Report and the Written Opinion of the International Searching Authority, or the Declaration, in International application No. PCT/US2014/023813, dated May 22, 2014. (11 pages).
European Patent Office, Communication pursuant to Article 94(3) EPC, in Application No. 11 736 511.4, dated Mar. 28, 2014.
PCT, Notification Concerning Transmittal of International Preliminary Report on Patentability, in International application No. PCT/US2011/042387, dated Jan. 17, 2013. (7 pages).
State Intellectual Property Office of the People's Republic of China, Notification of the First Office Action, in Application No. 201180032145.4, dated Jan. 30, 2014. (16 pages).
PCT, Notification Concerning Transmittal of International Preliminary Report on Patentability, in International application No. PCT/US2011/044215, dated Jan. 31, 2013. (14 pages).
Australian Government, IP Australia, Patent Examination Report No. 1, in Application No. 2012318242, dated Apr. 30, 2014. (6 pages).
State Intellectual Property Office of the People's Republic of China, Notification of the First Office Action, in Application No. 201180023461.5, dated May 21, 2014. (25 pages).
European Patent Office, Communication pursuant to Article 94(3) EPC, in Application No. 10162758.6 dated May 27, 2014. (7 pages).
Allison, H.L., The Real Markets for Transparent Barrier Films, 37th Annual Technical Conference Proceedings, 1994, ISBN 1-878068-13-X, p. 458.
Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.
Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.
Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.

Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, , pp. 112-118.
Bush, V. et al., The Evolution of Evacuated Blood Collection Tubes, BD Diagnostics—Preanalytical Systems Newsletter, vol. 19, No. 1, 2009.
Chahroudi, D., Deposition Technology for Glass Barriers, 33rd Annual Technical Conference Proceedings, 1990, ISBN 1-878068-09-1, pp. 212-220.
Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.
Chahroudi, D., Glassy Barriers from Electron Beam Web Coaters, 32nd Annual Technical Conference Proceedings, 1989, pp. 29-39.
Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.
Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.iop.org/EJ/abstract/0022-3727/36/23/003, printed Jul. 14, 2009.
Egitto, F.D., et al., Plasma Modification of Polymer Surfaces, Society of Vacuum Coaters, 36th Annual Technical Conference Proceedings, 1993, ISBN 1-878068-12-1, pp. 10-21.
Erlat, A.G. et al., SiOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.
Fayet, P., et al., Commercialism of Plasma Deposited Barrier Coatings for Liquid Food Packaging, 37th Annual Technical Conference Proceedings, 1995, ISBN 1-878068-13-X, pp. 15-16.
Felts, J., Hollow Cathode Based Multi-Component Depositions, Vacuum Technology & Coating, Mar. 2004, pp. 48-55.
Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.
Felts, J.T., Transparent Barrier Coatings Update: Flexible Substrates, Society of Vacuum Coaters, 36th Annual Technical Conference Proceedings, 1993, ISBN 1-878068-12-1, pp. 324-331.
Felts, J.T., Transparent Gas Barrier Technologies, 33rd Annual Technical Conference Proceedings, 1990, ISBN 1-878068-09-1, pp. 184-193.
Finson, E., et al., Transparent SiO2 Barrier Coatings: Conversion and Production Status, 37th Annual Technical Conference Proceedings, 1994, ISBN 1-878068-13-X, pp. 139-143.
Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.
Hora, R., et al., Plasma Polymerization: A New Technology for Functional Coatings on Plastics, 36th Annual Technical Conference Proceedings, 1993, ISBN 1-878068-12-1, pp. 51-55.
Izu, M., et al., High Performance Clear CoatTM Barrier Film, 36th Annual Technical Conference Proceedings, 1993, ISBN 1-878068-12-1, pp. 333-340.
Jost, S., Plasma Polymerized Organosilicon Thin Films on Reflective Coatings, 33rd Annual Technical Conference Proceedings, 1990, ISBN 1-878068-09-1, pp. 344-346.
Kaganowicz, G., et al., Plasma-Deposited Coatings—Properties and Applications, 23rd Annual Technical Conference Proceedings, 1980, pp. 24-30.
Kamineni, V. et al., Thickness Measurement of Thin Metal Films by Optical Metrology, College of Nanoscale Science and Engineering, University of Albany, Albany, NY.
Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.
Krug, T., et al., New Developments in Transparent Barrier Coatings, 36th Annual Technical Conference Proceedings, 1993, ISBN 1-878068-12-1, pp. 302-305.

(56) References Cited

OTHER PUBLICATIONS

Kuhr, M. et al., Multifunktionsbeschichtungen für innovative Applikationen von Kunststoff-Substraten, HiCotec Smart Coating Solutions.
Kulshreshtha, D.S., Specifications of a Spectroscopic Ellipsometer, Department of Physics & Astrophysics, University of Delhi, Delhi-110007, Jan. 16, 2009.
Krug, T.G., Transparent Barriers for Food Packaging, 33rd Annual Technical Conference Proceedings, 1990, ISBN 1-878068-09-1, pp. 163-169.
Lee, K. et al., The Ellipsometric Measurements of a Curved Surface, Japanese Journal of Applied Physics, vol. 44, No. 32, 2005, pp. L1015-L1018.
Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.
Masso, J.D., Evaluation of Scratch Resistant and Antireflective Coatings for Plastic Lenses, 32nd Annual Technical Conference Proceedings, 1989, p. 237-240.
Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.
Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.
Mount, E., Measuring Pinhole Resistance of Packaging, Corotec Corporation website, http://www.convertingmagazine.com, printed Jul. 13, 2009.
Murray, L. et al., The Impact of Foil Pinholes and Flex Cracks on the Moisture and Oxygen Barrier of Flexible Packaging.
Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.
Nelson, R.J., Scale-Up of Plasma Deposited SiOx Gas Diffusion Barrier Coatings, 35th Annual Technical Conference Proceedings, 1992, ISBN 1-878068-11-3, pp. 75-78.
Novotny, V. J., Ultrafast Ellipsometric Mapping of Thin Films, IBM Technical Disclosure Bulletin, vol. 37, No. 02A, Feb. 1994, pp. 187-188.
Rüger, M., Die Pulse Sind das Plus, PICVD-Beschichtungsverfahren.
Schultz, A. et al., Detection and Identification of Pinholes in Plasma-Polymerised Thin Film Barrier Coatings on Metal Foils, Surface & Coatings Technology 200, 2005, pp. 213-217.
Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.
Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.
Teyssedre, G. et al., Temperature Dependence of the Photoluminescence in Poly(Ethylene Terephthalate) Films, Polymer 42, 2001, pp. 8207-8216.
Tsung, L. et al., Development of Fast CCD Cameras for In-Situ Electron Microscopy, Microsc Microanal 14(Supp 2), 2008.
Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.
Yang, et al., Microstructure and tribological properties of SiOx/DLC films grown by PECVD, Surface and Coatings Technology, vol. 194, Issue 1, Apr. 20, 2005, pp. 128-135.
An 451, Accurate Thin Film Measurements by High-Resoluiton Transmission Electron Microscopy (HRTEM), Evans Alalytical Group, Version 1.0, Jun. 12, 2008, pp. 1-2.
Benefits of TriboGlide, TriboGlide Silicone-Free Lubrication Systems, http://www.triboglide.com/benfits.htm, printed Aug. 31, 2009.

Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the Internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.
Google search re "cyclic olefin polymer resin" syringe OR vial, http://www.google.com/search?sclient=psy-ab&hl=en&lr=&source=hp
&q=%22cyclic+olefin+polymer+resin%22+syringe+OR+vial
&btnG=Search&pbx=1
&oq=%22cyclic+olefin+polymer+resin%22+syringe+OR+vial
&aq, 1 page, retrieved from the internet Sep. 22, 2011.
Taylor, Nick, "West to Add CZ Vials as Glass QC Issues Drive Interest", ttp://twitter.com/WestPharma/status/98804071674281986, 2 pages, retrieved from the internet Sep. 22, 2011.
Silicone Oil Layer, Contract Testing, webpage, http://www.siliconization.com/downloads/siliconeoillayercontracttesting.pdf, retrieved from the internet Oct. 28, 2011.
Patent Cooperation Treaty, Notification of Transmittal of International Preliminary Report on Patentability, in PCT/US2010/034577, dated Nov. 24, 2011.
Patent Cooperation Treaty, Notification of Transmittal of International Preliminary Report on Patentability, in PCT/US2010/034582, dated Nov. 24, 2011.
Patent Cooperation Treaty, Notification of Transmittal of International Preliminary Report on Patentability, in PCT/US2010/034586, dated Dec. 20, 2011.
Patent Cooperation Treaty, Notification of Transmittal of the International Search Report and the Written Opinion of the International Searching Authority, in PCT/US2011/036097, dated Dec. 29, 2011.
"Oxford instruments plasmalab 80plus", XP55015205, retrieved from the Internet on Dec. 20, 2011, URL:http://www.oxfordplasma.de/pdf_inst/plas_80.pdf.
Patent Cooperation Treaty, Notification of Transmittal of the International Search Report and the Written Opinion of the International Searching Authority, in PCT/US2011/044215, dated Dec. 29, 2011.
European Patent Office, Communication Pursuant to Article 94(3) EPC, in Application No. 10 162 758.6, dated May 8, 2012.
Patent Cooperation Treaty, International Preliminary Examining Authority, Notification of Transmittal of International Preliminary Report on Patentability, in international application No. PCT/US2011/036097, dated Nov. 13, 2012.
Patent Cooperation Treaty, Written Opinion of the International Searching Authority with International Search Report in Application No. PCT/US2012/064489, dated Jan. 25, 2013.
Danish Patent and Trademark Office, Singapore Written Opinion, in Application No. 201108308-6, dated Dec. 6, 2012.

(56) References Cited

OTHER PUBLICATIONS

Danish Patent and Trademark Office, Singapore Search Report, in Application No. 201108308-6, dated Dec. 12, 2012.
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029190.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.
Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www. WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL-100 ng/mL (40 fM-400 pM) Range, Department of Chemical Engineering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M in Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Parylene (12 pages).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.

Gibbins, Bruce and Warner, Lenna, The Role of Antimicrobial Silver Nanotechnology, Medical Device & Diagnostic Industry, Aug. 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24)9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 20, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.
State Intellectual Property Office of Teh People's Republic of China, Notification of First Office Action in Application No. 201080029201.4, dated Mar. 37, 2013. (15 pages).
Coating Syringes, http://www.triboglide.com/syringes.htm, printed Aug. 31, 2009.
Coating/Production Process, http://www.triboglide.com/process.htm, printed Aug. 31, 2009.
Munich Exp, Materialica 2005: Fundierte Einblicke in den Werkstofsektor, Seite 1, von 4, ME095-6.
Schott Developing Syringe Production in United States, Apr. 14, 2009, http://www.schott.com/pharmaceutical_packaging, printed Aug. 31, 2009.
Sterile Prefillable Glass and Polymer Syringes, Schott forma vitrum, http://www.schott.com/pharmaceutical_packaging.
Transparent und recyclingfähig, neue verpackung, Dec. 2002, pp. 54-57.
European Patent Office, Communication with European Search Report, in Application No. 10162758.6, dated Aug. 19, 2010.
Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.

(56) References Cited

OTHER PUBLICATIONS

Yang, et al., Microstructure and tribological properties of SiOx/DLC films grown by PECVD, Surface and Coatings Technology, vol. 194 (2005), Apr. 20, 2005, pp. 128-135.
European Patent Office, Communication with extended European search report, in Application No. EP10162756.0, dated Nov. 17, 2010.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.
European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, © The Royal Society of Chemistry, 2007.
Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.
Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.
Mallikarjunan, Anupama et al, The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).

Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
State Intellectual Property Office of the People's Republic of China, Notification of the Third Office Action, in Application No. 201080029201.4, dated Jul. 7, 2014 (15 pages).
Australian Government, IP Australia, Patent Examination Report No. 1, in Application No. 2011252925, dated Sep. 6, 2013 (3 pages).
PCT, Notification of Transmittal of the International Search Report and the Written Opinion of the International Searching Authority, or the Declaration, in International application No. PCT/US2013/040380, dated Sep. 3, 2013. (13 pages).
PCT, Notification of Transmittal of the International Search Report and the Written Opinion of the International Searching Authority, or the Declaration, in International application No. PCT/US2013/040368, dated Oct. 21, 2013. (21 pages).
PCT, Notification of Transmittal of the International Search Report and the Written Opinion of the International Searching Authority, or the Declaration, in International application No. PCT/US2013/048709, dated Oct. 2, 2013. (7 pages).
Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010, pp. 4012-4017, XPO27113381, ISSN: 0257-8972 [retrieved on Jun. 16, 2010] abstract, p. 4014, right-hand column-p. 4015, figures 2, 3.
Brunet-Bruneau A. et al., "Microstructural characterization of ion assisted Sio2 thin films by visible and infrared ellipsometry", Journal of Vacuum Science and Technology: Part A, AVS/AIP, Melville, NY, US, vol. 16, No. 4, Jul. 1, 1998, pp. 2281-2286, XPO12004127, ISSN: 0734-2101, DOI: 10.1116/1.581341, p. 2283, right-hand column-p. 2284, left-hand column, figures 2, 4.
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
Patent Cooperation Treaty, International Preliminary Examining Authority, Notification of Transmittal of International Preliminary Report on Patentability, in international application No. PCT/US2010/034571, dated Jun. 13, 2011.
Patent Cooperation Treaty, International Preliminary Examining Authority, Written Opinion of the International Preliminary Examining Authority, in international application No. PCT/US2010/034586, dated Aug. 23, 2011.
Patent Cooperation Treaty, International Preliminary Examining Authority, Written Opinion of the International Preliminary Examining Authority, in international application No. PCT/US2010/034568, dated May 30, 2011.
Hanlon, Adriene Lepiane, Pak, Chung K., Pawlikowski, Beverly A., Decision on Appeal, Appeal No. 2005-1693, U.S. Appl. No. 10/192,333, dated Sep. 30, 2005.
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.

(56) References Cited

OTHER PUBLICATIONS

PCT, Written Opinion of the International Preliminary Examining Authority, in International application No. PCT/US2013/071750, dated Jan. 20, 2015 (9 pages).
PCT, Written Opinion of the International Preliminary Examining Authority, in International application No. PCT/US2013/064121, dated Nov. 21, 2014 (7 pages).
Japanese Patent Office, Decision of Rejection in Application No. 2012-510983, dated Jan. 20, 2015 (4 pages).
Australian Government, IP Australia, Patent Examination Report No. 1, in Application No. 2010249033, dated Dec. 19, 2014 (7 pages).
Australian Government, IP Australia, Patent Examination Report No. 1, in Application No. 2011252925, dated Dec. 2, 2014 (3 pages).
Reh, et al., Evaluation of stationary phases for 2-dimensional HPLC of Proteins—Validation of commercial RP-columns, Published by Elsevier B.V., 2000.
State Intellectual Property Office of the People's Republic of China, Notification of the Fourth Office Action in Application No. 201080029199.0, dated Mar. 18, 2015 (15 pages).
Hlobik, Plastic Pre-Fillable Syringe Systems (http://www.healthcarepackaging.com/package-type/Containers/plastic-prefillablesyringe-systems, Jun. 8, 2010).
PCT, Written Opinion of the International Preliminary Examining Authority, International application No. PCT/SU2013/071752, dated May 6, 2015.
Hopwood J Ed—CRC Press: "Plasma-assisted deposition", Aug. 17, 1997, Handbook of Nanophase Materials, Chapter 6, pp. 141-197, XP008107730, ISBN: 978-0-8247-9469-9.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
US 5,645,643, 07/1997, Thomas (withdrawn)

* cited by examiner

VESSELS, CONTACT SURFACES, AND COATING AND INSPECTION APPARATUS AND METHODS

CROSS REFERENCE TO RELATED APPLICATIONS

This application claims the priority of U.S. Ser. No. 61/471,056, filed Apr. 1, 2011, which is incorporated here by reference in its entirety.

The following patent applications, publications, and patents are incorporated here by reference in their entirety.

| Application No. | Filing Date | Publication No. |
| --- | --- | --- |
| 61/177,984 | May 13, 2009 | |
| 61/222,727 | Jul. 2, 2009 | |
| 61/213,904 | Jul. 24, 2009 | |
| 61/234,505 | Aug. 17, 2009 | |
| 61/261,321 | Nov. 14, 2009 | |
| 61/263,275 | Nov. 20, 2009 | |
| 61/263,289 | Nov. 20, 2009 | |
| 61/285,813 | Dec. 11, 2009 | |
| 61/298,159 | Jan. 25, 2010 | |
| 61/299,888 | Jan. 29, 2010 | |
| 61/318,197 | Mar. 26, 2010 | |
| 61/333,625 | May 11, 2010 | |
| 12/779,077 | May 12, 2010 | U.S. Pat. No. 7,985,188 |
| EP10162755.2 | May 12, 2010 | EP2253735A2 |
| EP10162760.2 | May 12, 2010 | EP2251454A2 |
| EP10162757.8 | May 12, 2010 | EP2251453A2 |
| EP10162756.0 | May 12, 2010 | EP2251452A2 |
| EP10162758.6 | May 12, 2010 | EP2251671A2 |
| EP10162761.0 | May 12, 2010 | EP2251455A2 |
| PCT/US10/34568 | May 12, 2010 | WO 2010/132579 |
| PCT/US10/34571 | May 12, 2010 | WO 2010/132581 |
| PCT/US10/34576 | May 12, 2010 | WO 2010/132584 |
| PCT/US10/34577 | May 12, 2010 | WO 2010/132585 |
| PCT/US10/34582 | May 12, 2010 | WO 2010/132589 |
| PCT/US10/34586 | May 12, 2010 | WO/2010/132591 |
| 61/365,277 | Jul. 16, 2010 | |
| 61/371,967 | Aug. 9, 2010 | |
| 61/374,459 | Aug. 17, 2010 | |
| 61/379,299 | Sep. 21, 2010 | |
| 61/413,329 | Nov. 12, 2010 | |
| 61/413,334 | Nov. 12, 2010 | |
| 61/413,355 | Nov. 12, 2010 | |
| 61/413,340 | Nov. 12, 2010 | |
| 61/413,344 | Nov. 12, 2010 | |
| 61/413,347 | Nov. 12, 2010 | |
| 61/452,526 | Mar. 14, 2011 | |
| 61/452,518 | Mar. 14, 2011 | |

The present invention relates to the technical field of fabrication of coated contact surfaces of a medical device, for example a vessel and/or other device for storing or contacting biologically active compounds or body fluids. For example, the invention relates to a contact surface processing system for coating of a contact surface, a contact surface processing system for coating and inspection of a contact surface, a portable contact surface holder for a contact surface processing system, to a plasma enhanced chemical vapor deposition apparatus for coating a contact surface of a medical device, for example a vessel, to a method for coating an interior contact surface of a vessel, to a method for coating and inspection of a vessel or contact surface, to a method of processing a vessel or contact surface, to the use of a vessel or contact surface processing system, to a computer-readable medium and to a program element.

The present disclosure also relates to improved methods for processing medical devices, for example vessels, for example multiple identical vessels used for venipuncture and other medical sample collection, pharmaceutical preparation storage and delivery, and other purposes. Such vessels or contact surfaces are used in large numbers for these purposes, and must be relatively economical to manufacture and yet highly reliable in storage and use.

BACKGROUND OF THE INVENTION

Evacuated blood collection tubes are used for drawing blood from a patient for medical analysis. The tubes are sold evacuated. The patient's blood is communicated to the interior of a tube by inserting one end of a double-ended hypodermic needle into the patient's blood vessel and impaling the closure of the evacuated blood collection tube on the other end of the double-ended needle. The vacuum in the evacuated blood collection tube draws the blood (or more precisely, the blood pressure of the patient pushes the blood) through the needle into the evacuated blood collection tube, increasing the pressure within the tube and thus decreasing the pressure difference causing the blood to flow. The blood flow typically continues until the tube is removed from the needle or the pressure difference is too small to support flow.

Evacuated blood collection tubes should have a substantial shelf life to facilitate efficient and convenient distribution and storage of the tubes prior to use. For example, a one-year shelf life is desirable, and progressively longer shelf lives, such as 18 months, 24 months, or 36 months, are also desired in some instances. The tube desirably remains essentially fully evacuated, at least to the degree necessary to draw enough blood for analysis (a common standard is that the tube retains at least 90% of the original draw volume), for the full shelf life, with very few (optimally no) defective tubes being provided.

A defective tube is likely to cause the phlebotomist using the tube to fail to draw sufficient blood. The phlebotomist might then need to obtain and use one or more additional tubes to obtain an adequate blood sample.

Prefilled syringes are commonly prepared and sold so the syringe does not need to be filled before use. The syringe can be prefilled with saline solution, a dye for injection, or a pharmaceutically active preparation, for some examples.

Commonly, the prefilled syringe is capped at the distal end, as with a cap, and is closed at the proximal end by its drawn plunger. The prefilled syringe can be wrapped in a sterile package before use. To use the prefilled syringe, the packaging and cap are removed, optionally a hypodermic needle or another delivery conduit is attached to the distal end of the barrel, the delivery conduit or syringe is moved to a use position (such as by inserting the hypodermic needle into a patient's blood vessel or into apparatus to be rinsed with the contents of the syringe), and the plunger is advanced in the barrel to inject the contents of the barrel.

One important consideration in manufacturing pre-filled syringes is that the contents of the syringe desirably will have a substantial shelf life, during which it is important to isolate the material filling the syringe from the barrel wall containing it, to avoid leaching material from the barrel into the prefilled contents or vice versa.

Since many of these vessels or contact surfaces are inexpensive and used in large quantities, for certain applications it will be useful to reliably obtain the necessary shelf life without increasing the manufacturing cost to a prohibitive level. It is also desirable for certain applications to move away from glass vessels or contact surfaces, which can break and are expensive to manufacture, in favor of plastic vessels or contact surfaces which are rarely broken in normal use (and if broken do not form sharp shards from remnants of the vessel, like a glass tube would). Glass vessels have been favored because glass is more gas tight and inert to pre-filled contents than untreated plastics. Also, due to its traditional use, glass is well accepted, as it is known to be relatively innocuous when contacted with medical samples or pharmaceutical preparations and the like.

A further consideration when regarding syringes is to ensure that the plunger can move at a constant speed and with a constant force when it is pressed into the barrel. For this purpose, a lubricity layer, either on one or on both of the barrel and the plunger, is desirable.

Similar considerations apply for other medical devices, particularly those used in contact with a patient's tissue or body fluids, either in vivo or in vitro. Many such devices have surfaces that require a barrier coating, lubricity, and/or a surface characteristic compatible with body fluids and tissues.

SUMMARY OF THE INVENTION

An aspect of the present invention is a medical device comprising a substrate defining a contact surface and a lubricity layer deposited on the contact surface. The contact surface is a point or area of contact between the substrate and a fluid or tissue when the medical device is in use. The lubricity layer is deposited on the contact surface and configured to provide a lower sliding force or breakout force for the contact surface than for the uncoated substrate.

The lubricity layer has one of the following atomic ratios, measured by X-ray photoelectron spectroscopy (XPS), $Si_wO_xC_y$ or $Si_wN_xC_y$, where w is 1, x in this formula is from about 0.5 to 2.4, and y is from about 0.6 to about 3. The lubricity layer has a thickness by transmission electron microscopy (TEM) between 10 and 1000 nm. The lubricity layer deposited by plasma enhanced chemical vapor deposition (PECVD) under conditions effective to form a coating from a precursor. The precursor is selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

Another aspect of the invention is a medical device comprising a substrate defining a contact surface as defined above and a barrier layer deposited on the contact surface. The barrier layer is configured to reduce the transmission of a fluid to or from the contact surface.

The barrier layer has one of the following atomic ratios, measured by X-ray photoelectron spectroscopy (XPS), $SiO_x$ or $SiN_x$, where x is from about 0.5 to 2.4. The barrier layer has a thickness by transmission electron microscopy (TEM) between 1 and 1000 nm. The barrier layer is deposited by plasma enhanced chemical vapor deposition (PECVD) under conditions effective to form a coating from a precursor. As defined above.

Still another aspect of the invention is a medical device comprising contact surface as previously defined. The contact surface is a hydrophobic layer having the composition: $SiO_xC_y$ or $SiN_xC_y$, where x in this formula is from about 0.5 to 2.4 and y is from about 0.6 to about 3. The contact surface is of the type made by providing a precursor as defined above, applying the precursor to a contact surface, and polymerizing or crosslinking the coating, or both, to form a hydrophobic contact surface having a higher contact angle than the untreated contact surface.

Figure 1:
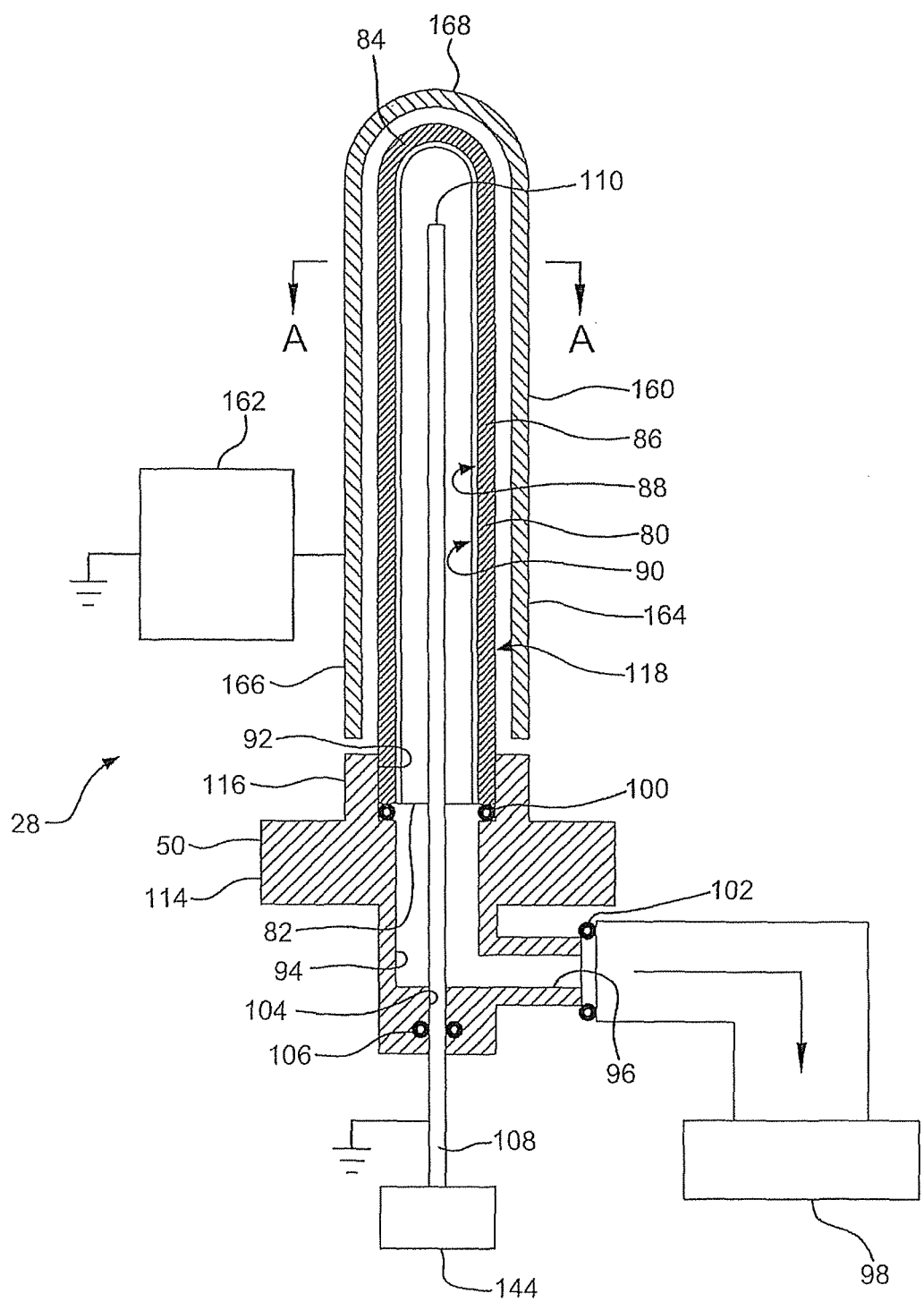
FIG. 1 is a schematic sectional view of a vessel holder in a coating station according to an embodiment of the disclosure.
Figure 6:
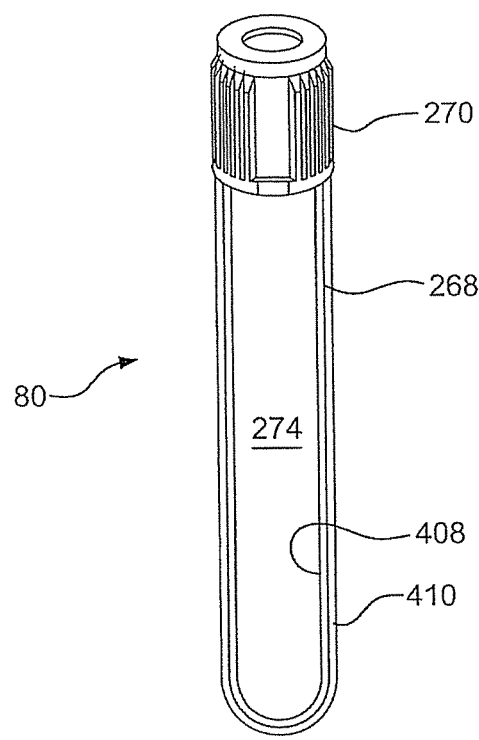
FIG. 6 is a perspective view of a double-walled blood collection tube assembly according to still another embodiment of the invention.

The following reference characters are used in the drawing figures:

| | |
|---|---|
| 28 | Coating station |
| 80 | Vessel |
| 82 | Opening |
| 84 | Closed end |
| 86 | Wall |
| 88 | Interior contact surface |
| 90 | Barrier layer |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (counter electrode) |
| 110 | Gas delivery port (of 108) |
| 114 | Housing (of 50 or 112) |
| 116 | Collar |
| 118 | Exterior contact surface (of 80) |
| 144 | PECVD gas source |
| 160 | Electrode |
| 162 | Power supply |
| 164 | Sidewall (of 160) |
| 166 | Sidewall (of 160) |
| 168 | Closed end (of 160) |
| 80 | Vessel |
| 84 | Closed end |
| 250 | Syringe barrel |
| 252 | Syringe |
| 254 | Interior contact surface (of 250) |
| 256 | Back end (of 250) |
| 258 | Plunger (of 252) |
| 260 | Front end (of 250) |
| 262 | Cap |
| 264 | Interior contact surface (of 262) |
| 268 | Vessel |
| 270 | Closure |
| 272 | Interior facing contact surface |
| 274 | Lumen |
| 276 | Wall-contacting contact surface |
| 278 | Inner contact surface (of 280) |
| 280 | Vessel wall |
| 282 | Stopper |
| 284 | Shield |
| 286 | Lubricity layer |
| 288 | Barrier layer |
| 408 | Inner wall (FIG. 6) |
| 410 | Outer wall (FIG. 6) |
| 412 | Interior contact surface (FIG. 6) |

DETAILED DESCRIPTION OF THE PREFERRED EMBODIMENTS

The present invention will now be described more fully with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout.

DEFINITION SECTION

In the context of the present invention, the following definitions and abbreviations are used:

RF is radio frequency; sccm is standard cubic centimeters per minute.

The term "at least" in the context of the present invention means "equal or more" than the integer following the term. The word "comprising" does not exclude other elements or steps, and the indefinite article "a" or "an" does not exclude a plurality unless indicated otherwise.

"First" and "second" or similar references to, e.g., processing stations or processing devices refer to the minimum number of processing stations or devices that are present, but do not necessarily represent the order or total number of processing stations and devices. These terms do not limit the number of processing stations or the particular processing carried out at the respective stations.

For purposes of the present invention, an "organosilicon precursor" is a compound having at least one of the linkage:

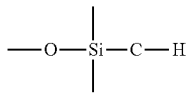

which is a tetravalent silicon atom connected to an oxygen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

In the context of the present invention, "essentially no oxygen" or (synonymously) "substantially no oxygen" is added to the gaseous reactant in some embodiments. This means that some residual atmospheric oxygen can be present in the reaction space, and residual oxygen fed in a previous step and not fully exhausted can be present in the reaction space, which are defined here as essentially no oxygen present. Essentially no oxygen is present in the gaseous reactant if the gaseous reactant comprises less than 1 vol. % $O_2$, for example less than 0.5 vol. % $O_2$, and optionally is $O_2$-free. If no oxygen is added to the gaseous reactant, or if no oxygen at all is present during PECVD, this is also within the scope of "essentially no oxygen."

A "vessel" in the context of the present invention is a subset exemplary of the broader set of medical devices as defined herein. A vessel per se can be any type of article that is adapted to contain or convey a material. The material can be a liquid, a gas, a solid, or any two or more of these. One example of a vessel is an article with at least one opening and a wall defining an interior contact surface. Optionally, at least a portion of the interior contact surface defines a "contact surface" which is treated according to the present disclosure. The term "at least" in the context of the present invention means "equal or more" than the integer following the term. Thus, a vessel in the context of the present invention has one or more openings.

One or two openings, like the openings of a sample tube (one opening) or a syringe barrel (two openings) are preferred. If the vessel has two or more openings, they can be of same or different size. If there is more than one opening, one opening can be used for the gas inlet for a PECVD coating method according to the present invention, while the other openings are either capped or open.

A vessel according to the present invention can be a sample tube, e.g. for collecting or storing biological fluids like blood or urine, a syringe (or a part thereof, for example a syringe barrel) for storing or delivering a biologically active compound or composition, e.g. a medicament or pharmaceutical composition, a vial for storing biological materials or biologically active compounds or compositions, a pipe, e.g. a catheter for transporting biological materials or biologically active compounds or compositions, or a cuvette for holding fluids, e.g. for holding biological materials or biologically active compounds or compositions.

A vessel can be of any shape. One example of a vessel has a substantially cylindrical wall adjacent to at least one of its open ends. Generally, the interior wall of a vessel of this type is cylindrically shaped, like, e.g. in a sample tube or a syringe barrel. Sample tubes and syringes or their parts (for example syringe barrels), vials, and petri dishes, which commonly are generally cylindrical, are contemplated.

Some other non-limiting examples of contemplated vessels include well or non-well slides or plates, for example titer plates or microtiter plates. Still other non-limiting examples of contemplated vessels include pump contact surfaces in contact with the pumped material, including impeller contact surfaces, pump chamber contact surfaces and the like. Even other non-limiting examples of contemplated vessels include parts of an fluid containment, pumping, processing, filtering, and delivery system, such as an intravenous fluid delivery system, a blood processing system (such as a heart-lung machine or a blood component separator) a dialysis system, or an insulin delivery system, as several examples. Examples of such vessel parts are tubing, pump interior contact surfaces, drug or saline containing bags or bottles, adapters and tubing connectors for connecting parts of the system together, intravenous needles and needle assemblies, membranes and filters, etc. Other examples of vessels include measuring and delivery devices such as pipettes.

The invention has more general application to "contact surfaces" of medical devices and the like used or usable in contact with human or animal fluids or tissues, whether or not associated with a vessel. Some additional non-limiting examples of devices having contact surfaces are devices inserted in an orifice, through the skin, or otherwise within the body of a human or animal, such as thermometers, probes, guidewires, catheters, electrical leads, surgical drains, pacemakers, defibrillators, orthopedic devices such as screws, plates, and rods, clothing, face masks, eye shields, and other equipment worn by medical personnel, surgical drapes, sheet or fabric material used to make the same, surgical instruments such as saws and saw blades, drills and drill bits, etc.

The invention further has application to any contact surfaces of devices used or usable in contact with pharmaceutical preparations or other materials, such as ampoules, vials, syringes, bottles, bags, or other containment vessels, stirring rods, impellers, stirring pellets, etc., also within the definition of "contact surfaces."

Some specific medical devices having fluid or tissue contacting surfaces that can be treated according to the present disclosure follow:

ACL/PCL Reconstruction Systems
Adapters
Adhesion barriers
Agar Petri dishes
Anesthesia units
Anesthesia ventilators
Angiographic Catheter
Ankle replacements
Aortic valve replacement
Apnea monitors
Applicators
Argon enhanced coagulation units
Artificial facet replacement
Artificial heart
Artificial heart valve
Artificial organ
Artificial pacemaker
Artificial pancreas
Artificial urinary bladder
Aspirators
Aspirators
Atherectomy Catheter
Auditory brainstem implant
Auto transfusion units
Bags
Balloon Catheter
Bare-metal stent
Beakers
bileaflet valves
Biliary Stent
Bio implants
Bioceramic devices
Bioresorbable stents
Biphasic Cuirass Ventilation
Blood Culture devices
Blood sample cassettes
Blood Sampling Systems
Bottles
Brain implant
Breast implant
Breast pumps
Buccal sample cassettes
Buttock augmentation
Caged-ball valves
Cannulated Screws
Capillary Blood Collection devices
Capsular contracture
Cardiac Catheter
Cardiac Catheter
Cardiac defibrillator, external or internal
Cardiac Output Injectate Kits & Cables
Cardiac prostheses
Cardiac shunt
Catheters
Cell lifters
Cell scrapers
Cell spreaders
Central Venous Catheter
Centrifuge components
Cerebral shunt
CHD Stent
Chemical transfer pumps
Chin augmentation
Chin sling
Cochlear implant
Collection and Transport devices
Colonic Stent
Compression pump
Connectors
Containers
Contraceptive implants
cornea implants
Coronary stents
Cotrel-Dubousset instrumentation
Cover glasses
Cranio Maxillofacial Implants
Cryo/Freezer boxes
Dehydrated Culture Media devices
Deltec Cozmo
Dental implants
Depression microscopic slides
Dewar flasks
DHS/DCS & Angled Blade Plates
Diabetes accessories
Diaphragm pumps
Diaphragmatic pacemaker
Direct Testing and Serology devices
Disposable Domes and Kits
Double Channel Catheter
Double-Lumen Catheter
Drug-Eluting Stents
Duodenal Stent
Dynamic compression plate
Dynamic hip screw
Elastomeric pump
Elbow replacements
Elbowed Catheter
Electrocardiograph (ECG)
Electrode Catheter
Electroencephalograph (EEG)
Electronic thermometer
Electrosurgical units
Endoscopes
Enteral feeding pumps
Environmental Systems devices
Esophageal stent
External Fixators
External pacemaker
Female Catheter
Fetal monitors
Films
Flat microscopic slides
Flow-restricted, oxygen-powered ventilation device
Fluid Administration Products
Fluid-Filled Catheter
Foley Catheter
Forceps
Glaucoma valve
Goggles
Gouley Catheter
grafts
Grommets
Gruentzig Balloon Catheter
Harrington rod
Heart valves
Heart-lung machine
HeartMate left ventricular assist device
Hip Prosthesis
Hip replacements
Hip resurfacing
Holders Human-implantable RFID chips
Hypoxicator
Identification and Susceptibility devices
Implanon
Implant (medicine)
Implantable cardioverter-defibrillator
Implantable defibrilators
Implantable Devices
Implantable Gastric Stimulation
Incubators
Incubators
In-Dwelling Catheter
Infusion Sets
Inhaler
Insulin pen
Insulin pump
Insulin pumps
Interlocking Nail
Internal fixation
Intra-aortic balloon pump
Intramedullary rod
Intrathecal pump
Intrathecal pump
Intravenous Catheter
Invasive blood pressure units
Iron lung
IV Adapters
IV Catheters
IV Connectors
IV Flush Syringes
IV Products
IV Site Maintenance devices
IV Stopcocks
Joint replacement of the hand
Joint replacements
Keratometer
Kirschner wire
Knee cartilage replacement therapy
Knee replacements
Lancets
Laparoscopic insufflators
Large Fragment Implants
Lensometer
Liquid ventilator
Lytic bacteriophages
Medical grafting
Medical Pumps
Medical ventilator
Microbiology Equipment and Supplies
Microbiology Testing devices
Microchip implant (human)
Microscopic Slides
Microtiter plates
Midline Catheter
Mini dental implants
Mini Fragment Implants
Minimplants
Molecular Diagnostics devices
Mycobacteria Testing devices
Nails, Wires & Pins
Needleless IV Connectors
Nelaton urinary catheter
Norplant implantable birth control device
O'Neil Aspirating and Irrigating Needle
O'Neil Balloon Infuser
O'Neil Intermittent urinary catheter
Orthopedic implants
Osseointegration implant
Oxinium replacement joint material
Pacemakers
Pacing Catheter
Pain management pumps
Palatal obturator
Pancreatic Stent
Penile prosthesis
Penis enlargement device
Peripheral stents
Peripherally Inserted Central Catheter (PICC)
Peristaltic pumps
Peritoneovenous shunt
Petri dishes
Phonocardiographs
Phototherapy units
Pipettes
Polyaxial screw
Port (medical)
Portacaval shunt
Positive airway pressure device
Prepared Media devices
Pressure Accessories and Cables
Pressure Transducers
Prostatic Catheter
Prostatic stents
Pulmonary Artery Catheters
Pulse oximeters
radiant warmers
Radiation-therapy machines
Razor Blades
re-constructive prosthesis
Right-to-left shunt
Sacral nerve stimulator
Safety Supplies
Sample collection containers
Sample collection tubes
Sample Collection/Storage Devices
Self-expandable metallic stent
Self-Retaining Catheter
Shaker flasks
Shoulder replacements
Shunt (medical)
skin implants
Small Fragment Implants
Snare Catheter
Sphygmomanometers
Spinal Cord Stimulator
Spine Surgery
Stains and Reagents
Static Control Supplies
Stent grafts
Stents
Sterility Supplies
Sterilizers
Stirrers
Subdermal implant
Surgical drill and saws
Surgical microscope
sutures
Swabs
Swan-Ganz Catheter
Syringe driver
Temperature monitor
Tenckhoff Catheter
Tiemann Catheter
tilting-disk valves Tissue grinders
Toposcopic Catheter
Transdermal implant
Tubing
Tubing links
Two-Way Catheter
Ultrasonic nebulizers
Ultrasound sensors
Unicompartmental knee arthroplasty
Ureteral Catheter
Ureteral stents
Urethral Catheter
Urinary Catheter
Urine sample cassettes
Vascular ring connector
Vascular stents
Ventilator
Ventricular assist device
Vertebral fixation
Winged Catheter
X-ray diagnostic equipment A "hydrophobic layer" in the context of the present invention means that the coating lowers the wetting tension of a contact surface coated with the coating, compared to the corresponding uncoated contact surface. Hydrophobicity is thus a function of both the uncoated substrate and the coating. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity, and optionally can have a composition according to the empirical composition or sum formula $Si_wO_xC_yH_z$, for example where w is 1, x is from about 0.5 to about 2.4, y is from about 0.6 to about 3, and z is from about 2 to about 9, optionally where w is 1, x is from about 0.5 to 1, y is from about 2 to about 3, and z is from 6 to about 9. These values of w, x, y, and z are applicable to the empirical composition $Si_wO_xC_yH_z$ throughout this specification. The values of w, x, y, and z used throughout this specification should be understood as ratios or an empirical formula (e.g. for a coating), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$.

"Wetting tension" is a specific measure for the hydrophobicity or hydrophilicity of a contact surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film contact surface for exactly two seconds. This is the film's wetting tension. The procedure utilized is varied herein from ASTM D 2578 in that the substrates are not flat plastic films, but are tubes made according to the Protocol for Forming PET Tube and (except for controls) coated according to the Protocol for Coating Tube Interior with Hydrophobic Layer (see Example 8).

A "lubricity layer" according to the present invention is a coating which has a lower frictional resistance than the uncoated contact surface. In other words, it reduces the frictional resistance of the coated contact surface in comparison to a reference contact surface which is uncoated. The present lubricity layers are primarily defined by their lower frictional resistance than the uncoated contact surface and the process conditions providing lower frictional resistance than the uncoated contact surface, and optionally can have a composition according to the empirical composition $Si_wO_xC_yH_z$, as defined in this Definition Section. "Frictional resistance" can be static frictional resistance and/or kinetic frictional resistance. One of the optional embodiments of the present invention is a syringe part, e.g. a syringe barrel or plunger, coated with a lubricity layer. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity characteristics of a lubricity layer in the context of the present invention whenever the coating is applied to any syringe or syringe part, for example to the inner wall of a syringe barrel. The breakout force is of particular relevance for evaluation of the coating effect on a prefilled syringe, i.e. a syringe which is filled after coating and can be stored for some time, e.g. several months or even years, before the plunger is moved again (has to be "broken out").

The "plunger sliding force" in the context of the present invention is the force required to maintain movement of a plunger in a syringe barrel, e.g. during aspiration or dispense. It can advantageously be determined using the ISO 7886-1: 1993 test described herein and known in the art. A synonym for "plunger sliding force" often used in the art is "plunger force" or "pushing force".

The "breakout force" in the context of the present invention is the initial force required to move the plunger in a syringe, for example in a prefilled syringe.

Both "plunger sliding force" and "breakout force" and methods for their measurement are described in more detail in subsequent parts of this description.

"Slidably" means that the plunger is permitted to slide in a syringe barrel.

In the context of this invention, "substantially rigid" means that the assembled components (ports, duct, and housing, explained further below) can be moved as a unit by handling the housing, without significant displacement of any of the assembled components respecting the others. Specifically, none of the components are connected by hoses or the like that allow substantial relative movement among the parts in normal use. The provision of a substantially rigid relation of these parts allows the location of the vessel seated on the vessel holder to be nearly as well known and precise as the locations of these parts secured to the housing In the following, the apparatus for performing the present invention will be described first, followed by the coating methods, coatings and coated vessels, and the uses according to the present invention.

Various aspects of:
 vessel processing systems and equipment;
 methods for transporting vessels—processing vessels seated on vessel holders;
 PECVD apparatus for making vessels;
 PECVD methods for making vessels; and
 vessel inspection
are described in detail in U.S. Pat. No. 7,985,188 incorporated by reference above.

VII. PECVD Treated Vessels

VII. Vessels are contemplated having a barrier coating 90 (shown in FIG. 1, for example), which can be an $SiO_x$ coating applied to a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The coating can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated. The thickness of the $SiO_x$ or other coating can be measured, for example, by transmission electron microscopy (TEM), and its composition can be measured by X-ray photoelectron spectroscopy (XPS).

VII. It is contemplated that the choice of the material to be barred from permeating the coating and the nature of the $SiO_x$ coating applied can affect its barrier efficacy. For example, two examples of material commonly intended to be barred are oxygen and water/water vapor. Materials commonly are a better barrier to one than to the other. This is believed to be so at least in part because oxygen is transmitted through the coating by a different mechanism than water is transmitted.

VII. Oxygen transmission is affected by the physical features of the coating, such as its thickness, the presence of cracks, and other physical details of the coating. Water transmission, on the other hand, is believed to commonly be affected by chemical factors, i.e. the material of which the coating is made, more than physical factors. The inventors also believe that at least one of these chemical factors is a substantial concentration of OH moieties in the coating, which leads to a higher transmission rate of water through the barrier. An $SiO_x$ coating often contains OH moieties, and thus a physically sound coating containing a high proportion of OH moieties is a better barrier to oxygen than to water. A physically sound carbon-based barrier, such as amorphous carbon or diamond-like carbon (DLC) commonly is a better barrier to water than is a $SiO_x$ coating because the carbon-based barrier more commonly has a lower concentration of OH moieties.

VII. Other factors lead to a preference for an $SiO_x$ coating, however, such as its oxygen barrier efficacy and its close chemical resemblance to glass and quartz. Glass and quartz (when used as the base material of a vessel) are two materials long known to present a very high barrier to oxygen and water transmission as well as substantial inertness to many materials commonly carried in vessels. Thus, it is commonly desirable to optimize the water barrier properties such as the water vapor transmission rate (WVTR) of an $SiO_x$ coating, rather than choosing a different or additional type of coating to serve as a water transmission barrier.

VII. Several ways contemplated to improve the WVTR of an $SiO_x$ coating are as follow.

VII. The concentration ratio of organic moieties (carbon and hydrogen compounds) to OH moieties in the deposited coating can be increased. This can be done, for example, by increasing the proportion of oxygen in the feed gases (as by increasing the oxygen feed rate or by lowering the feed rate of one or more other constituents). The lowered incidence of OH moieties is believed to result from increasing the degree of reaction of the oxygen feed with the hydrogen in the silicone source to yield more volatile water in the PECVD exhaust and a lower concentration of OH moieties trapped or incorporated in the coating.

VII. Higher energy can be applied in the PECVD process, either by raising the plasma generation power level, by applying the power for a longer period, or both. An increase in the applied energy must be employed with care when used to coat a plastic tube or other device, as it also has a tendency to distort the vessel being treated, to the extent the tube absorbs the plasma generation power. This is why RF power is contemplated in the context of present application. Distortion of the medical devices can be reduced or eliminated by employing the energy in a series of two or more pulses separated by cooling time, by cooling the vessels while applying energy, by applying the coating in a shorter time (commonly thus making it thinner), by selecting a frequency of the applied coating that is absorbed minimally by the base material selected for being coated, and/or by applying more than one coating, with time in between the respective energy application steps. For example, high power pulsing can be used with a duty cycle of 1 millisecond on, 99 milliseconds off, while continuing to feed the process gas. The process gas is then the coolant, as it keeps flowing between pulses. Another alternative is to reconfigure the power applicator, as by adding magnets to confine the plasma increase the effective power application (the power that actually results in incremental coating, as opposed to waste power that results in heating or unwanted coating). This expedient results in the application of more coating-formation energy per total Watt-hour of energy applied. See for example U.S. Pat. No. 5,904,952.

VII. An oxygen post-treatment of the coating can be applied to remove OH moieties from the previously-deposited coating. This treatment is also contemplated to remove residual volatile organosilicon compounds or silicones or oxidize the coating to form additional $SiO_x$.

VII. The plastic base material tube can be preheated.

VII. A different volatile source of silicon, such as hexamethyldisilazane (HMDZ), can be used as part or all of the silicone feed. It is contemplated that changing the feed gas to HMDZ will address the problem because this compound has no oxygen moieties in it, as supplied. It is contemplated that one source of OH moieties in the HMDSO-sourced coating is hydrogenation of at least some of the oxygen atoms present in unreacted HMDSO.

VII. A composite coating can be used, such as a carbon-based coating combined with $SiO_x$. This can be done, for example, by changing the reaction conditions or by adding a substituted or unsubstituted hydrocarbon, such as an alkane, alkene, or alkyne, to the feed gas as well as an organosilicon-based compound. See for example U.S. Pat. No. 5,904,952, which states in relevant part: "For example, inclusion of a lower hydrocarbon such as propylene provides carbon moieties and improves most properties of the deposited films (except for light transmission), and bonding analysis indicates the film to be silicon dioxide in nature. Use of methane, methanol, or acetylene, however, produces films that are silicone in nature. The inclusion of a minor amount of gaseous nitrogen to the gas stream provides nitrogen moieties in the deposited films and increases the deposition rate, improves the transmission and reflection optical properties on glass, and varies the index of refraction in response to varied amounts of $N_2$. The addition of nitrous oxide to the gas stream increases the deposition rate and improves the optical properties, but tends to decrease the film hardness."

VII. A diamond-like carbon (DLC) coating can be formed as the primary or sole coating deposited. This can be done, for example, by changing the reaction conditions or by feeding methane, hydrogen, and helium to a PECVD process. These reaction feeds have no oxygen, so no OH moieties can be formed. For one example, an $SiO_x$ coating can be applied on the interior of a tube or syringe barrel and an outer DLC coating can be applied on the exterior contact surface of a tube or syringe barrel. Or, the $SiO_x$ and DLC coatings can both be applied as a single layer or plural layers of an interior tube or syringe barrel coating.

VII. Referring to FIG. 1, the barrier or other type of coating 90 reduces the transmission of atmospheric gases into the vessel 80 through its interior contact surface 88. Or, the barrier or other type of coating 90 reduces the contact of the contents of the vessel 80 with the interior contact surface 88. The barrier or other type of coating can comprise, for example, $SiO_x$, amorphous (for example, diamond-like) carbon, or a combination of these.

VII. Any coating described herein can be used for coating a contact surface, for example a plastic contact surface. It can further be used as a barrier layer, for example as a barrier against a gas or liquid, optionally against water vapor, oxygen and/or air. It can also be used for preventing or reducing mechanical and/or chemical effects which the coated contact surface would have on a compound or composition if the contact surface were uncoated. For example, it can prevent or reduce the precipitation of a compound or composition, for example insulin precipitation or blood clotting or platelet activation.

VII.A. Evacuated Blood Collection Vessels
VII.A.1. Tubes

VII.A.I. Referring to FIG. 1, more details of the vessel such as 80 are shown. The illustrated vessel 80 can be generally tubular, having an opening 82 at one end of the vessel, opposed by a closed end 84. The vessel 80 also has a wall 86 defining an interior contact surface 88. One example of the vessel 80 is a medical sample tube, such as an evacuated blood collection tube, as commonly is used by a phlebotomist for receiving a venipuncture sample of a patient's blood for use in a medical laboratory.

VII.A.1. The vessel 80 can be made, for example, of thermoplastic material. Some examples of suitable thermoplastic material are polyethylene terephthalate or a polyolefin such as polypropylene or a cyclic polyolefin copolymer.

VII.A.1. The vessel 80 can be made by any suitable method, such as by injection molding, by blow molding, by machining, by fabrication from tubing stock, or by other suitable means. PECVD can be used to form a coating on the internal contact surface of $SiO_x$.

VII.A.1. If intended for use as an evacuated blood collection tube, the vessel 80 desirably can be strong enough to withstand a substantially total internal vacuum substantially without deformation when exposed to an external pressure of 760 Torr or atmospheric pressure and other coating processing conditions. This property can be provided, in a thermoplastic vessel 80, by providing a vessel 80 made of suitable materials having suitable dimensions and a glass transition temperature higher than the processing temperature of the coating process, for example a cylindrical wall 86 having sufficient wall thickness for its diameter and material.

VII.A.1. Medical vessels or containers like sample collection tubes and syringes are relatively small and are injection molded with relatively thick walls, which renders them able to be evacuated without being crushed by the ambient atmospheric pressure. They are thus stronger than carbonated soft drink bottles or other larger or thinner-walled plastic containers. Since sample collection tubes designed for use as evacuated vessels typically are constructed to withstand a full vacuum during storage, they can be used as vacuum chambers.

VII.A.1. Such adaptation of the vessels to be their own vacuum chambers might eliminate the need to place the vessels into a vacuum chamber for PECVD treatment, which typically is carried out at very low pressure. The use of a vessel as its own vacuum chamber can result in faster processing time (since loading and unloading of the parts from a separate vacuum chamber is not necessary) and can lead to simplified equipment configurations. Furthermore, a vessel holder is contemplated, for certain embodiments, that will hold the device (for alignment to gas tubes and other apparatus), seal the device (so that the vacuum can be created by attaching the vessel holder to a vacuum pump) and move the device between molding and subsequent processing steps.

VII.A.1. A vessel 80 used as an evacuated blood collection tube should be able to withstand external atmospheric pressure, while internally evacuated to a reduced pressure useful for the intended application, without a substantial volume of air or other atmospheric gas leaking into the tube (as by bypassing the closure) or permeating through the wall 86 during its shelf life. If the as-molded vessel 80 cannot meet this requirement, it can be processed by coating the interior contact surface 88 with a barrier or other type of coating 90. It is desirable to treat and/or coat the interior contact surfaces of these devices (such as sample collection tubes and syringe barrels) to impart various properties that will offer advantages over existing polymeric devices and/or to mimic existing glass products. It is also desirable to measure various properties of the devices before and/or after treatment or coating.

VII.A.1.a. Coating Deposited from an Organosilicon Precursor Made by In Situ Polymerizing Organosilicon Precursor VII.A.1.a. A process is contemplated for applying a lubricity layer characterized as defined in the Definition Section on a substrate, for example the interior of the barrel of a syringe, comprising applying one of the described precursors on or in the vicinity of a substrate at a thickness of 1 to 5000 nm, optionally 10 to 1000 nm, optionally 10-200 nm, optionally 20 to 100 nm thick and crosslinking or polymerizing (or both) the coating, optionally in a PECVD process, to provide a lubricated contact surface. The coating applied by this process is also contemplated to be new.

VII.A.1.a. A coating of $Si_wO_xC_yH_z$ as defined in the Definition Section can have utility as a hydrophobic layer. Coatings of this kind are contemplated to be hydrophobic, independent of whether they function as lubricity layers. A coating or treatment is defined as "hydrophobic" if it lowers the wetting tension of a contact surface, compared to the corresponding uncoated or untreated contact surface. Hydrophobicity is thus a function of both the untreated substrate and the treatment.

VII.A.1.a. The degree of hydrophobicity of a coating can be varied by varying its composition, properties, or deposition method. For example, a coating of $SiO_x$ having little or no hydrocarbon content is more hydrophilic than a coating of $Si_wO_xC_yH_z$ as defined in the Definition Section. Generally speaking, the higher the C—$H_x$ (e.g. CH, $CH_2$, or $CH_3$) moiety content of the coating, either by weight, volume, or molarity, relative to its silicon content, the more hydrophobic the coating.

VII.A.1.a. A hydrophobic layer can be very thin, having a thickness of at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The coating can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated.

VII.A.1.a. One utility for such a hydrophobic layer is to isolate a thermoplastic tube wall, made for example of polyethylene terephthalate (PET), from blood collected within the tube. The hydrophobic layer can be applied on top of a hydrophilic $SiO_x$ coating on the internal contact surface of the tube. The $SiO_x$ coating increases the barrier properties of the thermoplastic tube and the hydrophobic layer changes the contact surface energy of blood contact surface with the tube wall. The hydrophobic layer can be made by providing a precursor selected from those identified in this specification. For example, the hydrophobic layer precursor can comprise hexamethyldisiloxane (HMDSO) or octamethylcyclotetrasiloxane (OMCTS).

VII.A.1.a. Another use for a hydrophobic layer is to prepare a glass cell preparation tube. The tube has a wall defining a lumen, a hydrophobic layer in the internal contact surface of the glass wall, and contains a citrate reagent. The hydrophobic layer can be made by providing a precursor selected from those identified elsewhere in this specification. For another example, the hydrophobic layer precursor can comprise hexamethyldisiloxane (HMDSO) or octamethylcyclotetrasiloxane (OMCTS). Another source material for hydrophobic layers is an alkyl trimethoxysilane of the formula:

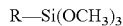

in which R is a hydrogen atom or an organic substituent, for example methyl, ethyl, propyl, isopropyl, butyl, isobutyl, t-butyl, vinyl, alkyne, epoxide, or others. Combinations of two or more of these are also contemplated.

VII.A.1.a. Combinations of acid or base catalysis and heating, using an alkyl trimethoxysilane precursor as described above, can condense the precursor (removing ROH by-products) to form crosslinked polymers, which can optionally be further crosslinked via an alternative method. One specific example is by Shimojima et. al. J. Mater. Chem., 2007, 17, 658-663.

VII.A.1.a. A lubricity layer, characterized as defined in the Definition Section, can be applied as a subsequent coating after applying an $SiO_x$ barrier coating to the interior contact surface 88 of the vessel 80 to provide a lubricity layer, particularly if the lubricity layer is a liquid organosiloxane compound at the end of the coating process.

VII.A.1.a. Optionally, after the lubricity layer is applied, it can be post-cured after the PECVD process. Radiation curing approaches, including UV-initiated (free radial or cationic), electron-beam (E-beam), and thermal as described in Development Of Novel Cycloaliphatic Siloxanes For Thermal And UV-Curable Applications (Ruby Chakraborty Dissertation, can 2008) be utilized.

VII.A.1.a. Another approach for providing a lubricity layer is to use a silicone demolding agent when injection-molding the thermoplastic vessel to be lubricated. For example, it is contemplated that any of the demolding agents and latent monomers causing in-situ thermal lubricity layer formation during the molding process can be used. Or, the aforementioned monomers can be doped into traditional demolding agents to accomplish the same result.

VII.A.1.a. A lubricity layer, characterized as defined in the Definition Section, is particularly contemplated for the internal contact surface of a syringe barrel as further described below. A lubricated internal contact surface of a syringe barrel can reduce the plunger sliding force needed to advance a plunger in the barrel during operation of a syringe, or the breakout force to start a plunger moving after the prefilled syringe plunger has pushed away the intervening lubricant or adhered to the barrel, for example due to decomposition of the lubricant between the plunger and the barrel. As explained elsewhere in this specification, a lubricity layer also can be applied to the interior contact surface 88 of the vessel 80 to improve adhesion of a subsequent coating of $SiO_x$.

VII.A.1.a. Thus, the coating 90 can comprise a layer of $SiO_x$ and a lubricity layer and/or hydrophobic layer, characterized as defined in the Definition Section. The lubricity layer and/or hydrophobic layer of $Si_wO_xC_yH_z$ can be deposited between the layer of $SiO_x$ and the interior contact surface of the vessel. Or, the layer of $SiO_x$ can be deposited between the lubricity layer and/or hydrophobic layer and the interior contact surface of the vessel. Or, three or more layers, either alternating or graduated between these two coating compositions: (1) a layer of $SiO_x$ and (2) the lubricity layer and/or hydrophobic layer; can also be used. The layer of $SiO_x$ can be deposited adjacent to the lubricity layer and/or hydrophobic layer or remotely, with at least one intervening layer of another material. The layer of $SiO_x$ can be deposited adjacent to the interior contact surface of the vessel. Or, the lubricity layer and/or hydrophobic layer can be deposited adjacent to the interior contact surface of the vessel.

VII.A.1.a. Another expedient contemplated here, for adjacent layers of $SiO_x$ and a lubricity layer and/or hydrophobic layer, is a graded composite of $Si_wO_xC_yH_z$, as defined in the Definition Section. A graded composite can be separate layers of a lubricity layer and/or hydrophobic layer and $SiO_x$ with a transition or interface of intermediate composition between them, or separate layers of a lubricity layer and/or hydrophobic layer and $SiO_x$ with an intermediate distinct layer of intermediate composition between them, or a single layer that changes continuously or in steps from a composition of a lubricity layer and/or hydrophobic layer to a composition more like $SiO_x$, going through the coating in a normal direction.

VII.A.1.a. The grade in the graded composite can go in either direction. For example, the a lubricity layer and/or hydrophobic layer can be applied directly to the substrate and graduate to a composition further from the contact surface of $SiO_x$. Or, the composition of $SiO_x$ can be applied directly to the substrate and graduate to a composition further from the contact surface of a lubricity layer and/or hydrophobic layer. A graduated coating is particularly contemplated if a coating of one composition is better for adhering to the substrate than the other, in which case the better-adhering composition can, for example, be applied directly to the substrate. It is contemplated that the more distant portions of the graded coating can be less compatible with the substrate than the adjacent portions of the graded coating, since at any point the coating is changing gradually in properties, so adjacent portions at nearly the same depth of the coating have nearly identical composition, and more widely physically separated portions at substantially different depths can have more diverse properties. It is also contemplated that a coating portion that forms a better barrier against transfer of material to or from the substrate can be directly against the substrate, to prevent the more remote coating portion that forms a poorer barrier from being contaminated with the material intended to be barred or impeded by the barrier.

VII.A.1.a. The coating, instead of being graded, optionally can have sharp transitions between one layer and the next, without a substantial gradient of composition. Such coatings can be made, for example, by providing the gases to produce a layer as a steady state flow in a non-plasma state, then energizing the system with a brief plasma discharge to form a coating on the substrate. If a subsequent coating is to be applied, the gases for the previous coating are cleared out and the gases for the next coating are applied in a steady-state fashion before energizing the plasma and again forming a distinct layer on the contact surface of the substrate or its outermost previous coating, with little if any gradual transition at the interface.

VII.A.1.b. Citrate Blood Tube Having Wall Coated with Hydrophobic Layer Deposited from an Organosilicon Precursor VII.A.1.b. Another embodiment is a cell preparation tube having a wall provided with a hydrophobic layer on its inside contact surface and containing an aqueous sodium citrate reagent. The hydrophobic layer can be also be applied on top of a hydrophilic $SiO_x$ coating on the internal contact surface of the tube. The $SiO_x$ coating increases the barrier properties of the thermoplastic tube and the hydrophobic layer changes the contact surface energy of blood contact surface with the tube wall.

VII.A.1.b. The wall is made of thermoplastic material having an internal contact surface defining a lumen.

VII.A.1.b. A blood collection tube according to the embodiment VII.A.1.b can have a first layer of $SiO_x$ on the internal contact surface of the tube, applied as explained in this specification, to function as an oxygen barrier and extend the shelf life of an evacuated blood collection tube made of thermoplastic material. A second layer of a hydrophobic layer, characterized as defined in the Definition Section, can then be applied over the barrier layer on the internal contact surface of the tube to provide a hydrophobic contact surface. The coating is effective to reduce the platelet activation of blood plasma treated with a sodium citrate additive and exposed to the inner contact surface, compared to the same type of wall uncoated.

VII.A.1.b. PECVD is used to form a hydrophobic layer on the internal contact surface, characterized as defined in the Definition Section. Unlike conventional citrate blood collection tubes, the blood collection tube having a hydrophobic layer, characterized as defined in the Definition Section does not require a coating of baked on silicone on the vessel wall, as is conventionally applied to make the contact surface of the tube hydrophobic.

VII.A.1.b. Both layers can be applied using the same precursor, for example HMDSO or OMCTS, and different PECVD reaction conditions.

VII.A.1.b. A sodium citrate anticoagulation reagent is then placed within the tube and it is evacuated and sealed with a closure to produce an evacuated blood collection tube. The components and formulation of the reagent are known to those skilled in the art. The aqueous sodium citrate reagent is disposed in the lumen of the tube in an amount effective to inhibit coagulation of blood introduced into the tube.

VII.A.1.c. $SiO_x$ Barrier Coated Double Wall Plastic Vessel—COC, PET, $SiO_x$ Layers VII.A.1.c. Another embodiment is a vessel having a wall at least partially enclosing a lumen. The wall has an interior polymer layer enclosed by an exterior polymer layer. One of the polymer layers is a layer at least 0.1 mm thick of a cyclic olefin copolymer (COC) resin defining a water vapor barrier. Another of the polymer layers is a layer at least 0.1 mm thick of a polyester resin.

VII.A.1.c. The wall includes an oxygen barrier layer of $SiO_x$ having a thickness of from about 10 to about 500 angstroms.

VII.A.1.c. In an embodiment, illustrated in FIG. 6, the vessel 80 can be a double-walled vessel having an inner wall 408 and an outer wall 410, respectively made of the same or different materials. One particular embodiment of this type can be made with one wall molded from a cyclic olefin copolymer (COC) and the other wall molded from a polyester such as polyethylene terephthalate (PET), with an $SiO_x$ coating as previously described on the interior contact surface 412. As needed, a tie coating or layer can be inserted between the inner and outer walls to promote adhesion between them. An advantage of this wall construction is that walls having different properties can be combined to form a composite having the respective properties of each wall.

VII.A.1.c. As one example, the inner wall 408 can be made of PET coated on the interior contact surface 412 with an $SiO_x$ barrier layer, and the outer wall 410 can be made of COC. PET coated with $SiO_x$, as shown elsewhere in this specification, is an excellent oxygen barrier, while COC is an excellent barrier for water vapor, providing a low water vapor transition rate (WVTR). This composite vessel can have superior barrier properties for both oxygen and water vapor. This construction is contemplated, for example, for an evacuated medical sample collection tube that contains an aqueous reagent as manufactured, and has a substantial shelf life, so it should have a barrier preventing transfer of water vapor outward or transfer of oxygen or other gases inward through its composite wall during its shelf life.

VII.A.1.c. As another example, the inner wall 408 can be made of COC coated on the interior contact surface 412 with an $SiO_x$ barrier layer, and the outer wall 410 can be made of PET. This construction is contemplated, for example, for a prefilled syringe that contains an aqueous sterile fluid as manufactured. The $SiO_x$ barrier will prevent oxygen from entering the syringe through its wall. The COC inner wall will prevent ingress or egress of other materials such as water, thus preventing the water in the aqueous sterile fluid from leaching materials from the wall material into the syringe. The COC inner wall is also contemplated to prevent water derived from the aqueous sterile fluid from passing out of the syringe (thus undesirably concentrating the aqueous sterile fluid), and will prevent non-sterile water or other fluids outside the syringe from entering through the syringe wall and causing the contents to become non-sterile. The COC inner wall is also contemplated to be useful for decreasing the breaking force or friction of the plunger against the inner wall of a syringe.

VII.A.1.d. Method of Making Double Wall Plastic Vessel—COC, PET, $SiO_x$ Layers

VII.A.1.d. Another embodiment is a method of making a vessel having a wall having an interior polymer layer enclosed by an exterior polymer layer, one layer made of COC and the other made of polyester. The vessel is made by a process including introducing COC and polyester resin layers into an injection mold through concentric injection nozzles.

VII.A.1.d. An optional additional step is applying an amorphous carbon coating to the vessel by PECVD, as an inside coating, an outside coating, or as an interlayer coating located between the layers.

VII.A.1.d. An optional additional step is applying an $SiO_x$ barrier layer to the inside of the vessel wall, where $SiO_x$ is defined as before. Another optional additional step is posttreating the SiO$_x$ layer with a process gas consisting essentially of oxygen and essentially free of a volatile silicon compound.

VII.A.1.d. Optionally, the SiO$_x$ coating can be formed at least partially from a silazane feed gas.

VII.A.1.d. The vessel 80 shown in FIG. 6 can be made from the inside out, for one example, by injection molding the inner wall in a first mold cavity, then removing the core and molded inner wall from the first mold cavity to a second, larger mold cavity, then injection molding the outer wall against the inner wall in the second mold cavity. Optionally, a tie layer can be provided to the exterior contact surface of the molded inner wall before over-molding the outer wall onto the tie layer.

VII.A.1.d. Or, the vessel 80 shown in FIG. 6 can be made from the outside in, for one example, by inserting a first core in the mold cavity, injection molding the outer wall in the mold cavity, then removing the first core from the molded first wall and inserting a second, smaller core, then injection molding the inner wall against the outer wall still residing in the mold cavity. Optionally, a tie layer can be provided to the interior contact surface of the molded outer wall before over-molding the inner wall onto the tie layer.

VII.A.1.d. Or, the vessel 80 shown in FIG. 6 can be made in a two shot mold. This can be done, for one example, by injection molding material for the inner wall from an inner nozzle and the material for the outer wall from a concentric outer nozzle. Optionally, a tie layer can be provided from a third, concentric nozzle disposed between the inner and outer nozzles. The nozzles can feed the respective wall materials simultaneously. One useful expedient is to begin feeding the outer wall material through the outer nozzle slightly before feeding the inner wall material through the inner nozzle. If there is an intermediate concentric nozzle, the order of flow can begin with the outer nozzle and continue in sequence from the intermediate nozzle and then from the inner nozzle. Or, the order of beginning feeding can start from the inside nozzle and work outward, in reverse order compared to the preceding description.

VII.A.1.e. Barrier Coating Made of Glass

VII.A.1.e. Another embodiment is a vessel including a barrier coating and a closure. The vessel is generally tubular and made of thermoplastic material. The vessel has a mouth and a lumen bounded at least in part by a wall having an inner contact surface interfacing with the lumen. There is an at least essentially continuous barrier coating made of glass on the inner contact surface of the wall. A closure covers the mouth and isolates the lumen of the vessel from ambient air.

VII.A.1.e. The vessel 80 can also be made, for example of glass of any type used in medical or laboratory applications, such as soda-lime glass, borosilicate glass, or other glass formulations. Other vessels having any shape or size, made of any material, are also contemplated for use in the system 20. One function of coating a glass vessel can be to reduce the ingress of ions in the glass, either intentionally or as impurities, for example sodium, calcium, or others, from the glass to the contents of the vessel, such as a reagent or blood in an evacuated blood collection tube. Another function of coating a glass vessel in whole or in part, such as selectively at contact surfaces contacted in sliding relation to other parts, is to provide lubricity to the coating, for example to ease the insertion or removal of a stopper or passage of a sliding element such as a piston in a syringe. Still another reason to coat a glass vessel is to prevent a reagent or intended sample for the vessel, such as blood, from sticking to the wall of the vessel or an increase in the rate of coagulation of the blood in contact with the wall of the vessel.

VII.A.1.e.i. A related embodiment is a vessel as described in the previous paragraph, in which the barrier coating is made of soda lime glass, borosilicate glass, or another type of glass.

VII.A.2. Stoppers

Figure 3:
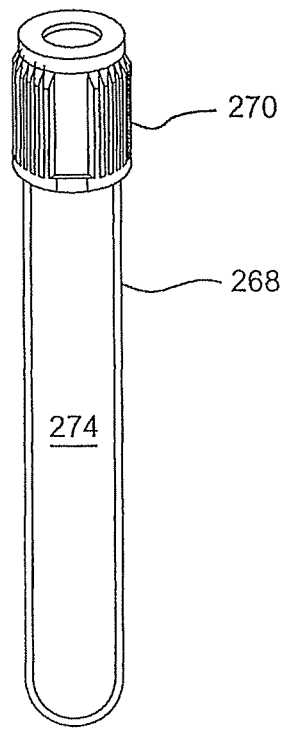
FIG. 3 is a perspective view of a blood collection tube assembly having a closure according to still another embodiment of the invention.
Figure 4:
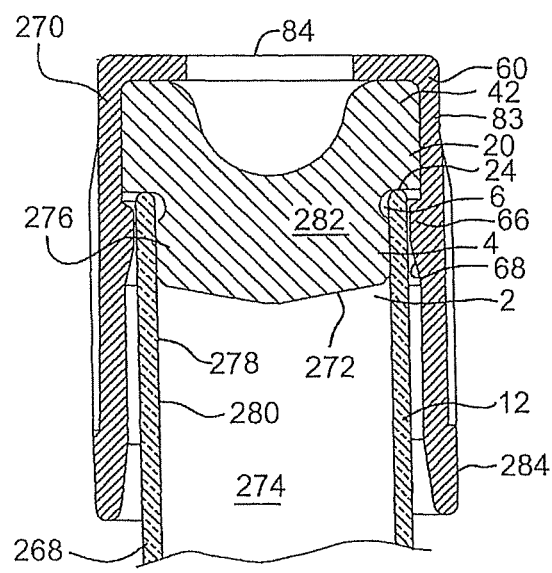
FIG. 4 is a fragmentary section of the blood collection tube and closure assembly of FIG. 3.
Figure 5:
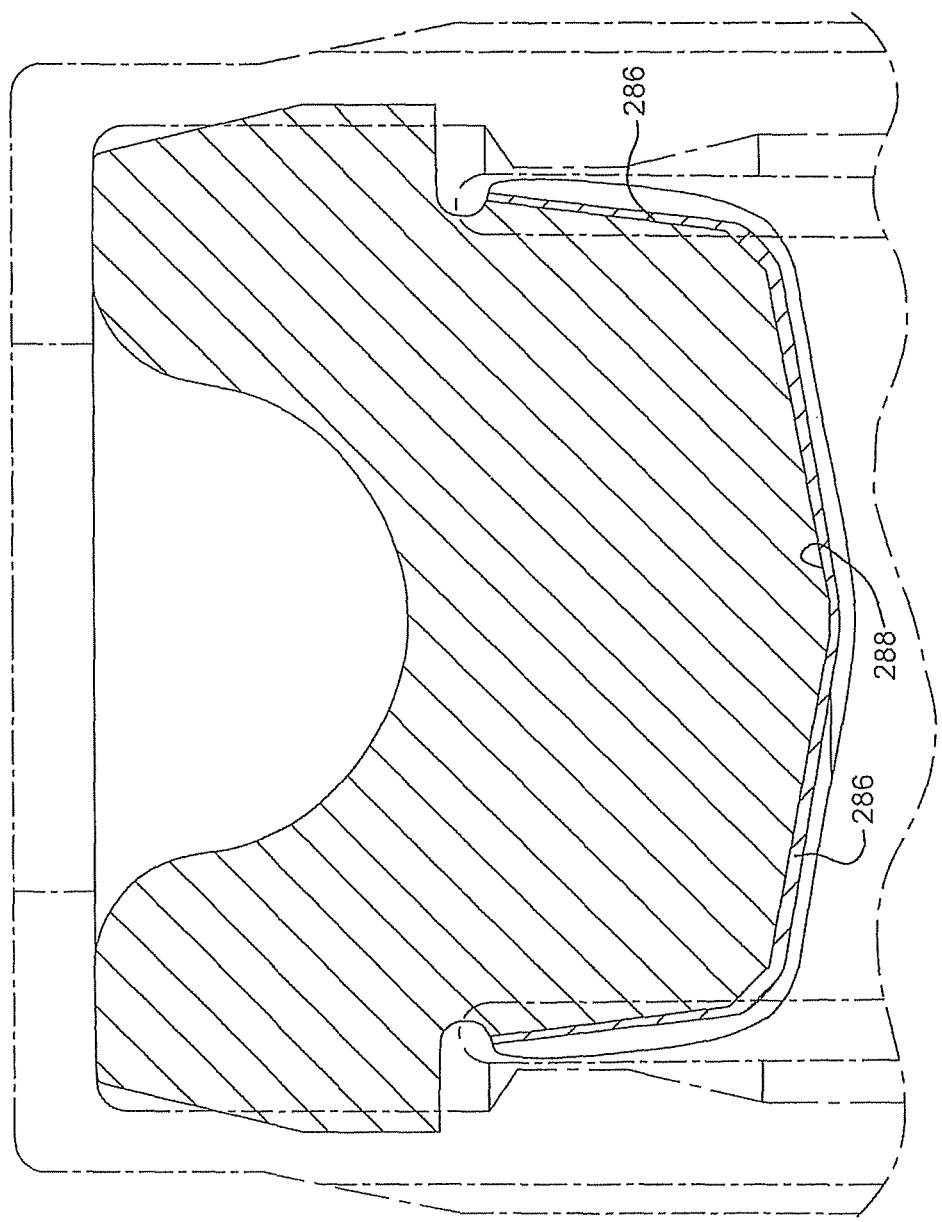
FIG. 5 is an isolated section of an elastomeric insert of the closure of FIGS. 3 and 4.

VII.A.2. FIGS. 3-5 illustrate a vessel 268, which can be an evacuated blood collection tube, having a closure 270 to isolate the lumen 274 from the ambient environment. The closure 270 comprises a interior-facing contact surface 272 exposed to the lumen 274 of the vessel 268 and a wall-contacting contact surface 276 that is in contact with the inner contact surface 278 of the vessel wall 280. In the illustrated embodiment the closure 270 is an assembly of a stopper 282 and a shield 284.

VII.A.2.a. Method of Applying Lubricity Layer to Stopper in Vacuum Chamber

VII.A.2.a. Another embodiment is a method of applying a coating on an elastomeric stopper such as 282. The stopper 282, separate from the vessel 268, is placed in a substantially evacuated chamber. A reaction mixture is provided including plasma forming gas, i.e. an organosilicon compound gas, optionally an oxidizing gas, and optionally a hydrocarbon gas. Plasma is formed in the reaction mixture, which is contacted with the stopper. A lubricity and/or hydrophobic layer, characterized as defined in the Definition Section, is deposited on at least a portion of the stopper.

VII.A.2.a. In the illustrated embodiment, the wall-contacting contact surface 276 of the closure 270 is coated with a lubricity layer 286.

VII.A.2.a. In some embodiments, the lubricity and/or hydrophobic layer, characterized as defined in the Definition Section, is effective to reduce the transmission of one or more constituents of the stopper, such as a metal ion constituent of the stopper, or of the vessel wall, into the vessel lumen. Certain elastomeric compositions of the type useful for fabricating a stopper 282 contain trace amounts of one or more metal ions. These ions sometimes should not be able to migrate into the lumen 274 or come in substantial quantities into contact with the vessel contents, particularly if the sample vessel 268 is to be used to collect a sample for trace metal analysis. It is contemplated for example that coatings containing relatively little organic content, i.e. where y and z of Si$_w$O$_x$C$_y$H$_z$ as defined in the Definition Section are low or zero, are particularly useful as a metal ion barrier in this application. Regarding silica as a metal ion barrier see, for example, Anupama Mallikarjunan, Jasbir Juneja, Guangrong Yang, Shyam P. Murarka, and Toh-Ming Lu, The Effect of Interfacial Chemistry on Metal Ion Penetration into Polymeric Films, Mat. Res. Soc. Symp. Proc., Vol. 734, pp. B9.60.1 to B9.60.6 (Materials Research Society, 2003); U.S. Pat. Nos. 5,578,103 and 6,200,658, and European Appl. EP0697378 A2, which are all incorporated here by reference. It is contemplated, however, that some organic content can be useful to provide a more elastic coating and to adhere the coating to the elastomeric contact surface of the stopper 282.

VII.A.2.a. In some embodiments, the lubricity and/or hydrophobic layer, characterized as defined in the Definition Section, can be a composite of material having first and second layers, in which the first or inner layer 288 interfaces with the elastomeric stopper 282 and is effective to reduce the transmission of one or more constituents of the stopper 282 into the vessel lumen. The second layer 286 can interface with the inner wall 280 of the vessel and is effective as a lubricity layer to reduce friction between the stopper 282 and the inner wall 280 of the vessel when the stopper 282 is seated on or in the vessel 268. Such composites are described in connection with syringe coatings elsewhere in this specification.

VII.A.2.a. Or, the first and second layers 288 and 286 are defined by a coating of graduated properties, in which the values of y and z defined in the Definition Section are greater in the first layer than in the second layer.

VII.A.2.a. The lubricity and/or hydrophobic layer can be applied, for example, by PECVD substantially as previously described. The lubricity and/or hydrophobic layer can be, for example, between 0.5 and 5000 nm (5 to 50,000 Angstroms) thick, or between 1 and 5000 nm thick, or between 5 and 5000 nm thick, or between 10 and 5000 nm thick, or between 20 and 5000 nm thick, or between 50 and 5000 nm thick, or between 100 and 5000 nm thick, or between 200 and 5000 nm thick, or between 500 and 5000 nm thick, or between 1000 and 5000 nm thick, or between 2000 and 5000 nm thick, or between 3000 and 5000 nm thick, or between 4000 and 10,000 nm thick.

VII.A.2.a. Certain advantages are contemplated for plasma coated lubricity layers, versus the much thicker (one micron or greater) conventional spray applied silicone lubricants. Plasma coatings have a much lower migratory potential to move into blood versus sprayed or micron-coated silicones, both because the amount of plasma coated material is much less and because it can be more intimately applied to the coated contact surface and better bonded in place.

VII.A.2.a. Nanocoatings, as applied by PECVD, are contemplated to offer lower resistance to sliding of an adjacent contact surface or flow of an adjacent fluid than micron coatings, as the plasma coating tends to provide a smoother contact surface.

VII.A.2.a. Still another embodiment is a method of applying a coating of a lubricity and/or hydrophobic layer on an elastomeric stopper. The stopper can be used, for example, to close the vessel previously described. The method includes several parts. A stopper is placed in a substantially evacuated chamber. A reaction mixture is provided comprising plasma forming gas, i.e. an organosilicon compound gas, optionally an oxidizing gas, and optionally a hydrocarbon gas. Plasma is formed in the reaction mixture. The stopper is contacted with the reaction mixture, depositing the coating of a lubricity and/or hydrophobic layer on at least a portion of the stopper.

VII.A.2.a. In practicing this method, to obtain higher values of y and z as defined in the Definition Section, it is contemplated that the reaction mixture can comprise a hydrocarbon gas, as further described above and below. Optionally, the reaction mixture can contain oxygen, if lower values of y and z or higher values of x are contemplated. Or, particularly to reduce oxidation and increase the values of y and z, the reaction mixture can be essentially free of an oxidizing gas.

VII.A.2.a. In practicing this method to coat certain embodiments of the stopper such as the stopper 282, it is contemplated to be unnecessary to project the reaction mixture into the concavities of the stopper. For example, the wall-contacting and interior facing contact surfaces 276 and 272 of the stopper 282 are essentially convex, and thus readily treated by a batch process in which a multiplicity of stoppers such as 282 can be located and treated in a single substantially evacuated reaction chamber. It is further contemplated that in some embodiments the coatings 286 and 288 do not need to present as formidable a barrier to oxygen or water as the barrier coating on the interior contact surface 280 of the vessel 268, as the material of the stopper 282 can serve this function to a large degree.

VII.A.2.a. Many variations of the stopper and the stopper coating process are contemplated. The stopper 282 can be contacted with the plasma. Or, the plasma can be formed upstream of the stopper 282, producing plasma product, and the plasma product can be contacted with the stopper 282. The plasma can be formed by exciting the reaction mixture with electromagnetic energy and/or microwave energy.

VII.A.2.a. Variations of the reaction mixture are contemplated. The plasma forming gas can include an inert gas. The inert gas can be, for example, argon or helium, or other gases described in this disclosure. The organosilicon compound gas can be, or include, HMDSO, OMCTS, any of the other organosilicon compounds mentioned in this disclosure, or a combination of two or more of these. The oxidizing gas can be oxygen or the other gases mentioned in this disclosure, or a combination of two or more of these. The hydrocarbon gas can be, for example, methane, methanol, ethane, ethylene, ethanol, propane, propylene, propanol, acetylene, or a combination of two or more of these.

VII.A.2.b. Applying by PECVD a Coating of Group III or IV Element and Carbon on a Stopper VII.A.2.b. Another embodiment is a method of applying a coating of a composition including carbon and one or more elements of Groups III or IV on an elastomeric stopper. To carry out the method, a stopper is located in a deposition chamber.

VII.A.2.b. A reaction mixture is provided in the deposition chamber, including a plasma forming gas with a gaseous source of a Group III element, a Group IV element, or a combination of two or more of these. The reaction mixture optionally contains an oxidizing gas and optionally contains a gaseous compound having one or more C—H bonds. Plasma is formed in the reaction mixture, and the stopper is contacted with the reaction mixture. A coating of a Group III element or compound, a Group IV element or compound, or a combination of two or more of these is deposited on at least a portion of the stopper.

VII.A.3. Stoppered Plastic Vessel Having Barrier Coating Effective to Provide 95% Vacuum Retention for 24 Months VII.A.3. Another embodiment is a vessel including a vessel, a barrier coating, and a closure. The vessel is generally tubular and made of thermoplastic material. The vessel has a mouth and a lumen bounded at least in part by a wall. The wall has an inner contact surface interfacing with the lumen. An at least essentially continuous barrier coating is applied on the inner contact surface of the wall. The barrier coating is effective to provide a substantial shelf life. A closure is provided covering the mouth of the vessel and isolating the lumen of the vessel from ambient air.

VII.A.3. Referring to FIGS. 3-5, a vessel 268 such as an evacuated blood collection tube or other vessel is shown.

VII.A.3. The vessel is, in this embodiment, a generally tubular vessel having an at least essentially continuous barrier coating and a closure. The vessel is made of thermoplastic material having a mouth and a lumen bounded at least in part by a wall having an inner contact surface interfacing with the lumen. The barrier coating is deposited on the inner contact surface of the wall, and is effective to maintain at least 95%, or at least 90%, of the initial vacuum level of the vessel for a shelf life of at least 24 months, optionally at least 30 months, optionally at least 36 months. The closure covers the mouth of the vessel and isolates the lumen of the vessel from ambient air.

VII.A.3. The closure, for example the closure 270 illustrated in the Figures or another type of closure, is provided to maintain a partial vacuum and/or to contain a sample and limit or prevent its exposure to oxygen or contaminants. FIGS. 3-5 are based on figures found in U.S. Pat. No. 6,602,206, but the present discovery is not limited to that or any other particular type of closure.

VII.A.3. The closure 270 comprises a interior-facing contact surface 272 exposed to the lumen 274 of the vessel 268 and a wall-contacting contact surface 276 that is in contact with the inner contact surface 278 of the vessel wall 280. In the illustrated embodiment the closure 270 is an assembly of a stopper 282 and a shield 284.

VII.A.3. In the illustrated embodiment, the stopper 282 defines the wall-contacting contact surface 276 and the inner contact surface 278, while the shield is largely or entirely outside the stoppered vessel 268, retains and provides a grip for the stopper 282, and shields a person removing the closure 270 from being exposed to any contents expelled from the vessel 268, such as due to a pressure difference inside and outside of the vessel 268 when the vessel 268 is opened and air rushes in or out to equalize the pressure difference.

VII.A.3. It is further contemplated that the coatings on the vessel wall 280 and the wall contacting contact surface 276 of the stopper can be coordinated. The stopper can be coated with a lubricity silicone layer, and the vessel wall 280, made for example of PET or glass, can be coated with a harder $SiO_x$ layer, or with an underlying $SiO_x$ layer and a lubricity overcoat.

VII.B. Syringes

VII.B. The foregoing description has largely addressed applying a barrier coating to a tube with one permanently closed end, such as a blood collection tube or, more generally, a specimen receiving tube 80. The apparatus is not limited to such a device.

Figure 2:
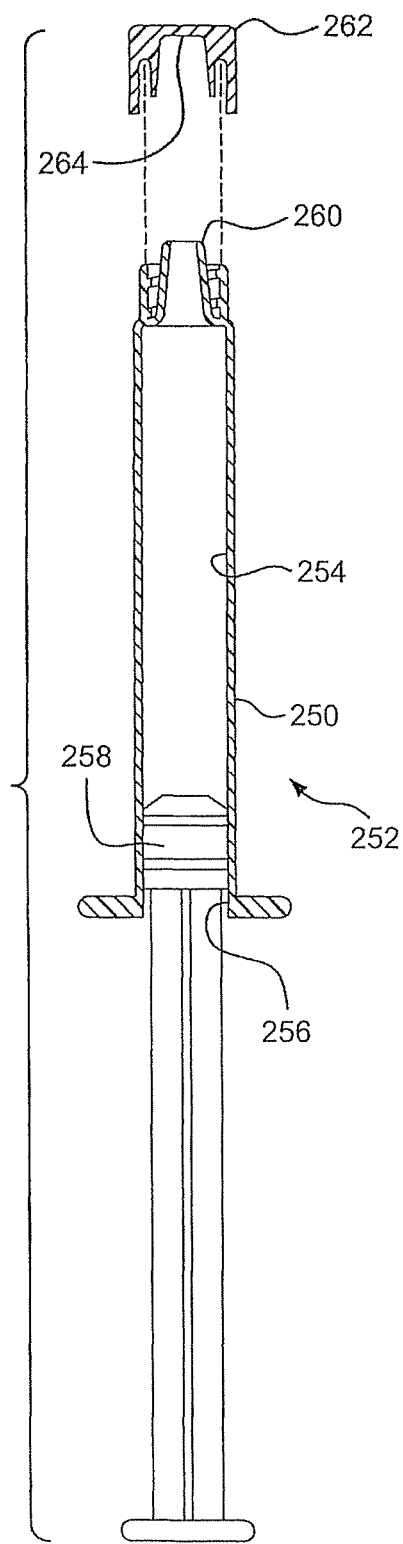
FIG. 2 is an exploded longitudinal sectional view of a syringe and cap adapted for use as a prefilled syringe.

VII.B. Another example of a suitable vessel, shown in FIG. 2, is a syringe barrel 250 for a medical syringe 252. Such syringes 252 are sometimes supplied prefilled with saline solution, a pharmaceutical preparation, or the like for use in medical techniques. Pre-filled syringes 252 are also contemplated to benefit from an $SiO_x$ barrier or other type of coating on the interior contact surface 254 to keep the contents of the prefilled syringe 252 out of contact with the plastic of the syringe, for example of the syringe barrel 250 during storage. The barrier or other type of coating can be used to avoid leaching components of the plastic into the contents of the barrel through the interior contact surface 254.

VII.B. A syringe barrel 250 as molded commonly can be open at both the back end 256, to receive a plunger 258, and at the front end 260, to receive a hypodermic needle, a nozzle, or tubing for dispensing the contents of the syringe 252 or for receiving material into the syringe 252. But the front end 260 can optionally be capped and the plunger 258 optionally can be fitted in place before the prefilled syringe 252 is used, closing the barrel 250 at both ends. A cap 262 can be installed either for the purpose of processing the syringe barrel 250 or assembled syringe, or to remain in place during storage of the prefilled syringe 252, up to the time the cap 262 is removed and (optionally) a hypodermic needle or other delivery conduit is fitted on the front end 260 to prepare the syringe 252 for use.

VII.B.1.a. Syringe Having Barrel Coated with Lubricity Layer Deposited from an Organosilicon Precursor VII.B.1.a. Still another embodiment is a vessel having a lubricity layer, characterized as defined in the Definition Section, of the type made by the following process.

VII.B.1.a. A precursor is provided as defined above.

VII.B.1.a. The precursor is applied to a substrate under conditions effective to form a coating. The coating is polymerized or crosslinked, or both, to form a lubricated contact surface having a lower plunger sliding force or breakout force than the untreated substrate.

VII.B.1.a. Respecting any of the Embodiments VII and sub-parts, optionally the applying step is carried out by vaporizing the precursor and providing it in the vicinity of the substrate.

VII.B.1.a. Respecting any of the Embodiments VII.A.1.a.i, optionally a plasma, optionally a non-hollow-cathode plasma, is formed in the vicinity of the substrate. Optionally, the precursor is provided in the substantial absence of oxygen. Optionally, the precursor is provided in the substantial absence of a carrier gas. Optionally, the precursor is provided in the substantial absence of nitrogen. Optionally, the precursor is provided at less than 1 Torr absolute pressure. Optionally, the precursor is provided to the vicinity of a plasma emission. Optionally, the precursor its reaction product is applied to the substrate at a thickness of 1 to 5000 nm thick, or 10 to 1000 nm thick, or 10-200 nm thick, or 20 to 100 nm thick. Optionally, the substrate comprises glass. Optionally, the substrate comprises a polymer, optionally a polycarbonate polymer, optionally an olefin polymer, optionally a cyclic olefin copolymer, optionally a polypropylene polymer, optionally a polyester polymer, optionally a polyethylene terephthalate polymer.

VII.B.1.a. Optionally, the plasma is generated by energizing the gaseous reactant containing the precursor with electrodes powered, for example, at a RF frequency as defined above, for example a frequency of from 10 kHz to less than 300 MHz, optionally from 1 to 50 MHz, even optionally from 10 to 15 MHz, optionally a frequency of 13.56 MHz.

VII.B.1.a. Optionally, the plasma is generated by energizing the gaseous reactant containing the precursor with electrodes supplied with an electric power of from 0.1 to 25 W, optionally from 1 to 22 W, optionally from 3 to 17 W, even optionally from 5 to 14 W, optionally from 7 to 11 W, optionally 8 W. The ratio of the electrode power to the plasma volume can be less than 10 W/ml, optionally is from 5 W/ml to 0.1 W/ml, optionally is from 4 W/ml to 0.1 W/ml, optionally is from 2 W/ml to 0.2 W/ml. These power levels are suitable for applying lubricity layers to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

VII.B.1.a. Another embodiment is a lubricity layer, characterized as defined in the Definition Section, on the inner wall of a syringe barrel. The coating is produced from a PECVD process using the following materials and conditions. A cyclic precursor is optionally employed, selected from a monocyclic siloxane, a polycyclic siloxane, or a combination of two or more of these, as defined elsewhere in this specification for lubricity layers. One example of a suitable cyclic precursor comprises octamethylcyclotetrasiloxane (OMCTS), optionally mixed with other precursor materials in any proportion. Optionally, the cyclic precursor consists essentially of octamethylcyclotetrasiloxane (OMCTS), meaning that other precursors can be present in amounts which do not change the basic and novel properties of the resulting lubricity layer, i.e. its reduction of the plunger sliding force or breakout force of the coated contact surface.

VII.B.1.a. At least essentially no oxygen as defined in the Definition Section is added to the process.

VII.B.1.a. A sufficient plasma generation power input, for example any power level successfully used in one or more working examples of this specification or described in the specification, is provided to induce coating formation.

VII.B.1.a. The materials and conditions employed are effective to reduce the syringe plunger sliding force or breakout force moving through the syringe barrel at least 25 percent, alternatively at least 45 percent, alternatively at least 60 percent, alternatively greater than 60 percent, relative to an uncoated syringe barrel. Ranges of plunger sliding force or breakout force reduction of from 20 to 95 percent, alternatively from 30 to 80 percent, alternatively from 40 to 75 percent, alternatively from 60 to 70 percent, are contemplated.

VII.B.1.a. Another embodiment is a vessel having a hydrophobic layer, characterized as defined in the Definition Section, on the inside wall. The coating is made as explained for the lubricant coating of similar composition, but under conditions effective to form a hydrophobic contact surface having a higher contact angle than the untreated substrate.

VII.B.1.a. Respecting any of the Embodiments VII.A.1.a.ii, optionally the substrate comprises glass or a polymer. The glass optionally is borosilicate glass. The polymer is optionally a polycarbonate polymer, optionally an olefin polymer, optionally a cyclic olefin copolymer, optionally a polypropylene polymer, optionally a polyester polymer, optionally a polyethylene terephthalate polymer.

VII.B.1.a. Another embodiment is a syringe including a plunger, a syringe barrel, and a lubricity layer, characterized as defined in the Definition Section. The syringe barrel includes an interior contact surface receiving the plunger for sliding. The lubricity layer is disposed on the interior contact surface of the syringe barrel. The lubricity layer is less than 1000 nm thick and effective to reduce the breakout force or the plunger sliding force necessary to move the plunger within the barrel. Reducing the plunger sliding force is alternatively expressed as reducing the coefficient of sliding friction of the plunger within the barrel or reducing the plunger force; these terms are regarded as having the same meaning in this specification.

VII.B.1.a. Any of the above precursors of any type can be used alone or in combinations of two or more of them to provide a lubricity layer.

VII.B.1.a. In addition to utilizing vacuum processes, low temperature atmospheric (non-vacuum) plasma processes can also be utilized to induce molecular ionization and deposition through precursor monomer vapor delivery optionally in a non-oxidizing atmosphere such as helium or argon. Separately, thermal CVD can be considered via flash thermolysis deposition.

VII.B.1.a. The approaches above are similar to vacuum PECVD in that the contact surface coating and crosslinking mechanisms can occur simultaneously.

VII.B.1.a. Yet another expedient contemplated for any coating or coatings described here is a coating that is not uniformly applied over the entire interior 88 of a vessel. For example, a different or additional coating can be applied selectively to the cylindrical portion of the vessel interior, compared to the hemispherical portion of the vessel interior at its closed end 84, or vice versa. This expedient is particularly contemplated for a syringe barrel or a sample collection tube as described below, in which a lubricity layer might be provided on part or all of the cylindrical portion of the barrel, where the plunger or piston or closure slides, and not elsewhere.

VII.B.1.a. Optionally, the precursor can be provided in the presence, substantial absence, or absence of oxygen, in the presence, substantial absence, or absence of nitrogen, or in the presence, substantial absence, or absence of a carrier gas. In one contemplated embodiment, the precursor alone is delivered to the substrate and subjected to PECVD to apply and cure the coating.

VII.B.1.a. Optionally, the precursor can be provided at less than 1 Torr absolute pressure.

VII.B.1.a. Optionally, the precursor can be provided to the vicinity of a plasma emission.

VII.B.1.a. Optionally, the precursor its reaction product can be applied to the substrate at a thickness of 1 to 5000 nm, or 10 to 1000 nm, or 10-200 nm, or 20 to 100 nm.

VII.B.1.a. In any of the above embodiments, the substrate can comprise glass, or a polymer, for example one or more of a polycarbonate polymer, an olefin polymer (for example a cyclic olefin copolymer or a polypropylene polymer), or a polyester polymer (for example, a polyethylene terephthalate polymer).

VII.B.1.a. In any of the above embodiments, the plasma is generated by energizing the gaseous reactant containing the precursor with electrodes powered at a RF frequency as defined in this description.

VII.B.1.a. In any of the above embodiments, the plasma is generated by energizing the gaseous reactant containing the precursor with electrodes supplied with sufficient electric power to generate a lubricity layer. Optionally, the plasma is generated by energizing the gaseous reactant containing the precursor with electrodes supplied with an electric power of from 0.1 to 25 W, optionally from 1 to 22 W, optionally from 3 to 17 W, even optionally from 5 to 14 W, optionally from 7 to 11 W, optionally 8 W. The ratio of the electrode power to the plasma volume can be less than 10 W/ml, optionally is from 5 W/ml to 0.1 W/ml, optionally is from 4 W/ml to 0.1 W/ml, optionally from 2 W/ml to 0.2 W/ml. These power levels are suitable for applying lubricity layers to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

VII.B.1.a. The coating can be cured, as by polymerizing or crosslinking the coating, or both, to form a lubricated contact surface having a lower plunger sliding force or breakout force than the untreated substrate. Curing can occur during the application process such as PECVD, or can be carried out or at least completed by separate processing.

VII.B.1.a. Although plasma deposition has been used herein to demonstrate the coating characteristics, alternate deposition methods can be used as long as the chemical composition of the starting material is preserved as much as possible while still depositing a solid film that is adhered to the base substrate.

VII.B.1.a. For example, the coating material can be applied onto the syringe barrel (from the liquid state) by spraying the coating or dipping the substrate into the coating, where the coating is either the neat precursor a solvent-diluted precursor (allowing the mechanical deposition of a thinner coating). The coating optionally can be crosslinked using thermal energy, UV energy, electron beam energy, plasma energy, or any combination of these.

VII.B.1.a. Application of a silicone precursor as described above onto a contact surface followed by a separate curing step is also contemplated. The conditions of application and curing can be analogous to those used for the atmospheric plasma curing of pre-coated polyfluoroalkyl ethers, a process practiced under the trademark TriboGlide®. More details of this process can be found at http://www.triboglide.com/process.htm.

VII.B.1.a. In such a process, the area of the part to be coated can optionally be pre-treated with an atmospheric plasma. This pretreatment cleans and activates the contact surface so that it is receptive to the lubricant that is sprayed in the next step.

VII.B.1.a. The lubrication fluid, in this case one of the above precursors or a polymerized precursor, is then sprayed on to the contact surface to be treated. For example, IVEK precision dispensing technology can be used to accurately atomize the fluid and create a uniform coating.

VII.B.1.a. The coating is then bonded or crosslinked to the part, again using an atmospheric plasma field. This both immobilizes the coating and improves the lubricant's performance.

VII.B.1.a. Optionally, the atmospheric plasma can be generated from ambient air in the vessel, in which case no gas feed and no vacuum drawing equipment is needed. Optionally, however, the vessel is at least substantially closed while plasma is generated, to minimize the power requirement and prevent contact of the plasma with contact surfaces or materials outside the vessel.

VII.B.1.a.i. Lubricity Layer: $SiO_x$ Barrier, Lubricity Layer, Contact Surface Treatment Contact Surface Treatment VII.B.1.a.i. Another embodiment is a syringe comprising a barrel defining a lumen and having an interior contact surface slidably receiving a plunger, i.e. receiving a plunger for sliding contact to the interior contact surface.

VII.B.1.a.i. The syringe barrel is made of thermoplastic base material.

VII.B.1.a.i. Optionally, the interior contact surface of the barrel is coated with an $SiO_x$ barrier layer as described elsewhere in this specification.

VII.B.1.a.i. A lubricity layer is applied to the barrel interior contact surface, the plunger, or both, or to the previously applied $SiO_x$ barrier layer. The lubricity layer can be provided, applied, and cured as set out in embodiment VII.B.1.a or elsewhere in this specification.

VII.B.1.a.i. For example, the lubricity layer can be applied, in any embodiment, by PECVD. The lubricity layer is deposited from an organosilicon precursor, and is less than 1000 nm thick.

VII.B.1.a.i. A contact surface treatment is carried out on the lubricity layer in an amount effective to reduce the leaching or extractables of the lubricity layer, the thermoplastic base material, or both. The treated contact surface can thus act as a solute retainer. This contact surface treatment can result in a skin coating, e.g. a skin coating which is at least 1 nm thick and less than 100 nm thick, or less than 50 nm thick, or less than 40 nm thick, or less than 30 nm thick, or less than 20 nm thick, or less than 10 nm thick, or less than 5 nm thick, or less than 3 nm thick, or less than 2 nm thick, or less than 1 nm thick, or less than 0.5 nm thick.

VII.B.1.a.i. As used herein, "leaching" refers to material transferred out of a substrate, such as a vessel wall, into the contents of a vessel, for example a syringe. Commonly, leachables are measured by storing the vessel filled with intended contents, then analyzing the contents to determine what material leached from the vessel wall into the intended contents. "Extraction" refers to material removed from a substrate by introducing a solvent or dispersion medium other than the intended contents of the vessel, to determine what material can be removed from the substrate into the extraction medium under the conditions of the test.

VII.B.1.a.i. The contact surface treatment resulting in a solute retainer optionally can be a $SiO_x$ layer as previously defined in this specification or a hydrophobic layer, characterized as defined in the Definition Section. In one embodiment, the contact surface treatment can be applied by PECVD deposit of $SiO_x$ or a hydrophobic layer. Optionally, the contact surface treatment can be applied using higher power or stronger oxidation conditions than used for creating the lubricity layer, or both, thus providing a harder, thinner, continuous solute retainer 539. Contact surface treatment can be less than 100 nm deep, optionally less than 50 nm deep, optionally less than 40 nm deep, optionally less than 30 nm deep, optionally less than 20 nm deep, optionally less than 10 nm deep, optionally less than 5 nm deep, optionally less than 3 nm deep, optionally less than 1 nm deep, optionally less than 0.5 nm deep, optionally between 0.1 and 50 nm deep in the lubricity layer.

VII.B.1.a.i. The solute retainer is contemplated to provide low solute leaching performance to the underlying lubricity and other layers, including the substrate, as required. This retainer would only need to be a solute retainer to large solute molecules and oligomers (for example siloxane monomers such as HMDSO, OMCTS, their fragments and mobile oligomers derived from lubricants, for example a "leachables retainer") and not a gas ($O_2/N_2/CO_2$/water vapor) barrier layer. A solute retainer can, however, also be a gas barrier (e.g. the $SiO_x$ coating according to present invention. One can create a good leachable retainer without gas barrier performance, either by vacuum or atmospheric-based PECVD processes. It is desirable that the "leachables barrier" will be sufficiently thin that, upon syringe plunger movement, the plunger will readily penetrate the "solute retainer" exposing the sliding plunger nipple to the lubricity layer immediately below to form a lubricated contact surface having a lower plunger sliding force or breakout force than the untreated substrate.

VII.B.1.a.i. In another embodiment, the contact surface treatment can be performed by oxidizing the contact surface of a previously applied lubricity layer, as by exposing the contact surface to oxygen in a plasma environment. The plasma environment described in this specification for forming $SiO_x$ coatings can be used. Or, atmospheric plasma conditions can be employed in an oxygen-rich environment.

VII.B.1.a.i. The lubricity layer and solute retainer, however formed, optionally can be cured at the same time. In another embodiment, the lubricity layer can be at least partially cured, optionally fully cured, after which the contact surface treatment can be provided, applied, and the solute retainer can be cured.

VII.B.1.a.i. The lubricity layer and solute retainer are composed, and present in relative amounts, effective to provide a breakout force, plunger sliding force, or both that is less than the corresponding force required in the absence of the lubricity layer and contact surface treatment. In other words, the thickness and composition of the solute retainer are such as to reduce the leaching of material from the lubricity layer into the contents of the syringe, while allowing the underlying lubricity layer to lubricate the plunger. It is contemplated that the solute retainer will break away easily and be thin enough that the lubricity layer will still function to lubricate the plunger when it is moved.

VII.B.1.a.i. In one contemplated embodiment, the lubricity and contact surface treatments can be applied on the barrel interior contact surface. In another contemplated embodiment, the lubricity and contact surface treatments can be applied on the plunger. In still another contemplated embodiment, the lubricity and contact surface treatments can be applied both on the barrel interior contact surface and on the plunger. In any of these embodiments, the optional $SiO_x$ barrier layer on the interior of the syringe barrel can either be present or absent.

VII.B.1.a.i. One embodiment contemplated is a plural-layer, e.g. a 3-layer, configuration applied to the inside contact surface of a syringe barrel. Layer 1 can be an $SiO_x$ gas barrier made by PECVD of HMDSO, OMCTS, or both, in an oxidizing atmosphere. Such an atmosphere can be provided, for example, by feeding HMDSO and oxygen gas to a PECVD coating apparatus as described in this specification.

Layer 2 can be a lubricity layer using OMCTS applied in a non-oxidizing atmosphere. Such a non-oxidizing atmosphere can be provided, for example, by feeding OMCTS to a PECVD coating apparatus as described in this specification, optionally in the substantial or complete absence of oxygen. A subsequent solute retainer can be formed by a treatment forming a thin skin layer of $SiO_x$ or a hydrophobic layer as a solute retainer using higher power and oxygen using OMCTS and/or HMDSO.

VII.B.1.a.i. Certain of these plural-layer coatings are contemplated to have one or more of the following optional advantages, at least to some degree. They can address the reported difficulty of handling silicone, since the solute retainer can confine the interior silicone and prevent it from migrating into the contents of the syringe or elsewhere, resulting in fewer silicone particles in the deliverable contents of the syringe and less opportunity for interaction between the lubricity layer and the contents of the syringe. They can also address the issue of migration of the lubricity layer away from the point of lubrication, improving the lubricity of the interface between the syringe barrel and the plunger. For example, the break-free force can be reduced and the drag on the moving plunger can be reduced, or optionally both.

VII.B.1.a.i. It is contemplated that when the solute retainer is broken, the solute retainer will continue to adhere to the lubricity layer and the syringe barrel, which can inhibit any particles from being entrained in the deliverable contents of the syringe.

VII.B.1.a.i. Certain of these coatings will also provide manufacturing advantages, particularly if the barrier coating, lubricity layer and contact surface treatment are applied in the same apparatus, for example the illustrated PECVD apparatus. Optionally, the $SiO_x$ barrier coating, lubricity layer, and contact surface treatment can all be applied in one PECVD apparatus, thus greatly reducing the amount of handling necessary.

Further advantages can be obtained by forming the barrier coating, lubricity layer, and solute retainer using the same precursors and varying the process. For example, an $SiO_x$ gas barrier layer can be applied using an OMCTS precursor under high power/high $O_2$ conditions, followed by applying a lubricity layer applied using an OMCTS precursor under low power and/or in the substantial or complete absence of oxygen, finishing with a contact surface treatment using an OMCTS precursor under intermediate power and oxygen.

VII.B.1.b Syringe Having Barrel with $SiO_x$ Coated Interior and Barrier Coated Exterior VII.B.1.b. In any embodiment, the thermoplastic base material optionally can include a polyolefin, for example polypropylene or a cyclic olefin copolymer (for example the material sold under the trademark TOPAS®), a polyester, for example polyethylene terephthalate, a polycarbonate, for example a bisphenol A polycarbonate thermoplastic, or other materials. Composite syringe barrels are contemplated having any one of these materials as an outer layer and the same or a different one of these materials as an inner layer. Any of the material combinations of the composite syringe barrels or sample tubes described elsewhere in this specification can also be used.

VII.B.1.b. In any embodiment, the resin optionally can include polyvinylidene chloride in homopolymer or copolymer form. For example, the PVdC homopolymers (trivial name: Saran) or copolymers described in U.S. Pat. No. 6,165,566, incorporated here by reference, can be employed. The resin optionally can be applied onto the exterior contact surface of the barrel in the form of a latex or other dispersion.

VII.B.1.b. In any embodiment, the syringe barrel 548 optionally can include a lubricity layer disposed between the plunger and the barrier coating of $SiO_x$. Suitable lubricity layers are described elsewhere in this specification.

VII.B.1.b. In any embodiment, the lubricity layer optionally can be applied by PECVD and optionally can include material characterized as defined in the Definition Section.

VII.B.1.b. In any embodiment, the syringe barrel 548 optionally can include a contact surface treatment covering the lubricity layer in an amount effective to reduce the leaching of the lubricity layer, constituents of the thermoplastic base material, or both into the lumen 604.

VII.B.1.c Method of Making Syringe Having Barrel with $SiO_x$ Coated Interior and Barrier Coated Exterior VII.B.1.c. Even another embodiment is a method of making a syringe as described in any of the embodiments of part VII.B.1.b, including a plunger, a barrel, and interior and exterior barrier coatings. A barrel is provided having an interior contact surface for receiving the plunger for sliding and an exterior contact surface. A barrier coating of $SiO_x$ is provided on the interior contact surface of the barrel by PECVD. A barrier coating of a resin is provided on the exterior contact surface of the barrel. The plunger and barrel are assembled to provide a syringe.

VII.B.1.c. For effective coating (uniform wetting) of the plastic article with the aqueous latex, it is contemplated to be useful to match the contact surface tension of the latex to the plastic substrate. This can be accomplished by several approaches, independently or combined, for example, reducing the contact surface tension of the latex (with surfactants or solvents), and/or corona pretreatment of the plastic article, and/or chemical priming of the plastic article.

VII.B.1.c. The resin optionally can be applied via dip coating of the latex onto the exterior contact surface of the barrel, spray coating of the latex onto the exterior contact surface of the barrel, or both, providing plastic-based articles offering improved gas and vapor barrier performance. Polyvinylidene chloride plastic laminate articles can be made that provide significantly improved gas barrier performance versus the non-laminated plastic article.

VII.B.1.c. In any embodiment, the resin optionally can be heat cured. The resin optionally can be cured by removing water. Water can be removed by heat curing the resin, exposing the resin to a partial vacuum or low-humidity environment, catalytically curing the resin, or other expedients.

VII.B.1.c. An effective thermal cure schedule is contemplated to provide final drying to permit PVdC crystallization, offering barrier performance. Primary curing can be carried out at an elevated temperature, for example between 180-310° F. (82-154° C.), of course depending on the heat tolerance of the thermoplastic base material. Barrier performance after the primary cure optionally can be about 85% of the ultimate barrier performance achieved after a final cure.

VII.B.1.c. A final cure can be carried out at temperatures ranging from ambient temperature, such as about 65-75° F. (18-24° C.) for a long time (such as 2 weeks) to an elevated temperature, such as 122° F. (50° C.), for a short time, such as four hours.

VII.B.1.c. The PVdC-plastic laminate articles, in addition to superior barrier performance, are optionally contemplated to provide one or more desirable properties such as colorless transparency, good gloss, abrasion resistance, printability, and mechanical strain resistance.

VII.B.2. Plungers

VII.B.2.a. With Barrier Coated Piston Front Face

VII.B.2.a. Another embodiment is a plunger for a syringe, including a piston and a push rod. The piston has a front face, a generally cylindrical side face, and a back portion, the side face being configured to movably seat within a syringe barrel. The front face has a barrier coating. The push rod engages the back portion and is configured for advancing the piston in a syringe barrel.

VII.B.2.b. With Lubricity Layer Interfacing with Side Face

VII.B.2.b. Yet another embodiment is a plunger for a syringe, including a piston, a lubricity layer, and a push rod. The piston has a front face, a generally cylindrical side face, and a back portion. The side face is configured to movably seat within a syringe barrel. The lubricity layer interfaces with the side face. The push rod engages the back portion of the piston and is configured for advancing the piston in a syringe barrel.

VII.B.3. Two Piece Syringe and Luer Fitting

VII.B.3. Another embodiment is a syringe including a plunger, a syringe barrel, and a Luer fitting. The syringe includes a barrel having an interior contact surface receiving the plunger for sliding. The Luer fitting includes a Luer taper having an internal passage defined by an internal contact surface. The Luer fitting is formed as a separate piece from the syringe barrel and joined to the syringe barrel by a coupling. The internal passage of the Luer taper has a barrier coating of $SiO_x$.

VII.B.4. Lubricant Compositions—Lubricity Layer Deposited from an Organosilicon Precursor Made by In Situ Polymerizing Organosilicon Precursor VII.B.4.a. Product by Process and Lubricity VII.B.4.a. Still another embodiment is a lubricity layer. This coating can be of the type made by the following process.

VII.B.4.a. Any of the precursors mentioned elsewhere in this specification can be used, alone or in combination. The precursor is applied to a substrate under conditions effective to form a coating. The coating is polymerized or crosslinked, or both, to form a lubricated contact surface having a lower plunger sliding force or breakout force than the untreated substrate.

VII.B.4.a. Another embodiment is a method of applying a lubricity layer. An organosilicon precursor is applied to a substrate under conditions effective to form a coating. The coating is polymerized or crosslinked, or both, to form a lubricated contact surface having a lower plunger sliding force or breakout force than the untreated substrate.

VII.B.4.b. Product by Process and Analytical Properties

VII.B.4.b. Even another aspect of the invention is a lubricity layer deposited by PECVD from a feed gas comprising an organometallic precursor, optionally an organosilicon precursor, optionally a linear siloxane, a linear silazane, a monocyclic siloxane, a monocyclic silazane, a polycyclic siloxane, a polycyclic silazane, or any combination of two or more of these. The coating has a density between 1.25 and 1.65 g/cm³ optionally between 1.35 and 1.55 g/cm³, optionally between 1.4 and 1.5 g/cm³, optionally between 1.44 and 1.48 g/cm³ as determined by X-ray reflectivity (XRR).

VII.B.4.b. Still another aspect of the invention is a lubricity layer deposited by PECVD from a feed gas comprising an organometallic precursor, optionally an organosilicon precursor, optionally a linear siloxane, a linear silazane, a monocyclic siloxane, a monocyclic silazane, a polycyclic siloxane, a polycyclic silazane, or any combination of two or more of these. The coating has as an outgas component one or more oligomers containing repeating -(Me)$_2$SiO— moieties, as determined by gas chromatography/mass spectrometry. Optionally, the coating meets the limitations of any of embodiments VII.B.4.a or VII.B.4.b.A.585h. Optionally, the coating outgas component as determined by gas chromatography/mass spectrometry is substantially free of trimethylsilanol.

VII.B.4.b. Optionally, the coating outgas component can be at least 10 ng/test of oligomers containing repeating -(Me)$_2$SiO— moieties, as determined by gas chromatography/mass spectrometry using the following test conditions:

GC Column: 30 m×0.25 mm DB-5MS (J&W Scientific), 0.25 µm film thickness
Flow rate: 1.0 ml/min, constant flow mode
Detector: Mass Selective Detector (MSD)
Injection Mode: Split injection (10:1 split ratio)
Outgassing Conditions: 1½" (37 mm) Chamber, purge for three hour at 85° C., flow 60 ml/min
Oven temperature: 40° C. (5 min.) to 300° C. at 10° C./min.; hold for 5 min. at 300° C.

VII.B.4.b. Optionally, the outgas component can include at least 20 ng/test of oligomers containing repeating -(Me)$_2$SiO— moieties.

VII.B.4.b. Optionally, the feed gas comprises a monocyclic siloxane, a monocyclic silazane, a polycyclic siloxane, a polycyclic silazane, or any combination of two or more of these, for example a monocyclic siloxane, a monocyclic silazane, or any combination of two or more of these, for example octamethylcyclotetrasiloxane.

VII.B.4.b. The lubricity layer of any embodiment can have a thickness measured by transmission electron microscopy (TEM) between 1 and 500 nm, optionally between 10 and 500 nm, optionally between 20 and 200 nm, optionally between 20 and 100 nm, optionally between 30 and 100 nm.

VII.B.4.b. Another aspect of the invention is a lubricity layer deposited by PECVD from a feed gas comprising a monocyclic siloxane, a monocyclic silazane, a polycyclic siloxane, a polycyclic silazane, or any combination of two or more of these. The coating has an atomic concentration of carbon, normalized to 100% of carbon, oxygen, and silicon, as determined by X-ray photoelectron spectroscopy (XPS), greater than the atomic concentration of carbon in the atomic formula for the feed gas. Optionally, the coating meets the limitations of embodiments VII.B.4.a or VII.B.4.b.A.

VII.B.4.b. Optionally, the atomic concentration of carbon increases by from 1 to 80 atomic percent (as calculated and based on the XPS conditions in Example 13), alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

VII.B.4.b. An additional aspect of the invention is a lubricity layer deposited by PECVD from a feed gas comprising a monocyclic siloxane, a monocyclic silazane, a polycyclic siloxane, a polycyclic silazane, or any combination of two or more of these. The coating has an atomic concentration of silicon, normalized to 100% of carbon, oxygen, and silicon, as determined by X-ray photoelectron spectroscopy (XPS), less than the atomic concentration of silicon in the atomic formula for the feed gas. Optionally, the coating meets the limitations of embodiments VII.B.4.a or VII.B.4.b.A.

VII.B.4.b. Optionally, the atomic concentration of silicon decreases by from 1 to 80 atomic percent (as calculated and based on the XPS conditions in Example 13), alternatively from 10 to 70 atomic percent, alternatively from 20 to 60 atomic percent, alternatively from 30 to 55 atomic percent, alternatively from 40 to 50 atomic percent, alternatively from 42 to 46 atomic percent.

VII.B.4.b. Lubricity layers having combinations of any two or more properties recited in Section VII.B.4 are also expressly contemplated.

VII.C. Vessels Generally

VII.C. A coated vessel or container as described herein and/or prepared according to a method described herein can be used for reception and/or storage and/or delivery of a compound or composition. The compound or composition can be sensitive, for example air-sensitive, oxygen-sensitive, sensitive to humidity and/or sensitive to mechanical influences. It can be a biologically active compound or composition, for example a medicament like insulin or a composition comprising insulin. In another aspect, it can be a biological fluid, optionally a bodily fluid, for example blood or a blood fraction. In certain aspects of the present invention, the compound or composition is a product to be administrated to a subject in need thereof, for example a product to be injected, like blood (as in transfusion of blood from a donor to a recipient or reintroduction of blood from a patient back to the patient) or insulin.

VII.C. A coated vessel or container as described herein and/or prepared according to a method described herein can further be used for protecting a compound or composition contained in its interior space against mechanical and/or chemical effects of the contact surface of the uncoated vessel material. For example, it can be used for preventing or reducing precipitation and/or clotting or platelet activation of the compound or a component of the composition, for example insulin precipitation or blood clotting or platelet activation.

VII.C. It can further be used for protecting a compound or composition contained in its interior against the environment outside of the vessel, for example by preventing or reducing the entry of one or more compounds from the environment surrounding the vessel into the interior space of the vessel. Such environmental compound can be a gas or liquid, for example an atmospheric gas or liquid containing oxygen, air, and/or water vapor.

VII.C. A coated vessel as described herein can also be evacuated and stored in an evacuated state. For example, the coating allows better maintenance of the vacuum in comparison to a corresponding uncoated vessel. In one aspect of this embodiment, the coated vessel is a blood collection tube. The tube can also contain an agent for preventing blood clotting or platelet activation, for example EDTA or heparin.

VII.C. Any of the above-described embodiments can be made, for example, by providing as the vessel a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the probe and the vessel can be useful during coating formation. This can be done, for example, by moving the vessel with respect to the probe or moving the probe with respect to the vessel.

VII.C. In these embodiments, it is contemplated that the coating can be thinner or less complete than can be preferred for a barrier coating, as the vessel in some embodiments will not require the high barrier integrity of an evacuated blood collection tube.

VII.C. As an optional feature of any of the foregoing embodiments the vessel has a central axis.

VII.C. As an optional feature of any of the foregoing embodiments the vessel wall is sufficiently flexible to be flexed at least once at 20° C., without breaking the wall, over a range from at least substantially straight to a bending radius at the central axis of not more than 100 times as great as the outer diameter of the vessel.

VII.C. As an optional feature of any of the foregoing embodiments the bending radius at the central axis is not more than 90 times as great as, or not more than 80 times as great as, or not more than 70 times as great as, or not more than 60 times as great as, or not more than 50 times as great as, or not more than 40 times as great as, or not more than 30 times as great as, or not more than 20 times as great as, or not more than 10 times as great as, or not more than 9 times as great as, or not more than 8 times as great as, or not more than 7 times as great as, or not more than 6 times as great as, or not more than 5 times as great as, or not more than 4 times as great as, or not more than 3 times as great as, or not more than 2 times as great as, or not more than, the outer diameter of the vessel.

VII.C. As an optional feature of any of the foregoing embodiments the vessel wall can be a fluid-contacting contact surface made of flexible material.

VII.C. As an optional feature of any of the foregoing embodiments the vessel lumen can be the fluid flow passage of a pump.

VII.C. As an optional feature of any of the foregoing embodiments the vessel can be a blood bag adapted to maintain blood in good condition for medical use.

VII.C., VII.D. As an optional feature of any of the foregoing embodiments the polymeric material can be a silicone elastomer or a thermoplastic polyurethane, as two examples, or any material suitable for contact with blood, or with insulin.

VII.C., VII.D. In an optional embodiment, the vessel has an inner diameter of at least 2 mm, or at least 4 mm.

VII.C. As an optional feature of any of the foregoing embodiments the vessel is a tube.

VII.C. As an optional feature of any of the foregoing embodiments the lumen has at least two open ends.

VII.C.1. Vessel Containing Viable Blood, Having a Coating Deposited from an Organosilicon Precursor VII.C.1. Even another embodiment is a blood containing vessel. Several non-limiting examples of such a vessel are a blood transfusion bag, a blood sample collection vessel in which a sample has been collected, the tubing of a heart-lung machine, a flexible-walled blood collection bag, or tubing used to collect a patient's blood during surgery and reintroduce the blood into the patient's vasculature. If the vessel includes a pump for pumping blood, a particularly suitable pump is a centrifugal pump or a peristaltic pump. The vessel has a wall; the wall has an inner contact surface defining a lumen. The inner contact surface of the wall has an at least partial coating of a hydrophobic layer, characterized as defined in the Definition Section. The coating can be as thin as monomolecular thickness or as thick as about 1000 nm. The vessel contains blood viable for return to the vascular system of a patient disposed within the lumen in contact with the hydrophobic layer.

VII.C.1. An embodiment is a blood containing vessel including a wall and having an inner contact surface defining a lumen. The inner contact surface has an at least partial coating of a hydrophobic layer. The coating can also comprise or consist essentially of $SiO_x$, where x is as defined in this specification. The thickness of the coating is within the range from monomolecular thickness to about 1000 nm thick on the inner contact surface. The vessel contains blood viable for return to the vascular system of a patient disposed within the lumen in contact with the hydrophobic layer.

VII.C.2. Coating Deposited from an Organosilicon Precursor Reduces Clotting or Platelet Activation of Blood in the Vessel VII.C.2. Another embodiment is a vessel having a wall. The wall has an inner contact surface defining a lumen and has an at least partial coating of a hydrophobic layer, where optionally w, x, y, and z are as previously defined in the Definition Section. The thickness of the coating is from monomolecular thickness to about 1000 nm thick on the inner contact surface. The coating is effective to reduce the clotting or platelet activation of blood exposed to the inner contact surface, compared to the same type of wall uncoated with a hydrophobic layer.

VII.C.2. It is contemplated that the incorporation of a hydrophobic layer will reduce the adhesion or clot forming tendency of the blood, as compared to its properties in contact with an unmodified polymeric or $SiO_x$ contact surface. This property is contemplated to reduce or potentially eliminate the need for treating the blood with heparin, as by reducing the necessary blood concentration of heparin in a patient undergoing surgery of a type requiring blood to be removed from the patient and then returned to the patient, as when using a heart-lung machine during cardiac surgery. It is contemplated that this will reduce the complications of surgery involving the passage of blood through such a vessel, by reducing the bleeding complications resulting from the use of heparin.

VII.C.2. Another embodiment is a vessel including a wall and having an inner contact surface defining a lumen. The inner contact surface has an at least partial coating of a hydrophobic layer, the thickness of the coating being from monomolecular thickness to about 1000 nm thick on the inner contact surface, the coating being effective to reduce the clotting or platelet activation of blood exposed to the inner contact surface.

VII.C.3. Vessel Containing Viable Blood, Having a Coating of Group III or IV Element VII.C.3. Another embodiment is a blood containing vessel having a wall having an inner contact surface defining a lumen. The inner contact surface has an at least partial coating of a composition comprising one or more elements of Group III, one or more elements of Group IV, or a combination of two or more of these. The thickness of the coating is between monomolecular thickness and about 1000 nm thick, inclusive, on the inner contact surface. The vessel contains blood viable for return to the vascular system of a patient disposed within the lumen in contact with the hydrophobic layer.

VII.C.4. Coating of Group III or IV Element Reduces Clotting or Platelet Activation of Blood in the Vessel VII.C.4. Optionally, in the vessel of the preceding paragraph, the coating of the Group III or IV Element is effective to reduce the clotting or platelet activation of blood exposed to the inner contact surface of the vessel wall.

VII.D. Pharmaceutical Delivery Vessels

VII.D. A coated vessel or container as described herein can be used for preventing or reducing the escape of a compound or composition contained in the vessel into the environment surrounding the vessel.

Further uses of the coating and vessel as described herein, which are apparent from any part of the description and claims, are also contemplated.

VII.D.1. Vessel Containing Insulin, Having a Coating Deposited from an Organosilicon Precursor VII.D.1. Another embodiment is an insulin containing vessel including a wall having an inner contact surface defining a lumen. The inner contact surface has an at least partial coating of a hydrophobic layer, characterized as defined in the Definition Section. The coating can be from monomolecular thickness to about 1000 nm thick on the inner contact surface. Insulin is disposed within the lumen in contact with the $Si_wO_xC_yH_z$ coating.

VII.D.1. Still another embodiment is an insulin containing vessel including a wall and having an inner contact surface defining a lumen. The inner contact surface has an at least partial coating of a hydrophobic layer, characterized as defined in the Definition Section, the thickness of the coating being from monomolecular thickness to about 1000 nm thick on the inner contact surface. Insulin, for example pharmaceutical insulin FDA approved for human use, is disposed within the lumen in contact with the hydrophobic layer.

VII.D.1. It is contemplated that the incorporation of a hydrophobic layer, characterized as defined in the Definition Section, will reduce the adhesion or precipitation forming tendency of the insulin in a delivery tube of an insulin pump, as compared to its properties in contact with an unmodified polymeric contact surface. This property is contemplated to reduce or potentially eliminate the need for filtering the insulin passing through the delivery tube to remove a solid precipitate.

VII.D.2. Coating Deposited from an Organosilicon Precursor Reduces Precipitation of Insulin in the Vessel VII.D.2. Optionally, in the vessel of the preceding paragraph, the coating of a hydrophobic layer is effective to reduce the formation of a precipitate from insulin contacting the inner contact surface, compared to the same contact surface absent the hydrophobic layer.

VII.D.2. Even another embodiment is a vessel again comprising a wall and having an inner contact surface defining a lumen. The inner contact surface includes an at least partial coating of a hydrophobic layer. The thickness of the coating is in the range from monomolecular thickness to about 1000 nm thick on the inner contact surface. The coating is effective to reduce the formation of a precipitate from insulin contacting the inner contact surface.

VII.D.3. Vessel Containing Insulin, Having a Coating of Group III or IV Element

VII.D.3. Another embodiment is an insulin containing vessel including a wall having an inner contact surface defining a lumen. The inner contact surface has an at least partial coating of a composition comprising carbon, one or more elements of Group III, one or more elements of Group IV, or a combination of two or more of these. The coating can be from monomolecular thickness to about 1000 nm thick on the inner contact surface. Insulin is disposed within the lumen in contact with the coating.

VII.D.4. Coating of Group III or IV Element Reduces Precipitation of Insulin in the Vessel VII.D.4. Optionally, in the vessel of the preceding paragraph, the coating of a composition comprising carbon, one or more elements of Group III, one or more elements of Group IV, or a combination of two or more of these, is effective to reduce the formation of a precipitate from insulin contacting the inner contact surface, compared to the same contact surface absent the coating.

Other Types of Medical Devices

A wide variety of medical devices having one or more coatings as defined in the present disclosure are contemplated. Some specific examples of such devices follow.

Anesthesia ventilators are contemplated employing an $SiO_x$ barrier coating on a bellows cylinder. The ventilator cylinders can be $SiO_x$ coated to eliminate gas diffusion.

Buccal sample cassettes are contemplated employing an $SiO_x$ barrier.

Capillary Blood Collection devices are contemplated employing an $SiO_x$ barrier to keep constituents of the device wall from leaching into the blood or vice versa.

Centrifuge components, in particular centrifuge vials, tubes, or other containers are contemplated employing an $SiO_x$ barrier to provide reduced plastic contamination.

Containers are contemplated employing an $SiO_x$ barrier where plastic contamination control or $O_2$ barrier control is desirable.

Drug-Eluting Stents, for example Self-Expandable Metallic Stents, Vascular Ring Connectors, and Vascular Stents are contemplated employing an $SiO_xC_y$ or $SiN_xC_y$ controlled porosity layer to control the rate of drug elution from the stent.

Inhalers are contemplated employing an $SiO_x$ barrier. A coated plastic tube in the device inhibits vapor absorption.

Insulin pens are contemplated employing an $SiO_x$ barrier coated cartridge, analogous to the coating contemplated for the barrel of a syringe.

Insulin pumps are contemplated employing an $SiO_x$ barrier to improve delivery and provide a barrier in the reservoir of the pump.

IV Adapters are contemplated employing an $SiO_x$ barrier to prevent plastic extraction into blood.

Medical ventilators are contemplated employing an $SiO_x$ antifog layer to prevent the facemask from fogging in use.

Pipettes are contemplated employing an $SiO_x$ barrier coating.

Sample collection containers are contemplated employing an $SiO_x$ wetting/barrier coating.

Sample Collection Tubes and Storage Devices are contemplated employing an $SiO_x$ wetting/barrier coating.

Shaker flasks are contemplated employing an $SiO_x$ barrier coating for reduced leaching to or from their glass or plastic walls.

Tissue grinders are contemplated employing an $SiO_x$ abrasion/barrier coating, at least in the grinder container.

Urine sample cassettes are contemplated employing an $SiO_x$ barrier coating in the sample container, as explained above for sample containers generally.

Ankle replacements are contemplated employing an $SiO_x$ coating on the metal/ceramic prosthesis.

Implanted cardiac devices such as Artificial Pacemakers and Defibrillators and associated parts are contemplated employing an $SiO_x$ barrier coating.

An artificial pancreas is contemplated employing an $SiO_x$ barrier coating.

Atherectomy catheters are contemplated employing an $SiO_x$ hard/wettable coating. Atherectomy is a procedure that utilizes a catheter with a sharp blade on the end to remove plaque from a blood vessel.

Cell Lifters, Cell Scrapers, and Cell Spreaders, which are polyethylene molded devices for recombinant cell removal, are contemplated employing an $SiO_x$ barrier coating to prevent plastic/additives contamination.

Cornea implants are contemplated employing an $SiO_x$ barrier coating to prevent plastic extractables in the eye.

Cover glasses are contemplated employing an $SiO_x$ barrier coating to provide reduced Na, K, and B leaching into a sample.

Plastic depression microscopic slides are contemplated employing an $SiO_x$ barrier coating for reduced interaction with plastic additives.

Direct Testing and Serology devices are contemplated employing an $SiO_x$ barrier coating for plastic extractables control.

Flat plastic microscopic slides are contemplated employing an $SiO_x$ barrier coating for control of plastic contact (wettability).

Glaucoma valves made of plastic are contemplated employing an $SiO_x$ hydrophilic coating for improved wettability of plastic.

Hip Prostheses and re-constructive prosthesis replacements, other joint and cartilage replacements, and orthopedic implants, such as for the hand, knee, and shoulder are contemplated, optionally employing a thick (more than one micron, alternatively several microns) $SiO_x$ anti-wear coating on the metal/plastic sleeve or other wear parts.

Medicine and contraceptive implants and implantable devices, for example sub-dermal implants are contemplated employing an $SiO_xC_y$ or $SiN_xC_y$ controlled porosity layer to provide controlled release of the medicine.

Lancets, scalpels, razor blades, and sewing and hypodermic needles are contemplated employing an $SiO_xC_y$ or $SiN_xC_y$ lubricity layer to facilitate piercing skin and other tissues and objects and reduce friction.

Medical grafting material such as excised skin is contemplated employing an $SiO_x$ barrier coating to retain moisture. It is contemplated as one alternative that the barrier coating would dissolve when the grafting material was applied, due to contact with body fluids or pretreatment, so it would not impede fluid exchange.

Microtiter plates made of plastic are contemplated employing an $SiO_x$ barrier coating.

Molecular Diagnostics devices such as "lab on chip" devices, microsensors and nanosensors are contemplated employing an $SiO_x$ gas barrier coating and/or an $SiO_xC_y$ or $SiN_xC_y$ hydrophobic layer as a water barrier.

Mycobacteria Testing Devices such as growth indicator tubes are contemplated employing an $SiO_x$ wettability coating, for improved performance.

Catheters, for example Angioplasty Catheters, Urethral Catheters, and Peripherally Inserted Central Catheters (PICCs) are contemplated employing an $SiO_xC_y$ or $SiN_xC_y$ lubricity layer to ease insertion and removal and reduce friction.

Shunt (medical) skin implants are contemplated employing an $SiO_x$ wettability coating.

Stent grafts and Stents are contemplated employing an $SiO_x$ wettability coating to provide improved in vivo grafting.

Transdermal implants are contemplated employing an $SiO_xC_y$ or $SiN_xC_y$ controlled porosity layer.

Ultrasonic nebulizers are contemplated employing an $SiO_xC_y$ or $SiN_xC_y$ controlled porosity or hydrophobic layer to control drop size.

Unicompartmental knee arthroplasty devices are contemplated employing a thick $SiO_x$ anti-wear coating.

Microchip implants (for humans or animals) are contemplated employing a diamond-like carbon (DLC)-based water and water vapor barrier.

Needleless and conventional IV Connectors are contemplated employing an $SiO_xC_y$ or $SiN_xC_y$ lubricity layer to reduce the necessary connection and disconnection force. The $SiO_xC_y$ or $SiN_xC_y$ layer can optionally be supplemented with a silver antimicrobial layer and/or an $SiO_x$ barrier coating to prevent plastic extract into blood.

Auditory brainstem implants are contemplated employing a diamond-like carbon (DLC) based water and water vapor barrier, particularly for the implanted sensor or power unit.

Goggles are contemplated employing an $SiO_xC_y$ or $SiN_xC_y$ hydrophobic layer to provide antifogging lenses.

Stains and Reagents in encapsulated or particulate form are contemplated employing an $SiO_xC_y$ or $SiN_xC_y$ controlled porosity layer to provide controlled encapsulation/release.

Prostatic stents are contemplated employing an $SiO_xC_y$ or $SiN_xC_y$ controlled porosity layer to provide controlled release of material.

Sutures and surgical staples are contemplated employing an $SiO_xC_y$ or $SiN_xC_y$ lubricity layer to make them slide more easily when inserted and removed.

Dehydrated Culture Media devices are contemplated employing an $SiO_x$ barrier coating so their plastic constituents do not extract into culture media.

Cochlear implants are contemplated employing an $SiO_x$ barrier coating to prevent the ingress of ear wax and body fluids.

Petri dishes are contemplated employing an $SiO_x$ barrier coating.

Sacral nerve stimulator wires and implants are contemplated employing an $SiO_x$ barrier coating.

Peritoneovenous shunts and fluid drains and Portacaval shunts made of plastic are contemplated employing an $SiO_x$ wettability coating.

Surgical microscopes are contemplated employing an $SiO_x$ wetting/barrier coating to prevent fogging of the visual aperture.

Plastic Right-to-Left Shunts are contemplated employing an $SiO_x$ wettability coating.

Static Control Supplies are contemplated employing an $SiO_x$ wettability coating, as adsorbed moisture on the coating will reduce static.

WORKING EXAMPLES

Basic Protocols for Forming and Coating Tubes and Syringe Barrels

The vessels tested in the subsequent working examples were formed and coated according to the exemplary protocols set out in U.S. Pat. No. 7,985,188 as incorporated by reference, except as otherwise indicated in individual examples. Whenever parameter values were changed in comparison to these typical values, this will be indicated in the subsequent working examples. The same applies to the type and composition of the process gas.

Example 1

V. In the following test, hexamethyldisiloxane (HMDSO) was used as the organosilicon ("O—Si") feed to PECVD apparatus of FIG. 1 to apply an $SiO_x$ coating on the internal contact surface of a cyclic olefin copolymer (COC) tube as described in the Protocol for Forming COC Tube. The deposition conditions are summarized in the Protocol for Coating Tube Interior with $SiO_x$ and Table 1. The control was the same type of tube to which no barrier coating was applied. The coated and uncoated tubes were then tested for their oxygen transmission rate (OTR) and their water vapor transmission rate (WVTR).

V. Referring to Table 1, the uncoated COC tube had an OTR of 0.215 cc/tube/day. Tubes A and B subjected to PECVD for 14 seconds had an average OTR of 0.0235 cc/tube/day. These results show that the $SiO_x$ coating provided an oxygen transmission BIF over the uncoated tube of 9.1. In other words, the $SiO_x$ barrier coating reduced the oxygen transmission through the tube to less than one ninth its value without the coating.

V. Tube C subjected to PECVD for 7 seconds had an OTR of 0.026. This result shows that the $SiO_x$ coating provided an OTR BIF over the uncoated tube of 8.3. In other words, the $SiO_x$ barrier coating applied in 7 seconds reduced the oxygen transmission through the tube to less than one eighth of its value without the coating.

V. The relative WVTRs of the same barrier coatings on COC tubes were also measured. The uncoated COC tube had a WVTR of 0.27 mg/tube/day. Tubes A and B subjected to PECVD for 14 seconds had an average WVTR of 0.10 mg/tube/day or less. Tube C subjected to PECVD for 7 seconds had a WVTR of 0.10 mg/tube/day. This result shows that the $SiO_x$ coating provided a water vapor transmission barrier improvement factor (WVTR BIF) over the uncoated tube of about 2.7. This was a surprising result, since the uncoated COC tube already has a very low WVTR.

Example 2

V. A series of PET tubes, made according to the Protocol for Forming PET Tube, were coated with $SiO_x$ according to the Protocol for Coating Tube Interior with $SiO_x$ under the conditions reported in Table 2. Controls were made according to the Protocol for Forming PET Tube, but left uncoated. OTR and WVTR samples of the tubes were prepared by epoxy-sealing the open end of each tube to an aluminum adaptor.

V. In a separate test, using the same type of coated PET tubes, mechanical scratches of various lengths were induced with a steel needle through the interior coating, and the OTR BIF was tested. Controls were either left uncoated or were the same type of coated tube without an induced scratch. The OTR BIF, while diminished, was still improved over uncoated tubes (Table 2A).

V. Tubes were tested for OTR as follows. Each sample/adaptor assembly was fitted onto a MOCON® Oxtran 2/21 Oxygen Permeability Instrument. Samples were allowed to equilibrate to transmission rate steady state (1-3 days) under the following test conditions:
Test Gas: Oxygen
Test Gas Concentration: 100%
Test Gas Humidity: 0% relative humidity
Test Gas Pressure: 760 mmHg
Test Temperature: 23.0° C. (73.4° F.)
Carrier Gas: 98% nitrogen, 2% hydrogen
Carrier Gas Humidity: 0% relative humidity
V. The OTR is reported as average of two determinations in Table 2.

V. Tubes were tested for WVTR as follows. The sample/adaptor assembly was fitted onto a MOCON® Permatran-W 3/31 Water Vapor Permeability Instrument. Samples were allowed to equilibrate to transmission rate steady state (1-3 days) under the following test conditions:
Test Gas: Water Vapor
Test Gas Concentration: NA
Test Gas Humidity: 100% relative humidity
Test Gas Temperature: 37.8(° C.) 100.0(° F.)
Carrier Gas: Dry nitrogen
Carrier Gas Humidity: 0% relative humidity
V. The WVTR is reported as average of two determinations in Table 2.

Example 3

A series of syringe barrels were made according to the Protocol for Forming COC Syringe barrel. The syringe barrels were either barrier coated with $SiO_x$ or not under the conditions reported in the Protocol for Coating COC Syringe barrel Interior with $SiO_x$ modified as indicated in Table 3.

OTR and WVTR samples of the syringe barrels were prepared by epoxy-sealing the open end of each syringe barrel to an aluminum adaptor. Additionally, the syringe barrel capillary ends were sealed with epoxy. The syringe-adapter assemblies were tested for OTR or WVTR in the same manner as the PET tube samples, again using a MOCON® Oxtran 2/21 Oxygen Permeability Instrument and a MOCON® Permatran-W 3/31 Water Vapor Permeability Instrument. The results are reported in Table 3.

Example 4

Composition Measurement of Plasma Coatings Using X-Ray Photoelectron Spectroscopy (XPS)/Electron Spectroscopy for Chemical Analysis (ESCA) Contact Surface Analysis V.A. PET tubes made according to the Protocol for Forming PET Tube and coated according to the Protocol for Coating Tube Interior with $SiO_x$ were cut in half to expose the inner tube contact surface, which was then analyzed using X-ray photoelectron spectroscopy (XPS).

V.A. The XPS data was quantified using relative sensitivity factors and a model which assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth.

V.A. Table 5 provides the atomic ratios of the elements detected. The analytical parameters used in for XPS are as follows:

| | |
|---|---|
| Instrument | PHI Quantum 2000 |
| X-ray source | Monochromated Alk$_\alpha$ 1486.6 eV |
| Acceptance Angle | ±23° |
| Take-off angle | 45° |
| Analysis area | 600 μm |
| Charge Correction | C1s 284.8 eV |
| Ion Gun Conditions | Ar$^+$, 1 keV, 2 × 2 mm raster |
| Sputter Rate | 15.6 Å/min ($SiO_2$ Equivalent) |

V.A. XPS does not detect hydrogen or helium. Values given are normalized to Si=1 for the experimental number (last row) using the elements detected, and to O=1 for the uncoated polyethylene terephthalate calculation and example. Detection limits are approximately 0.05 to 1.0 atomic percent. Values given are alternatively normalized to 100% Si+O+C atoms.

V.A. The Inventive Example has an Si/O ratio of 2.4 indicating an $SiO_x$ composition, with some residual carbon from incomplete oxidation of the coating. This analysis demonstrates the composition of an $SiO_x$ barrier layer applied to a polyethylene terephthalate tube according to the present invention.

V.A. Table 4 shows the thickness of the $SiO_x$ samples, determined using TEM according to the following method. Samples were prepared for Focused Ion Beam (FIB) cross-sectioning by coating the samples with a sputtered layer of platinum (50-100 nm thick) using a K575X Emitech coating system. The coated samples were placed in an FEI FIB200 FIB system. An additional layer of platinum was FIB-deposited by injection of an organometallic gas while rastering the 30 kV gallium ion beam over the area of interest. The area of interest for each sample was chosen to be a location half way down the length of the tube. Thin cross sections measuring approximately 15 μm ("micrometers") long, 2 μm wide and 15 μm deep were extracted from the die contact surface using a proprietary in-situ FIB lift-out technique. The cross sections were attached to a 200 mesh copper TEM grid using FIB-deposited platinum. One or two windows in each section, measuring about 8 μm wide, were thinned to electron transparency using the gallium ion beam of the FEI FIB.

V.C. Cross-sectional image analysis of the prepared samples was performed utilizing a Transmission Electron Microscope (TEM). The imaging data was recorded digitally.

The sample grids were transferred to a Hitachi HF2000 transmission electron microscope. Transmitted electron images were acquired at appropriate magnifications. The relevant instrument settings used during image acquisition are given below.

| | |
|---|---|
| Instrument | Transmission Electron Microscope |
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

Example 5

Plasma Uniformity

V.A. COC syringe barrels made according to the Protocol for Forming COC Syringe barrel were treated using the Protocol for Coating COC Syringe Barrel Interior with $SiO_x$, with the following variations. Three different modes of plasma generation were tested for coating syringe barrels such as 250 with $SiO_x$ films. V.A. In Mode 1, hollow cathode plasma ignition was generated in the gas inlet 310, restricted area 292 and processing vessel lumen 304, and ordinary or non-hollow-cathode plasma was generated in the remainder of the vessel lumen 300.

V.A. In Mode 2, hollow cathode plasma ignition was generated in the restricted area 292 and processing vessel lumen 304, and ordinary or non-hollow-cathode plasma was generated in the remainder of the vessel lumen 300 and gas inlet 310.

V.A. In Mode 3, ordinary or non-hollow-cathode plasma was generated in the entire vessel lumen 300 and gas inlet 310. This was accomplished by ramping up power to quench any hollow cathode ignition. Table 6 shows the conditions used to achieve these modes.

V.A. The syringe barrels 250 were then exposed to a ruthenium oxide staining technique. The stain was made from sodium hypochlorite bleach and Ru$^{(III)}$ chloride hydrate. 0.2 g of Ru$^{(III)}$ chloride hydrate was put into a vial. 10 ml bleach were added and mixed thoroughly until the Ru(III) chloride hydrate dissolved.

V.A. Each syringe barrel was sealed with a plastic Luer seal and 3 drops of the staining mixture were added to each syringe barrel. The syringe barrels were then sealed with aluminum tape and allowed to sit for 30-40 minutes. In each set of syringe barrels tested, at least one uncoated syringe barrel was stained. The syringe barrels were stored with the restricted area 292 facing up.

V.A. Based on the staining, the following conclusions were drawn:

V.A. 1. The stain started to attack the uncoated (or poorly coated) areas within 0.25 hours of exposure.

V.A. 2. Ignition in the restricted area 292 resulted in $SiO_x$ coating of the restricted area 292.

V.A. 3. The best syringe barrel was produced by the test with no hollow cathode plasma ignition in either the gas inlet 310 or the restricted area 292. Only the restricted opening 294 was stained, most likely due to leaking of the stain.

V.A. 4. Staining is a good qualitative tool to guide uniformity work.

V.A. Based on all of the above, we concluded:

V.A. 1. Under the conditions of the test, hollow cathode plasma in either the gas inlet 310 or the restricted area 292 led to poor uniformity of the coating.

V.A. 2. The best uniformity was achieved with no hollow cathode plasma in either the gas inlet 310 or the restricted area 292.

Example 6

Interference Patterns from Reflectance Measurements—Prophetic Example

VI.A. Using a UV-Visible Source (Ocean Optics DH2000-BAL Deuterium Tungsten 200-1000 nm), a fiber optic reflection probe (combination emitter/collector Ocean Optics QR400-7 SR/BX with approximately 3 mm probe area), miniature detector (Ocean Optics HR4000CG UV-NIR Spectrometer), and software converting the spectrometer signal to a transmittance/wavelength graph on a laptop computer, an uncoated PET tube Becton Dickinson (Franklin Lakes, N.J., USA) Product No. 366703 13×75 mm (no additives) is scanned (with the probe emitting and collecting light radially from the centerline of the tube, thus normal to the coated contact surface) both about the inner circumference of the tube and longitudinally along the inner wall of the tube, with the probe, with no observable interference pattern observed. Then a Becton Dickinson Product No. 366703 13×75 mm (no additives) $SiO_x$ plasma-coated BD 366703 tube is coated with a 20 nanometer thick $SiO_2$ coating as described in Protocol for Coating Tube Interior with $SiO_x$. This tube is scanned in a similar manner as the uncoated tube. A clear interference pattern is observed with the coated tube, in which certain wavelengths were reinforced and others canceled in a periodic pattern, indicating the presence of a coating on the PET tube.

Example 7

Enhanced Light Transmission from Integrating Sphere Detection

VI.A. The equipment used was a Xenon light source (Ocean Optics HL-2000-HP-FHSA-20 W output Halogen Lamp Source (185-2000 nm)), an Integrating Sphere detector (Ocean Optics ISP-80-8-I) machined to accept a PET tube into its interior, and HR2000+ES Enhanced Sensitivity UV.VIS spectrometer, with light transmission source and light receiver fiber optic sources (QP600-2-UV-VIS—600 um Premium Optical FIBER, UV/VIS, 2 m), and signal conversion software (SPECTRASUITE—Cross-platform Spectroscopy Operating SOFTWARE). An uncoated PET tube made according to the Protocol for Forming PET Tube was inserted onto a TEFZEL Tube Holder (Puck), and inserted into the integrating sphere. With the Spectrasuite software in absorbance mode, the absorption (at 615 nm) was set to zero. An $SiO_x$ coated tube made according to the Protocol for Forming PET Tube and coated according to the Protocol for Coating Tube Interior with $SiO_x$ (except as varied in Table 16) was then mounted on the puck, inserted into the integrating sphere and the absorbance recorded at 615 nm wavelength. The data is recorded in Table 16.

VI.A. With the $SiO_x$ coated tubes, an increase in absorption relative to the uncoated article was observed; increased coating times resulted in increased absorption. The measurement took less than one second.

VI.A. These spectroscopic methods should not be considered limited by the mode of collection (for example, reflectance vs. transmittance vs. absorbance), the frequency or type of radiation applied, or other parameters.

Example 8

Wetting Tension—Plasma Coated PET Tube Examples

VII.A.1.a.ii. The wetting tension method is a modification of the method described in ASTM D 2578. Wetting tension is a specific measure for the hydrophobicity or hydrophilicity of a contact surface. This method uses standard wetting tension solutions (called dyne solutions) to determine the solution that comes nearest to wetting a plastic film contact surface for exactly two seconds. This is the film's wetting tension.

VII.A.1.a.ii. The procedure utilized is varied from ASTM D 2578 in that the substrates are not flat plastic films, but are tubes made according to the Protocol for Forming PET Tube and (except for controls) coated according to the Protocol for Coating Tube Interior with Hydrophobic layer. A silicone coated glass syringe (Becton Dickinson Hypak® PRTC glass prefillable syringe with Luer-lok® tip) (1 mL) was also tested. The results of this test are listed in Table 10.

VII.A.1.a.ii. Surprisingly, plasma coating of uncoated PET tubes (40 dynes/cm) can achieve either higher (more hydrophilic) or lower (more hydrophobic) energy contact surfaces using the same hexamethyldisiloxane (HMDSO) feed gas, by varying the plasma process conditions. A thin (approximately 20-40 nanometers) $SiO_x$ coating made according to the Protocol for Coating Tube Interior with $SiO_x$ (data not shown in the tables) provides similar wettability as hydrophilic bulk glass substrates. A thin (less than about 100 nanometers) hydrophobic layer made according to the Protocol for Coating Tube Interior with Hydrophobic layer provides similar non-wettability as hydrophobic silicone fluids (data not shown in the tables).

Example 9

Vacuum Retention Study of Tubes Via Accelerated Ageing

VII.A.3 Accelerated ageing offers faster assessment of long term shelf-life products. Accelerated ageing of blood tubes for vacuum retention is described in U.S. Pat. No. 5,792,940, Column 1, Lines 11-49.

VII.A.3 Three types of polyethylene terephthalate (PET) 13×75 mm (0.85 mm thick walls) molded tubes were tested:

Becton Dickinson Product No. 366703 13×75 mm (no additives) tube (shelf life 545 days or 18 months), closed with Hemogard® system red stopper and uncolored guard [commercial control];

PET tubes made according to the Protocol for Forming PET Tube, closed with the same type of Hemogard® system red stopper and uncolored guard [internal control]; and injection molded PET 13×75 mm tubes, made according to the Protocol for Forming PET Tube, coated according to the Protocol for Coating Tube Interior with $SiO_x$ closed with the same type of Hemogard® system red stopper and uncolored guard [inventive sample].

VII.A.3 The BD commercial control was used as received. The internal control and inventive samples were evacuated and capped with the stopper system to provide the desired partial pressure (vacuum) inside the tube after sealing. All samples were placed into a three gallon (3.8 L) 304 SS wide mouth pressure vessel (Sterlitech No. 740340). The pressure vessel was pressurized to 48 psi (3.3 atm, 2482 mm·Hg). Water volume draw change determinations were made by (a) removing 3-5 samples at increasing time intervals, (b) permitting water to draw into the evacuated tubes through a 20 gauge blood collection adaptor from a one liter plastic bottle reservoir, (c) and measuring the mass change before and after water draw.

VII.A.3 Results are indicated on Table 11.

VII.A.3 The Normalized Average Decay Rate is calculated by dividing the time change in mass by the number of pressurization days and initial mass draw [mass change/(days× initial mass)]. The Accelerated Time to 10% Loss (months) is also calculated. Both data are listed in Table 12.

VII.A.3 This data indicates that both the commercial control and uncoated internal control have identical vacuum loss rates, and surprisingly, incorporation of a $SiO_x$ coating on the PET interior walls improves vacuum retention time by a factor of 2.1.

Example 10

Lubricity Layers

VII.B.1.a. The following materials were used in this test:

Commercial (BD Hypak® PRTC) glass prefillable syringes with Luer-lok® tip) (ca 1 mL)

COC syringe barrels made according to the Protocol for Forming COC Syringe barrel;

Commercial plastic syringe plungers with elastomeric tips taken from Becton Dickinson Product No. 306507 (obtained as saline prefilled syringes);

Normal saline solution (taken from the Becton-Dickinson Product No. 306507 prefilled syringes);

Dillon Test Stand with an Advanced Force Gauge (Model AFG-50N)

Syringe holder and drain jig (fabricated to fit the Dillon Test Stand)

VII.B.1.a. The following procedure was used in this test.

VII.B.1.a. The jig was installed on the Dillon Test Stand. The platform probe movement was adjusted to 6 in/min (2.5 mm/sec) and upper and lower stop locations were set. The stop locations were verified using an empty syringe and barrel. The commercial saline-filled syringes were labeled, the plungers were removed, and the saline solution was drained via the open ends of the syringe barrels for re-use. Extra plungers were obtained in the same manner for use with the COC and glass barrels.

VII.B.1.a. Syringe plungers were inserted into the COC syringe barrels so that the second horizontal molding point of each plunger was even with the syringe barrel lip (about 10 mm from the tip end). Using another syringe and needle assembly, the test syringes were filled via the capillary end with 2-3 milliliters of saline solution, with the capillary end uppermost. The sides of the syringe were tapped to remove any large air bubbles at the plunger/fluid interface and along the walls, and any air bubbles were carefully pushed out of the syringe while maintaining the plunger in its vertical orientation.

VII.B.1.a. Each filled syringe barrel/plunger assembly was installed into the syringe jig. The test was initiated by pressing the down switch on the test stand to advance the moving metal hammer toward the plunger. When the moving metal hammer was within 5 mm of contacting the top of the plunger, the data button on the Dillon module was repeatedly tapped to record the force at the time of each data button depression, from before initial contact with the syringe plunger until the plunger was stopped by contact with the front wall of the syringe barrel.

VII.B.1.a. All benchmark and coated syringe barrels were run with five replicates (using a new plunger and barrel for each replicate).

VII.B.1.a. COC syringe barrels made according to the Protocol for Forming COC Syringe barrel were coated with an OMCTS lubricity layer according to the Protocol for Coating COC Syringe Barrel Interior with OMCTS Lubricity layer, assembled and filled with saline, and tested as described above in this Example for lubricity layers. The polypropylene chamber used per the Protocol for Coating COC Syringe Barrel Interior with OMCTS Lubricity layer allowed the OMCTS vapor (and oxygen, if added—see Table 13) to flow through the syringe barrel and through the syringe capillary into the polypropylene chamber (although a lubricity layer is not needed in the capillary section of the syringe in this instance). Several different coating conditions were tested, as shown in previously mentioned Table 13. All of the depositions were completed on COC syringe barrels from the same production batch.

The coated samples were then tested using the plunger sliding force test per the protocol of this Example, yielding the results in Table 13, in English and metric force units. The data shows clearly that low power and no oxygen provided the lowest plunger sliding force for COC and coated COC syringes. Note that when oxygen was added at lower power (6 W) (the lower power being a favorable condition) the plunger sliding force increased from 1.09 lb, 0.49 Kg (at Power=11 W) to 2.27 lb., 1.03 Kg. This indicates that the addition of oxygen can be undesirable in certain circumstances to achieve the lowest possible plunger sliding force.

VII.B.1.a. Note also that the best plunger sliding force (Power=11 W, plunger sliding force=1.09 lb, 0.49 Kg) was very near the current industry standard of silicone coated glass (plunger sliding force=0.58 lb, 0.26 Kg), while avoiding the problems of a glass syringe such as breakability and a more expensive manufacturing process. With additional optimization, values equal to or better than the current glass with silicone performance are expected to be achieved.

VII.B.1.a. The samples were created by coating COC syringe barrels according to the Protocol for Coating COC Syringe Barrel Interior with OMCTS Lubricity layer. An alternative embodiment of the technology herein, would apply the lubricity layer over another thin film coating, such as $SiO_x$, for example applied according to the Protocol for Coating COC Syringe barrel Interior with $SiO_x$.

Example 11

Improved Syringe Barrel Lubricity layer

VII.B.1.a. The force required to expel a 0.9 percent saline payload from a syringe through a capillary opening using a plastic plunger was determined for inner wall-coated syringes.

VII.B.1.a. Three types of COC syringe barrels made according to the Protocol for Forming COC Syringe barrel were tested: one type having no internal coating [Uncoated Control], another type with a hexamethyldisiloxane (HMDSO)-based plasma coated internal wall coating [HMDSO Control] according to the Protocol for Coating COC Syringe Barrel Interior with HMDSO Coating, and a third type with an octamethylcyclotetrasiloxane [OMCTS-Inventive Example]-based plasma coated internal wall coating applied according to the Protocol for Coating COC Syringe Barrel Interior with OMCTS Lubricity layer. Fresh plastic plungers with elastomeric tips taken from BD Product Becton-Dickinson Product No. 306507 were used for all examples. Saline from Product No. 306507 was also used.

VII.B.1.a. The plasma coating method and apparatus for coating the syringe barrel inner walls is described in other experimental sections of this application. The specific coating parameters for the HMDSO-based and OMCTS-based coatings are listed in the Protocol for Coating COC Syringe Barrel Interior with HMDSO Coating, the Protocol for Coating COC Syringe barrel Interior with OMCTS Lubricity layer, and Table 14.

VII.B.1.a. The plunger is inserted into the syringe barrel to about 10 millimeters, followed by vertical filling of the experimental syringe through the open syringe capillary with a separate saline-filled syringe/needle system. When the experimental syringe has been filled into the capillary opening, the syringe is tapped to permit any air bubbles adhering to the inner walls to release and rise through the capillary opening.

VII.B.1.a. The filled experimental syringe barrel/plunger assembly is placed vertically into a home-made hollow metal jig, the syringe assembly being supported on the jig at the finger flanges. The jig has a drain tube at the base and is mounted on Dillon Test Stand with Advanced Force Gauge (Model AFG-50N). The test stand has a metal hammer, moving vertically downward at a rate of six inches (152 millimeters) per minute. The metal hammer contacts the extended plunger expelling the saline solution through the capillary. Once the plunger has contacted the syringe barrel/capillary interface the experiment is stopped.

VII.B.1.a. During downward movement of the metal hammer/extended plunger, resistance force imparted on the hammer as measured on the Force Gauge is recorded on an electronic spreadsheet. From the spreadsheet data, the maximum force for each experiment is identified.

VII.B.1.a. Table 14 lists for each Example the Maximum Force average from replicate coated COC syringe barrels and the Normalized Maximum Force as determined by division of the coated syringe barrel Maximum Force average by the uncoated Maximum Force average.

VII.B.1.a. The data indicates all OMCTS-based inner wall plasma coated COC syringe barrels (Inventive Examples C, E, F, G, H) demonstrate much lower plunger sliding force than uncoated COC syringe barrels (uncoated Control Examples A & D) and surprisingly, also much lower plunger sliding force than HMDSO-based inner wall plasma coated COC syringe barrels (HMDSO control Example B). More surprising, an OMCTS-based coating over a silicon oxide ($SiO_x$) gas barrier coating maintains excellent low plunger sliding force (Inventive Example F). The best plunger sliding force was Example C (Power=8, plunger sliding force=1.1 lb, 0.5 Kg). It was very near the current industry standard of silicone coated glass (plunger sliding force=0.58 lb., 0.26 Kg.), while avoiding the problems of a glass syringe such as breakability and a more expensive manufacturing process. With additional optimization, values equal to or better than the current glass with silicone performance are expected to be achieved.

Example 12

Fabrication of COC Syringe Barrel with Exterior Coating—Prophetic Example

VII.B.1.c. A COC syringe barrel formed according to the Protocol for Forming COC Syringe barrel is sealed at both ends with disposable closures. The capped COC syringe barrel is passed through a bath of Daran® 8100 Saran Latex (Owensboro Specialty Plastics). This latex contains five percent isopropyl alcohol to reduce the contact surface tension of the composition to 32 dynes/cm). The latex composition completely wets the exterior of the COC syringe barrel. After draining for 30 seconds, the coated COC syringe barrel is exposed to a heating schedule comprising 275° F. (135° C.) for 25 seconds (latex coalescence) and 122° F. (50° C.) for four hours (finish cure) in respective forced air ovens. The resulting PVdC film is 1/10 mil (2.5 microns) thick. The COC syringe barrel and PVdC-COC laminate COC syringe barrel are measured for OTR and WVTR using a MOCON brand Oxtran 2/21 Oxygen Permeability Instrument and Permatran-W 3/31 Water Vapor Permeability Instrument, respectively.

VII.B.1.c. Predicted OTR and WVTR values are listed in Table 15, which shows the expected Barrier Improvement Factor (BIF) for the laminate would be 4.3 (OTR-BIF) and 3.0 (WVTR-BIF), respectively.

Example 13

Atomic Compositions of PECVD Applied OMCTS and HMDSO Coatings

VII.B.4. COC syringe barrel samples made according to the Protocol for Forming COC Syringe barrel, coated with OMCTS (according to the Protocol for Coating COC Syringe Barrel Interior with OMCTS Lubricity layer) or coated with HMDSO according to the Protocol for Coating COC Syringe Barrel Interior with HMDSO Coating were provided. The atomic compositions of the coatings derived from OMCTS or HMDSO were characterized using X-Ray Photoelectron Spectroscopy (XPS).

VII.B.4. XPS data is quantified using relative sensitivity factors and a model that assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth.

VII.B.4. The following analytical parameters were used:
Instrument: PHI Quantum 2000
x-ray source: Monochromated Alk$\alpha$ 1486.6 eV
Acceptance Angle +23°

Take-off angle 45°
Analysis area 600 μm
Charge Correction C1s 284.8 eV
Ion Gun Conditions Ar+, 1 keV, 2×2 mm raster
Sputter Rate 15.6 Å/min ($SiO_2$ Equivalent)

VII.B.4. Table 17 provides the atomic concentrations of the elements detected. XPS does not detect hydrogen or helium. Values given are normalized to 100 percent using the elements detected. Detection limits are approximately 0.05 to 1.0 atomic percent.

VII.B.4. From the coating composition results and calculated starting monomer precursor elemental percent in Table 17, while the carbon atom percent of the HMDSO-based coating is decreased relative to starting HMDSO monomer carbon atom percent (54.1% down to 44.4%), surprisingly the OMCTS-based coating carbon atom percent is increased relative to the OMCTS monomer carbon atom percent (34.8% up to 48.4%), an increase of 39 atomic %, calculated as follows:

100% [(48.4/34.8)−1]=39 at. %.

Also, while the silicon atom percent of the HMDSO-based coating is almost unchanged relative to starting HMDSO monomer silicon atom percent (21.8% to 22.2%), surprisingly the OMCTS-based coating silicon atom percent is significantly decreased relative to the OMCTS monomer silicon atom percent (42.0% down to 23.6%), a decrease of 44 atomic %. With both the carbon and silicon changes, the OMCTS monomer to coating behavior does not trend with that observed in common precursor monomers (e.g. HMDSO). See, e.g., Hans J. Griesser, Ronald C. Chatelier, Chris Martin, Zoran R. Vasic, Thomas R. Gengenbach, George Jessup J. Biomed. Mater. Res. (Appl Biomater) 53: 235-243, 2000.

Example 14

Volatile Components from Plasma Coatings ("Outgassing")

VII.B.4. COC syringe barrel samples made according to the Protocol for Forming COC Syringe barrel, coated with OMCTS (according to the Protocol for Coating COC Syringe Barrel Interior with OMCTS Lubricity layer) or with HMDSO (according to the Protocol for Coating COC Syringe Barrel Interior with HMDSO Coating) were provided. Outgassing gas chromatography/mass spectroscopy (GC/MS) analysis was used to measure the volatile components released from the OMCTS or HMDSO coatings.

VII.B.4. The syringe barrel samples (four COC syringe barrels cut in half lengthwise) were placed in one of the 1½" (37 mm) diameter chambers of a dynamic headspace sampling system (CDS 8400 auto-sampler). Prior to sample analysis, a system blank was analyzed. The sample was analyzed on an Agilent 7890A Gas Chromatograph/Agilent 5975 Mass Spectrometer, using the following parameters, producing the data set out in Table 18:

GC Column: 30 m×0.25 mm DB-5MS (J&W Scientific), 0.25 μm film thickness
Flow rate: 1.0 ml/min, constant flow mode
Detector: Mass Selective Detector (MSD)
Injection Mode: Split injection (10:1 split ratio)
Outgassing Conditions: 1½" (37 mm) Chamber, purge for three hour at 85° C., flow 60 ml/min
Oven temperature: 40° C. (5 min.) to 300° C. @10° C./min.; hold for 5 min. at 300° C.

The outgassing results from Table 18 clearly indicated a compositional differentiation between the HMDSO-based and OMCTS-based lubricity layers tested. HMDSO-based compositions outgassed trimethylsilanol [$(Me)_3SiOH$] but outgassed no measured higher oligomers containing repeating -$(Me)_2SiO$— moieties, while OMCTS-based compositions outgassed no measured trimethylsilanol [$(Me)_3SiOH$] but outgassed higher oligomers containing repeating -$(Me)_2SiO$— moieties. It is contemplated that this test can be useful for differentiating HMDSO-based coatings from OMCTS-based coatings.

Without limiting the invention according to the scope or accuracy of the following theory, it is contemplated that this result can be explained by considering the cyclic structure of OMCTS, with only two methyl groups bonded to each silicon atom, versus the acyclic structure of HMDSO, in which each silicon atom is bonded to three methyl groups. OMCTS is contemplated to react by ring opening to form a diradical having repeating -$(Me)_2SiO$— moieties which are already oligomers, and can condense to form higher oligomers. HMDSO, on the other hand, is contemplated to react by cleaving at one O—Si bond, leaving one fragment containing a single O—Si bond that recondenses as $(Me)_3SiOH$ and the other fragment containing no O—Si bond that recondenses as [$(Me)_3Si]_2$.

The cyclic nature of OMCTS is believed to result in ring opening and condensation of these ring-opened moieties with outgassing of higher MW oligomers (26 ng/test). In contrast, HMDSO-based coatings are believed not to provide any higher oligomers, based on the relatively low-molecular-weight fragments from HMDSO.

Example 15

Density Determination of Plasma Coatings Using X-Ray Reflectivity (XRR)

VII. B. 4. Sapphire witness samples (0.5×0.5×0.1 cm) were glued to the inner walls of separate PET tubes, made according to the Protocol for Forming PET tubes. The sapphire witness-containing PET tubes were coated with OMCTS or HMDSO (both according to the Protocol for Coating COC Syringe Barrel Interior with OMCTS Lubricity layer, deviating all with 2× power). The coated sapphire samples were then removed and X-ray reflectivity (XRR) data were acquired on a PANalytical X'Pert diffractometer equipped with a parabolic multilayer incident beam monochromator and a parallel plate diffracted beam collimator. A two layer $Si_wO_xC_yH_z$ model was used to determine coating density from the critical angle measurement results. This model is contemplated to offer the best approach to isolate the true $Si_wO_xC_yH_z$ coating. The results are shown in Table 19.

VII. B. 4. From Table 17 showing the results of Example 13, the lower oxygen (28%) and higher carbon (48.4%) composition of OMCTS versus HMDSO would suggest OMCTS should have a lower density, due to both atomic mass considerations and valency (oxygen=2; carbon=4). Surprisingly, the XRR density results indicate the opposite would be observed, that is, the OMCTS density is higher than HMDSO density.

VII. B. 4. Without limiting the invention according to the scope or accuracy of the following theory, it is contemplated that there is a fundamental difference in reaction mechanism in the formation of the respective HMDSO-based and OMCTS-based coatings. HMDSO fragments can more easily nucleate or react to form dense nanoparticles which then deposit on the contact surface and react further on the contact surface, whereas OMCTS is much less likely to form dense gas phase nanoparticles. OMCTS reactive species are much more likely to condense on the contact surface in a form much more similar to the original OMCTS monomer, resulting in an overall less dense coating.

Example 16

Thickness Uniformity of PECVD Applied Coatings

VII. B. 4. Samples were provided of COC syringe barrels made according to the Protocol for Forming COC Syringe barrel and respectively coated with $SiO_x$ according to the Protocol for Coating COC Syringe Barrel Interior with $SiO_x$ or an OMCTS-based lubricity layer according to the Protocol for Coating COC Syringe Barrel Interior with OMCTS Lubricity layer. Samples were also provided of PET tubes made according to the Protocol for Forming PET Tube, respectively coated and uncoated with $SiO_x$ according to the Protocol for Coating Tube Interior with $SiO_x$ and subjected to an accelerated aging test. Transmission electron microscopy (TEM) was used to measure the thickness of the PECVD-applied coatings on the samples. The previously stated TEM procedure of Example 4 was used. The method and apparatus described by the $SiO_x$ and lubricity layer protocols used in this example demonstrated uniform coating as shown in Table 20.

Example 17

Outgassing Measurement on COC

VI.B. COC tubes were made according to the Protocol for Forming COC Tube. Some of the tubes were provided with an interior barrier coating of $SiO_x$ according to the Protocol for Coating Tube Interior with $SiO_x$, and other COC tubes were uncoated. Commercial glass blood collection Becton Dickinson 13×75 mm tubes having similar dimensions were also provided as above. The tubes were stored for about 15 minutes in a room containing ambient air at 45% relative humidity and 70° F. (21° C.), and the following testing was done at the same ambient relative humidity. The tubes were tested for outgassing following the ATC microflow measurement procedure and equipment of Example 8 (an Intelligent Gas Leak System with Leak Test Instrument Model ME2, with second generation IMFS sensor, (10µ/min full range), Absolute Pressure Sensor range: 0-10 Torr, Flow measurement uncertainty: +/−5% of reading, at calibrated range, employing the Leak-Tek Program for automatic data acquisition (with PC) and signatures/plots of leak flow vs. time). In the present case each tube was subjected to a 22-second bulk moisture degassing step at a pressure of 1 mm Hg, was pressurized with nitrogen gas for 2 seconds (to 760 millimeters Hg), then the nitrogen gas was pumped down and the microflow measurement step was carried out for about one minute at 1 millimeter Hg pressure.

Again, the outgassing measurement began at about 4 seconds, and a few seconds later the plots for the uncoated COC tubes and the plots for the $SiO_x$ barrier coated tubes clearly diverged, again demonstrating rapid differentiation between barrier coated tubes and uncoated tubes. A consistent separation of uncoated COC (>2 micrograms at 60 seconds) versus $SiO_x$-coated COC (less than 1.6 micrograms at 60 seconds) was realized.

Example 18

Lubricity Layers

VII.B.1.a. COC syringe barrels made according to the Protocol for Forming COC Syringe Barrel were coated with a lubricity layer according to the Protocol for Coating COC Syringe Barrel Interior with OMCTS Lubricity layer. The results are provided in Table 21. The results show that the trend of increasing the power level, in the absence of oxygen, from 8 to 14 Watts was to improve the lubricity of the coating. Further experiments with power and flow rates can provide further enhancement of lubricity.

Example 19

Lubricity Layers—Hypothetical Example

VII. B. 4. Injection molded cyclic olefin copolymer (COC) plastic syringe barrels are made according to the Protocol for Forming COC Syringe Barrel. Some are uncoated ("control") and others are PECVD lubricity coated according to the Protocol for Coating COC Syringe Barrel Interior with OMCTS Lubricity layer ("lubricated syringe"). The lubricated syringes and controls are tested to measure the force to initiate movement of the plunger in the barrel (breakout force) and the force to maintain movement of the plunger in the barrel (plunger sliding force) using a Genesis Packaging Automated Syringe Force Tester, Model AST.

VII. B. 4. The test is a modified version of the ISO 7886-1:1993 test. The following procedure is used for each test. A fresh plastic plunger with elastomeric tip taken from Becton Dickinson Product No. 306507 (obtained as saline prefilled syringes) is removed from the syringe assembly. The elastomeric tip is dried with clean dry compressed air. The elastomeric tip and plastic plunger are then inserted into the COC plastic syringe barrel to be tested with the plunger positioned even with the bottom of the syringe barrel. The filled syringes are then conditioned as necessary to achieve the state to be tested. For example, if the test object is to find out the effect of lubricant coating on the breakout force of syringes after storing the syringes for three months, the syringes are stored for three months to achieve the desired state.

VII. B. 4. The syringe is installed into a Genesis Packaging Automated Syringe Force Tester. The tester is calibrated at the start of the test per the manufacturer's specification. The tester input variables are Speed=100 mm/minute, Range=10, 000. The start button is pushed on the tester. At completion of the test, the breakout force (to initiate movement of the plunger in the barrel) and the plunger sliding force (to maintain movement) are measured, and are found to be substantially lower for the lubricated syringes than for the control syringes.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

TABLE 1

COATED COC TUBE OTR AND WVTR MEASUREMENT

| Coating ID | Power (Watts) | O—Si | O—Si Flow (sccm) | O₂ Flow (sccm) | Time (sec) | OTR (cc/ Tube. Day) | WVTR (mg/ Tube. Day) |
|---|---|---|---|---|---|---|---|
| No Coating | | | | | | 0.215 | 0.27 |
| A | 50 | HMDSO | 6 | 90 | 14 | 0.023 | 0.07 |
| B | 50 | HMDSO | 6 | 90 | 14 | 0.024 | 0.10 |
| C | 50 | HMDSO | 6 | 90 | 7 | 0.026 | 0.10 |

TABLE 2

COATED PET TUBE OTR AND WVTR MEASUREMENT

| Coating ID | Power (Watts) | O—Si | O—Si Flow (sccm) | O₂ Flow (sccm) | Time (sec) | OTR (cc/ Tube. Day) | WVTR (mg/ Tube. Day) | BIF (OTR) | BIF (WVTR) |
|---|---|---|---|---|---|---|---|---|---|
| Uncoated Control | | | | | | 0.0078 | 3.65 | — | — |
| SiO$_x$ | 50 | HMDSO | 6 | 90 | 3 | 0.0035 | 1.95 | 2.2 | 1.9 |

TABLE 2A

COATED PET TUBE OTR WITH MECHANICAL SCRATCH DEFECTS

| Example | O—Si | Power (Watts) | O—Si Flow (sccm) | O₂ Flow (sccm) | Treat Time (sec) | Mechanical Scratch Length (mm) | OTR (cc/tube. day)* | OTR BIF |
|---|---|---|---|---|---|---|---|---|
| Uncoated Control | | | | | | | 0.0052 | |
| Inventive | HMDSO | 50 | 6 | 90 | 3 | 0 | 0.0014 | 3.7 |
| Inventive | HMDSO | 50 | 6 | 90 | 3 | 1 | 0.0039 | 1.3 |
| Inventive | HMDSO | 50 | 6 | 90 | 3 | 2 | 0.0041 | 1.3 |
| Inventive | HMDSO | 50 | 6 | 90 | 3 | 10 | 0.0040 | 1.3 |
| Inventive | HMDSO | 50 | 6 | 90 | 3 | 20 | 0.0037 | 1.4 |

*average of two tubes

TABLE 3

COATED COC SYRINGE BARREL OTR AND WVTR MEASUREMENT

| Example | Syringe Coating | O—Si Composition | Power (Watts) | O—Si Flow Rate (sccm) | O₂ Flow Rate (sccm) | Coating Time (sec) | OTR (cc/ Barrel. Day) | WVTR (mg/ Barrel. Day) | BIF (OTR) | BIF (WVTR) |
|---|---|---|---|---|---|---|---|---|---|---|
| A | Uncoated Control | | | | | | 0.032 | 0.12 | | |
| B | SiO$_x$ Inventive Example | HMDSO | 44 | 6 | 90 | 7 | 0.025 | 0.11 | 1.3 | 1.1 |
| C | SiO$_x$ Inventive Example | HMDSO | 44 | 6 | 105 | 7 | 0.021 | 0.11 | 1.5 | 1.1 |
| D | SiO$_x$ Inventive Example | HMDSO | 50 | 6 | 90 | 7 | 0.026 | 0.10 | 1.2 | 1.2 |
| E | SiO$_x$ Inventive Example | HMDSO | 50 | 6 | 90 | 14 | 0.024 | 0.07 | 1.3 | 1.7 |
| F | SiO$_x$ Inventive Example | HMDSO | 52 | 6 | 97.5 | 7 | 0.022 | 0.12 | 1.5 | 1.0 |
| G | SiO$_x$ Inventive Example | HMDSO | 61 | 6 | 105 | 7 | 0.022 | 0.11 | 1.4 | 1.1 |
| H | SiO$_x$ Inventive Example | HMDSO | 61 | 6 | 120 | 7 | 0.024 | 0.10 | 1.3 | 1.2 |

TABLE 3-continued

COATED COC SYRINGE BARREL OTR AND WVTR MEASUREMENT

| Example | Syringe Coating | O—Si Composition | Power (Watts) | O—Si Flow Rate (sccm) | $O_2$ Flow Rate (sccm) | Coating Time (sec) | OTR (cc/ Barrel. Day) | WVTR (mg/ Barrel. Day) | BIF (OTR) | BIF (WVTR) |
|---|---|---|---|---|---|---|---|---|---|---|
| I | $SiO_x$ Inventive Example | HMDZ | 44 | 6 | 90 | 7 | 0.022 | 0.10 | 1.5 | 1.3 |
| J | $SiO_x$ Inventive Example | HMDZ | 61 | 6 | 90 | 7 | 0.022 | 0.10 | 1.5 | 1.2 |
| K | $SiO_x$ Inventive Example | HMDZ | 61 | 6 | 105 | 7 | 0.019 | 0.10 | 1.7 | 1.2 |

TABLE 4

$SiO_x$ COATING THICKNESS (NANOMETERS) DETECTED BY TEM

| Sample | O—Si | Thickness (nm) | Power (Watts) | HMDSO Flow Rate (sccm) | Oxygen Flow Rate (sccm) |
|---|---|---|---|---|---|
| Inventive Example A | HMDSO | 25-50 | 39 | 6 | 60 |
| Inventive Example B | HMDSO | 20-35 | 39 | 6 | 90 |

TABLE 5

ATOMIC RATIOS OF THE ELEMENTS DETECTED (in parentheses, Concentrations in percent, normalized to 100% of elements detected)

| Sample | Plasma Coating | Si | O | C |
|---|---|---|---|---|
| PET Tube - Comparative Example | — | 0.08 (4.6%) | 1 (31.5%) | 2.7 (63.9%) |
| Polyethylene Terephthalate - Calculated | — | | 1 (28.6%) | 2.5 (71.4%) |
| Coated PET Tube - Inventive Example | $SiO_x$ | 1 (39.1%) | 2.4 (51.7%) | 0.57 (9.2%) |

TABLE 6

EXTENT OF HOLLOW CATHODE PLASMA IGNITION

| Sample | Power | Time | Hollow Cathode Plasma Ignition | Staining Result |
|---|---|---|---|---|
| A | 25 Watts | 7 sec | No Ignition in gas inlet 310, Ignition in restricted area 292 | good |
| B | 25 Watts | 7 sec | Ignition in gas inlet 310 and restricted area 292 | poor |
| C | 8 Watts | 9 sec | No Ignition in gas inlet 310, Ignition in restricted area 292 | better |
| D | 30 Watts | 5 sec | No Ignition in gas inlet 310 or restricted area 292 | best |

TABLE 7

FLOW RATE USING GLASS TUBES

| Glass Tube | Run #1 (μg/min.) | Run #2 (μg/min.) | Average (μg/min.) |
|---|---|---|---|
| 1 | 1.391 | 1.453 | 1.422 |
| 2 | 1.437 | 1.243 | 1.34 |
| 3 | 1.468 | 1.151 | 1.3095 |
| 4 | 1.473 | 1.019 | 1.246 |
| 5 | 1.408 | 0.994 | 1.201 |
| 6 | 1.328 | 0.981 | 1.1545 |
| 7 | Broken | Broken | Broken |
| 8 | 1.347 | 0.909 | 1.128 |
| 9 | 1.171 | 0.91 | 1.0405 |
| 10 | 1.321 | 0.946 | 1.1335 |
| 11 | 1.15 | 0.947 | 1.0485 |
| 12 | 1.36 | 1.012 | 1.186 |
| 13 | 1.379 | 0.932 | 1.1555 |
| 14 | 1.311 | 0.893 | 1.102 |
| 15 | 1.264 | 0.928 | 1.096 |
| Average | 1.343 | 1.023 | 1.183 |
| Max | 1.473 | 1.453 | 1.422 |
| Min | 1.15 | 0.893 | 1.0405 |
| Max – Min | 0.323 | 0.56 | 0.3815 |
| Std Dev | 0.097781 | 0.157895 | 0.1115087 |

TABLE 8

FLOW RATE USING PET TUBES

| Uncoated PET | Run #1 (μg/min.) | Run #2 (μg/min.) | Average (μg/min.) |
|---|---|---|---|
| 1 | 10.36 | 10.72 | 10.54 |
| 2 | 11.28 | 11.1 | 11.19 |
| 3 | 11.43 | 11.22 | 11.325 |
| 4 | 11.41 | 11.13 | 11.27 |
| 5 | 11.45 | 11.17 | 11.31 |
| 6 | 11.37 | 11.26 | 11.315 |
| 7 | 11.36 | 11.33 | 11.345 |
| 8 | 11.23 | 11.24 | 11.235 |
| 9 | 11.14 | 11.23 | 11.185 |
| 10 | 11.1 | 11.14 | 11.12 |
| 11 | 11.16 | 11.25 | 11.205 |
| 12 | 11.21 | 11.31 | 11.26 |
| 13 | 11.28 | 11.22 | 11.25 |
| 14 | 10.99 | 11.19 | 11.09 |
| 15 | 11.3 | 11.24 | 11.27 |
| Average | 11.205 | 11.183 | 11.194 |
| Max | 11.45 | 11.33 | 11.345 |
| Min | 10.36 | 10.72 | 10.54 |
| Max – Min | 1.09 | 0.61 | 0.805 |
| Std Dev | 0.267578 | 0.142862 | 0.195121 |

TABLE 9

FLOW RATE FOR SiOx COATED PET TUBES

| Coated PET | Run #1 (μg/min.) | Run #2 (μg/min.) | Average (μg/min.) |
|---|---|---|---|
| 1 | 6.834 | 6.655 | 6.7445 |
| 2 | 9.682 | 9.513 | Outliers |
| 3 | 7.155 | 7.282 | 7.2185 |
| 4 | 8.846 | 8.777 | Outliers |
| 5 | 6.985 | 6.983 | 6.984 |
| 6 | 7.106 | 7.296 | 7.201 |
| 7 | 6.543 | 6.665 | 6.604 |
| 8 | 7.715 | 7.772 | 7.7435 |
| 9 | 6.848 | 6.863 | 6.8555 |
| 10 | 7.205 | 7.322 | 7.2635 |
| 11 | 7.61 | 7.608 | 7.609 |
| 12 | 7.67 | 7.527 | 7.5985 |
| 13 | 7.715 | 7.673 | 7.694 |
| 14 | 7.144 | 7.069 | 7.1065 |
| 15 | 7.33 | 7.24 | 7.285 |
| Average | 7.220 | 7.227 | 7.224 |
| Max | 7.715 | 7.772 | 7.7435 |
| Min | 6.543 | 6.655 | 6.604 |
| Max − Min | 1.172 | 1.117 | 1.1395 |
| Std Dev | 0.374267 | 0.366072 | 0.365902 |

TABLE 10

WETTING TENSION MEASUREMENT OF COATED AND UNCOATED TUBES

| Example | Tube Coating | Wetting Tension (dyne/cm) |
|---|---|---|
| Reference | uncoated glass | 72 |
| Inventive Example | PET tube coated with SiO$_x$ according to SiO$_x$ Protocol | 60 |
| Comparative Example | uncoated PET | 40 |
| Inventive Example | PET tube coated according to Hydrophobic layer Protocol | 34 |
| Comparative Example | Glass (+silicone fluid) glass syringe, Part No. | 30 |

TABLE 11

WATER MASS DRAW (GRAMS)

| Tube | Pressurization Time (days) | | | | | | | |
|---|---|---|---|---|---|---|---|---|
| | 0 | 27 | 46 | 81 | 108 | 125 | 152 | 231 |
| BD PET (commercial control) | 3.0 | | | 1.9 | | 1.0 | | |
| Uncoated PET (internal control) | 4.0 | 3.1 | | | 2.7 | | | |
| SiO$_x$-Coated PET (inventive example) | 4.0 | 3.6 | | | 3.3 | | | |

TABLE 12

CALCULATED NORMALIZED AVERAGE VACUUM DECAY RATE AND TIME TO 10% VACUUM LOSS

| Tube | Normalized Average Decay rate (delta mL/initial mL · da) | Time to 10% Loss (months) - Accelerated |
|---|---|---|
| BD PET (commercial control) | 0.0038 | 0.9 |
| Uncoated PET (internal control) | 0.0038 | 0.9 |
| SiO$x$-Coated PET (inventive example) | 0.0018 | 1.9 |

TABLE 13

| Sample | Power, (Watts) | O—Si Flow, (sccm) | O$_2$ Flow, (sccm) | time (sec) | Avg. Force, (lb.) | St. dev. |
|---|---|---|---|---|---|---|
| SYRINGE BARRELS WITH LUBRICITY LAYER, ENGLISH UNITS | | | | | | |
| Glass with Silicone | No coating | No coating | No coating | No coating | 0.58 | 0.03 |
| Uncoated COC | No coating | No coating | No coating | No coating | 3.04 | 0.71 |
| A | 11 | 6 | 0 | 7 | 1.09 | 0.27 |
| B | 17 | 6 | 0 | 14 | 2.86 | 0.59 |
| C | 33 | 6 | 0 | 14 | 3.87 | 0.34 |
| D | 6 | 6 | 90 | 30 | 2.27 | 0.49 |
| Uncoated COC | — | — | — | — | 3.9 | 0.6 |
| SiO$_x$ on COC | | | | | 4.0 | 1.2 |
| E | 11 | 1.25 | 0 | 5 | 2.0 | 0.5 |
| F | 11 | 2.5 | 0 | 5 | 2.1 | 0.7 |
| G | 11 | 5 | 0 | 5 | 2.6 | 0.6 |
| H | 11 | 2.5 | 0 | 10 | 1.4 | 0.1 |
| I | 22 | 5 | 0 | 5 | 3.1 | 0.7 |
| J | 22 | 2.5 | 0 | 10 | 3.3 | 1.4 |
| K | 22 | 5 | 0 | 5 | 3.1 | 0.4 |
| SYRINGE BARRELS WITH LUBRICITY LAYER, METRIC UNITS | | | | | | |
| Glass syringe with sprayed silicone | No coating | No coating | No coating | No coating | 0.26 | 0.01 |
| Uncoated COC | No coating | No coating | No coating | No coating | 1.38 | 0.32 |
| A | 11 | 6 | 0 | 7 | 0.49 | 0.12 |
| B | 17 | 6 | 0 | 14 | 1.29 | 0.27 |
| C | 33 | 6 | 0 | 14 | 1.75 | 0.15 |
| D | 6 | 6 | 90 | 30 | 1.03 | 0.22 |
| Uncoated COC | — | — | | — | 1.77 | 0.27 |
| SiO$_x$ on COC, per protocol | | | | | 1.81 | 0.54 |
| E | 11 | 1.25 | — | 5 | 0.91 | 0.23 |
| F | 11 | 2.5 | — | 5 | 0.95 | 0.32 |
| G | 11 | 5 | — | 5 | 1.18 | 0.27 |
| H | 11 | 2.5 | — | 10 | 0.63 | 0.05 |
| I | 22 | 5 | — | 5 | 1.40 | 0.32 |
| J | 22 | 2.5 | — | 10 | 1.49 | 0.63 |
| K | 22 | 5 | — | 5 | 1.40 | 0.18 |

TABLE 14

PLUNGER SLIDING FORCE MEASUREMENTS OF HMDSO- AND OMCTS-BASED PLASMA COATINGS

| Example | Description | Monomer | Coating Time (sec) | Coating Si-O Flow Rate (sccm) | Coating Power (Watts) | Maximum Force (lb, kg.) | Normalized Maximum Force |
|---|---|---|---|---|---|---|---|
| A | uncoated Control | | | | | 3.3, 1.5 | 1.0 |
| B | HMDSO Coating | HMDSO | 7 | 6 | 8 | 4.1, 1.9 | 1.2 |
| C | OMCTS Lubricity layer | OMCTS | 7 | 6 | 8 | 1.1, 0.5 | 0.3 |
| D | uncoated Control | | | | | 3.9, 1.8 | 1.0 |
| E | OMCTS Lubricity layer | OMCTS | 7 | 6 | 11 | 2.0, 0.9 | 0.5 |
| F | Two Layer Coating | 1 COC Syringe Barrel + $SiO_x$ | 14 | 6 | 50 | | |
| | | 2 OMCTS Lubricity layer | 7 | 6 | 8 | 2.5, 1.1 | 0.6 |
| G | OMCTS Lubricity layer | OMCTS | 5 | 1.25 | 11 | 2, 0.9 | 0.5 |
| H | OMCTS Lubricity layer | OMCTS | 10 | 1.25 | 11 | 1.4, 0.6 | 0.4 |

TABLE 15

OTR AND WVTR MEASUREMENTS (Prophetic)

| Sample | OTR (cc/barrel · day) | WVTR (gram/barrel · day) |
|---|---|---|
| COC syringe- Comparative Example | 4.3 X | 3.0 Y |
| PVdC-COC laminate COC syringe- Inventive Example | X | Y |

TABLE 16

OPTICAL ABSORPTION OF SiOx COATED PET TUBES (NORMALIZED TO UNCOATED PET TUBE)

| Sample | Coating Time | Average Absorption (@ 615 nm) | Replicates | St. dev. |
|---|---|---|---|---|
| Reference (uncoated) | — | 0.002-0.014 | 4 | |
| Inventive A | 3 sec | 0.021 | 8 | 0.001 |
| Inventive B | 2 × 3 sec | 0.027 | 10 | 0.002 |
| Inventive C | 3 × 3 sec | 0.033 | 4 | 0.003 |

TABLE 17

ATOMIC CONCENTRATIONS (IN PERCENT, NORMALIZED TO 100% OF ELEMENTS DETECTED) AND TEM THICKNESS

| Sample | Plasma Coating | Si | O | C |
|---|---|---|---|---|
| HMDSO-based Coated COC syringe barrel | $Si_wO_xC_y$ | 0.76 (22.2%) | 1 (33.4%) | 3.7 (44.4%) |
| OMCTS- based Coated COC syringe barrel | $Si_wO_xC_y$ | 0.46 (23.6%) | 1 (28%) | 4.0 (48.4%) |

TABLE 17-continued

ATOMIC CONCENTRATIONS (IN PERCENT, NORMALIZED TO 100% OF ELEMENTS DETECTED) AND TEM THICKNESS

| Sample | Plasma Coating | Si | O | C |
|---|---|---|---|---|
| HMDSO Monomer- calculated | $Si_2OC_6$ | 2 (21.8%) | 1 (24.1%) | 6 (54.1%) |
| OMCTS Monomer- calculated | $Si_4O_4C_8$ | 1 (42%) | 1 (23.2%) | 2 (34.8%) |

TABLE 18

VOLATILE COMPONENTS FROM SYRINGE OUTGASSING

| | Coating Monomer | $Me_3SiOH$ (ng/test) | Higher SiOMe oligomers (ng/test) |
|---|---|---|---|
| Uncoated COC syringe - Comparative Example | Uncoated | ND | ND |
| HMDSO-based Coated COC syringe- Comparative Example | HMDSO | 58 | ND |
| OMCTS- based Coated COC syringe- Inventive Example | OMCTS | ND | 26 |

TABLE 19

PLASMA COATING DENSITY FROM XRR DETERMINATION

| Sample | Layer | Density g/cm³ |
|---|---|---|
| HMDSO-based Coated Sapphire - Comparative Example | $Si_wO_xC_yH_z$ | 1.21 |
| OMCTS- based Coated Sapphire - Inventive Example | $Si_wO_xC_yH_z$ | 1.46 |

TABLE 20

THICKNESS OF PECVD COATINGS BY TEM

| Sample ID | TEM Thickness I | TEM Thickness II | TEM Thickness III |
|---|---|---|---|
| Protocol for Forming COC Syringe Barrel; Protocol for Coating COC Syringe Barrel Interior with SiO$_x$ | 164 nm | 154 nm | 167 nm |
| Protocol for Forming COC Syringe Barrel; Protocol for Coating COC Syringe Barrel Interior with OMCTS Lubricity layer | 55 nm | 48 nm | 52 nm |
| Protocol for Forming PET Tube; Protocol for Coating Tube Interior with SiO$_x$ | 28 nm | 26 nm | 30 nm |
| Protocol for Forming PET Tube (uncoated) | — | — | — |

TABLE 21

OMCTS LUBRICITY LAYER PERFORMANCE (English Units)

| Sample | Average Plunger Force (lbs.)* | Percent Force Reduction (vs uncoated) | Power (Watts) | OMCTS Flow (sccm) |
|---|---|---|---|---|
| (English Units) | | | | |
| Comparative (no coating) | 3.99 | — | — | — |
| Sample A | 1.46 | 63% | 14 | 0.75 |
| Sample B | 1.79 | 55% | 11 | 1.25 |
| Sample C | 2.09 | 48% | 8 | 1.75 |
| Sample D | 2.13 | 47% | 14 | 1.75 |
| Sample E | 2.13 | 47% | 11 | 1.25 |
| Sample F | 2.99 | 25% | 8 | 0.75 |
| (Metric Units) | | | | |
| Comparative (no coating) | 1.81 | — | — | — |
| Sample A | 0.66 | 63% | 14 | 0.75 |
| Sample B | 0.81 | 55% | 11 | 1.25 |
| Sample C | 0.95 | 48% | 8 | 1.75 |
| Sample D | 0.96 | 47% | 14 | 1.75 |
| Sample E | 0.96 | 47% | 11 | 1.25 |
| Sample F | 1.35 | 25% | 8 | 0.75 |

*Average of 4 replicates

Above force measurements are the average of 4 samples.

The invention claimed is:

1. A catheter comprising
a substrate defining a contact surface for contact between the substrate and a fluid or tissue; and
a lubricity layer deposited on the contact surface and configured to provide a lower sliding force or breakout force for the contact surface than for the uncoated substrate;
the lubricity layer having one of the following atomic ratios, measured by X-ray photoelectron spectroscopy (XPS), Si$_w$O$_x$C$_y$ or Si$_w$N$_x$C$_y$, where w is 1, x in this formula is from about 0.5 to 2.4, and y is from about 0.6 to about 3;
the lubricity layer having a thickness by transmission electron microscopy (TEM) between 10 and 1000 nm;
the lubricity layer deposited by plasma enhanced chemical vapor deposition (PECVD) under conditions effective to form a coating from a precursor selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

2. The catheter of claim 1, in which the precursor is selected from a monocyclic siloxane, a polycyclic siloxane, a polysilsesquioxane, a monocyclic sila-zane, a polycyclic silazane, a polysilsesquiazane, a silatrane, a silquasilatrane, a silproatrane, an azasilatrane, an azasilquasiatrane, an azasilproatrane, or a combination of any two or more of these precursors.

3. The catheter of claim 1, in which the precursor comprises hexamethyldisiloxane, octamethyltrisiloxane, decamethyltetrasiloxane, hexamethylcyclotrisiloxane, octamethylcyclotetrasiloxane, decamethylcyclopentasiloxane, dodecamethylcyclohexasiloxane, a poly(methylsil-sesquioxane) according to the T$_8$ cube formula:

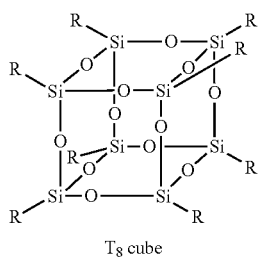

T$_8$ cube in which each R is methyl, a poly(Methyl-Hydridosilsesquioxane) according to the T$_8$ cube formula, in which 90% of the R groups are methyl and 10% are hydrogen atoms, methyltrimethoxysilane, or a combination of any two or more of these.

4. The catheter of claim 1, in which the precursor comprises octamethylcyclotetrasiloxane (OMCTS).

5. The catheter of claim 1, in which the precursor consists essentially of octamethylcyclotetrasiloxane (OMCTS).

6. A catheter comprising
a substrate defining a contact surface for contact between the substrate and a fluid or tissue; and
a barrier layer deposited on the contact surface and configured to reduce the transmission of a fluid to or from the contact surface;
the barrier layer having one of the following atomic ratios, measured by X-ray photoelectron spectroscopy (XPS), SiOx or SiNx, where x is from about 0.5 to 2.4;
the barrier layer having a thickness by transmission electron microscopy (TEM) between 1 and 1000 nm;
the barrier layer deposited by plasma enhanced chemical vapor deposition (PECVD) under conditions effective to form a coating from a precursor selected from a linear siloxane, a monocyclic siloxane, a polycyclic siloxane, a polysilsesquioxane, a linear silazane, a monocyclic silazane, a polycyclic silazane, a polysilsesquiazane, a silatrane, a silquasilatrane, a silproatrane, an azasilatrane, an azasilquasiatrane, an azasilproatrane, or a combination of any two or more of these precursors.

7. A catheter comprising a substrate defining a contact surface for contact between the substrate and a fluid or tissue;

the contact surface having a hydrophobic layer having the composition: $SiO_xC_y$ or $SiN_xC_y$, where x in this formula is from about 0.5 to 2.4 and y is from about 1.6 to about 3, of the type made by:
- providing a precursor selected from a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, or a combination of any two or more of these precursors;
- applying the precursor to a contact surface under conditions effective to form a coating; and
- polymerizing or crosslinking the coating, or both, to form a hydrophobic contact surface having a higher contact angle than the untreated contact surface.

8. The catheter of claim 7, in which the precursor comprises hexamethyldisiloxane, octamethyltrisiloxane, decamethyltetrasiloxane, hexamethylcyclotrisiloxane, octamethylcyclotetrasiloxane, decamethylcyclopenta-siloxane, dodecamethylcyclohexasiloxane, a silatrane, a silquasilatrane, a silproatrane, an azasilatrane, an azasilquasiatrane, an azasilproatrane, SST-eM01 poly(methylsilsesquioxane), in which each R is methyl, SST-3MH1.1 poly(Methyl-Hydridosilsesquioxane), in which 90% of the R groups are methyl and 10% are hydrogen atoms, methyl trimethoxysilane, or a combination of any two or more of these.

9. The catheter of claim 7, in which the precursor comprises octamethylcyclotetrasiloxane.

* * * * *